US008519224B2

(12) United States Patent
Davies et al.

(10) Patent No.: US 8,519,224 B2
(45) Date of Patent: Aug. 27, 2013

(54) GENERATION OF PLANTS WITH ALTERED PROTEIN, FIBER, OR OIL CONTENT

(75) Inventors: John P. Davies, Portland, OR (US); Hein Tsoeng (Medard) Ng, Charlottesville, VA (US); D. Ry Wagner, Pleasant Hill, OR (US)

(73) Assignee: Agrigenetics Inc., Indianapolis, IN (US)

( * ) Notice: Subject to any disclaimer, the term of this patent is extended or adjusted under 35 U.S.C. 154(b) by 0 days.

(21) Appl. No.: 13/476,801

(22) Filed: May 21, 2012

(65) Prior Publication Data

US 2012/0237664 A1  Sep. 20, 2012

Related U.S. Application Data

(62) Division of application No. 13/217,169, filed on Aug. 24, 2011, now Pat. No. 8,217,224, which is a division of application No. 11/940,269, filed on Nov. 14, 2007, now Pat. No. 8,030,541.

(60) Provisional application No. 60/866,055, filed on Nov. 15, 2006.

(51) Int. Cl.
C12N 15/82 (2006.01)
C12N 15/10 (2006.01)
C12N 15/00 (2006.01)
A01H 5/00 (2006.01)

(52) U.S. Cl.
USPC ........ 800/284; 800/278; 800/320.1; 800/295; 435/320.1; 435/468; 536/23.1; 536/23.6

(58) Field of Classification Search
None
See application file for complete search history.

(56) References Cited

U.S. PATENT DOCUMENTS

| | | | |
|---|---|---|---|
| 5,322,783 | A | 6/1994 | Tomes et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,610,042 | A | 3/1997 | Chang et al. |
| 5,639,790 | A | 6/1997 | Voelker et al. |
| 5,704,160 | A | 1/1998 | Bergquist et al. |
| 5,952,544 | A | 9/1999 | Browse et al. |
| 6,229,033 | B1 | 5/2001 | Knowlton |
| 6,248,939 | B1 | 6/2001 | Leto et al. |
| 6,750,046 | B2 | 6/2004 | Moloney et al. |
| 7,566,816 | B2 | 7/2009 | Lightner et al. |
| 2003/0046723 | A1 | 3/2003 | Heard et al. |
| 2004/0019927 | A1 | 1/2004 | Sherman et al. |
| 2004/0025202 | A1 | 2/2004 | Laurie et al. |
| 2005/0108791 | A1* | 5/2005 | Edgerton ............... 800/284 |
| 2006/0048240 | A1 | 3/2006 | Alexandrov et al. |
| 2006/0150283 | A1 | 7/2006 | Alexandrov et al. |
| 2006/0174375 | A1* | 8/2006 | Lightner et al. ............ 800/281 |
| 2006/0277630 | A1 | 12/2006 | Lightner et al. |
| 2007/0214517 | A1 | 9/2007 | Alexandrov et al. |

FOREIGN PATENT DOCUMENTS

| | | |
|---|---|---|
| EP | 1033405 | 9/2000 |
| WO | WO 94/11516 | 5/1994 |
| WO | WO 95/06128 | 3/1995 |
| WO | WO 2004/035798 | 4/2004 |
| WO | WO 2004/093528 | 11/2004 |
| WO | WO 2004/093532 | 11/2004 |
| WO | WO 2005/047516 | 5/2005 |
| WO | WO 2005/107437 | 11/2005 |
| WO | WO 2007/053482 | 5/2007 |

OTHER PUBLICATIONS

Anoop et al., "Modulation of citrate metabolism alters aluminum tolerance in yeast and transgenic canola overexpressing a mitochondrial citrate synthase," *Plant Physiol.*, 132:2205-2217, 2003.
Bateman et al., "Pfam 3.1: 1313 multiple alignments and profile HMMs match the majority of proteins," *Nucleic Acids Res.*, 27:260-262, 1999.
Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, (2003).
Browse et al., "Fluxes through the prokaryotic and eukaryotic pathways of lipid synthesis in the '16:3' plant *Arabidopsis thaliana*," *Biochem J.* 235:25-31 (1986).
Chapple and Carpita, "Plant cell walls as targets for biotechnology," *Current Opinion in Plant Biology*, 1:179-185 (1998).
Christensen et al., *9th International Conference on Arabidopsis Research*, Univ. of Wisconsin-Madison, Jun. 24-28, Abstract 165 (1998).
Christou et al., "Inheritance and expression of foreign genes in transgenic soybean plants," *Proc. Natl. Acad. Sci. USA*, 86:7500-7504 (1989).
Colbert et al., "High-throughput screening for induced point mutations," *Plant Physiol.* 126:480-484 (2001).
Database EMBL, "Arabidopsis thaliana unknown (At2g31480) mRNA, complete cds." Database Accession No. DQ056558; Jun. 20, 2005.
Database UNIPROT, "Putative uncharacterized protein," Database Accession No. Q4PSS8; Jul. 19, 2005.
De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).
Dehesh et al., "Overexpression of 3-ketoacyl-acyl-carrier protein synthase IIIs in plants reduces the rate of lipid synthesis," *Plant Physiol.*, 125:1103-1114, 2001.

(Continued)

*Primary Examiner* — Brent T Page
(74) *Attorney, Agent, or Firm* — Marcia I. Rosenfeld; Klarquist Sparkman, LLP

(57) ABSTRACT

The present invention is directed to plants that display an improved oil quantity phenotype or an improved meal quality phenotype due to altered expression of an IMQ nucleic acid. The invention is further directed to methods of generating plants with an improved oil quantity phenotype or improved meal quality phenotype.

6 Claims, No Drawings

(56) References Cited

OTHER PUBLICATIONS

Douglas et al., "Nutritional evaluation of low phytate and high protein corns," *Poultry Sci.* 79:1586-1591 (2000).
Eastmond and Graham, "Re-examining the role of glyoxylate cycle in oilseeds," *Trends Plant Sci.*, 6(2):72-77, 2001.
Eccleston and Ohlrogge, "Expression of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.
Edwards et al., "Protein and energy evaluation of soybean meals processed from genetically modified high-protein soybeans," *Poultry Sci.* 79:525-527 (1999).
Everett et al., "Genetic engineering of sunflower (*Helianthus annuus* L.)," *Bio/Technology*, 5:1201 (1987).
Falco et al., "Transgenic canola and soybean seeds with increased lysine," *Bio/Technology*, 13:577-582 (1995).
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in Arabidopsis," *Plant Cell*, 17:182-203, 2005.
Feldmann et al., "A Dwarf Mutant of Arabidopsis Generated by T-DNA Insertion Mutagenesis," *Science*, 243:1351-1354 (1989).
Focks and Benning, "wrinkled1: A novel, low-seed-oil mutant of Arabidopsis with a deficiency in the seed-specific regulation of carbohydrate metabolism," *Plant Physiol.*, 118:91-101 (1998).
Fridborg et al., "The Arabidopsis dwarf mutant *shi* exhibits reduced gibberellin responses conferred by overexpression of a new putative zinc finger protein," *Plant Cell*, 11:1019-1032 (1999).
Girke et al., "Microarray analysis of developing Arabidopsis seeds," *Plant Physiol.*, 124:1570-1581, 2000.
Hayashi et al., "Activation of a plant gene by T-DNA tagging: auxin-independent growth in vitro," *Science*, 258:1350-1353 (1992).
Honig and Rackis, "Determination of the total pepsin-pancreatin indigestible content (dietary fiber) of soybean products, wheat bran, and corn bran," *J. Agri. Food Chem.*, 27:1262-1266 (1979).
Jako et al., "Seed-specific over-expression of an Arabidopsis cDNA encoding a diacylglycerol acyltransferase enhances seed oil content and seed weight," *Plant Physiol.*, 126(2):861-74 (2001).
James and Dooner, "Isolation of EMS-induced mutants in Arabidopsis altered in seed fatty acid composition," *Theor. Appl. Genet.*, 80:241-245 (1990).
Kardailsky et al., "Activation tagging of the floral inducer FT," *Science*, 286:1962-1965 (1999).
Katavic et al., "Alteration of seed fatty acid composition by an ethyl methanesulfonate-induced mutation in Arabidopsis thaliana affecting diacylglycerol acyltransferase activity," *Plant Physiol.*, 108:399-409 (1995).
Katavic et al., "Utility of the *Arabidopsis FAE1* and yeast *SLC1-1* genes for improvements in erucic acid and oil content in rapeseed," *Biochem Soc. Trans.*, 28(6):935-937, 2000.
Klein et al., "High velocity microprojectiles for delivering nucleic acids into living cells," *Nature*, 327:70-73 (1987).
Larson et al., "Acyl CoA profiles of transgenic plants that accumulate medium-chain fatty acids indicate inefficient storage lipid synthesis in developing oilseeds," *Plant J.*, 32:519-527, 2002.
Lemieux et al., "Mutants of Arabidopsis with alterations in seed lipid fatty acid composition," *Theor. Appl. Genet.*, 80:234-240 (1990).
Lin et al., "The Pex16p Homolog SSE1 and Storage Organelle Formation in *Arabidopsis* Seeds," *Science*, 284:328-330, 1999.
Lionneton et al., "Development of an AFLP-based linkage map and localization of QTLs for seed fatty acid content in condiment mustard (*Brassica juncea*)," *Genome*, 45:1203-15 (2002).
Liu and Butow, "A transcriptional switch in the expression of yeast tricarboxylic acid cycle genes in response to a reduction or loss of respiratory function," *Mol. Cell. Biol.*, 19:6720-6728, 1999.
McCallum et al., "Targeted screening for induced mutations," *Nature Biotechnology*, 18:455-457 (2000).
Mekhedov et al., "Toward a Functional Catalog of the Plant Genome. A Survey of Genes for Lipid Biosynthesis," *Plant Physiology*, 122:389-401, 2000.
Moire et al., "Impact of Unusual Fatty Acid Synthesis on Futile Cycling through β-Oxidation and on Gene Expression in Transgenic Plants," *Plant Physiology*, 134:432-442, 2004.
Moore et al., "Chromatography of Amino Acids on Sulfonated Polystyrene Resins," *Anal. Chem.*, 30:1185-1190 (1958).
Mulder et al., "The InterPro Database, 2003 brings increased coverage and new features," *Nucleic Acids Res.*, 31:315-318, 2003.
Neuhaus et al., "Nonphotosynthetic Metabolism in Plastids," *Annu. Rev. Plant Physiol. Plant Mol.*, 51:111-140, 2000.
O'Hara et al., "Fatty Acid and Lipid Biosynthetic Genes Are Expressed at Constant Molar Ratios But Different Absolute Levels during Embryogenesis," *Plant Physiology*, 129:310-320, 2002.
Okuley et al., "Arabidopsis *FAD2* gene encodes the enzyme that is essential for polyunsaturated lipid synthesis," *Plant Cell*, 6:147-158 (1994).
Parsons et al., "Nutritional evaluation of soybean meals varying in oligosaccharide content," *Poultry Sci.*, 79:1127-1131 (2000).
Pritchard et al., "Germination and storage reserve mobilization are regulated independently in Arabidopsis," *The Plant Journal*, 31(5):639-647, 2002.
Rangasamy and Ratledge, "Genetic enhancement of fatty acid synthesis by targeting rat liver ATP:citrate lyase into plastids of tobacco," *Plant Physiol.*, 122:1231-1238, 2000.
Rangasamy et al., "Compartmentation of ATP:Citrate Lyase in Plants," *Plant Physiology*, 122:1225-1230, 2000.
Ratledge et al., "Correlation of ATP/Citrate Lyase Activity with Lipid Accumulation in Developing Seeds of *Brassica napus* L.," Lipids, 32(1):7-12, 1997.
Rawsthorne, Stephen, "Carbon flux and fatty acid synthesis in plants," *Progress in Lipid Research*, 41:182-196 (2002).
Ruuska et al., "Contrapuntal Networks of Gene Expression during Arabidopsis Seed Filling," *The Plant Cell*, 14:1191-1206, 2002.
Rylott et al., "Co-ordinate regulation of genes involved in storage lipid mobilization in *Arabidopsis thaliana*," *Biochem Soc. Trans.*, 29:283-287, 2001.
Schaffer et al., "The late elongated hypocotyl mutation of Arabidopsis disrupts circadian rhythms and the photoperiodic control of flowering," *Cell*, 93:1219-1229 (1998).
Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.
Schnurr et al., "Characterization of an acyl-CoA synthetase from *Arabidopsis thaliana*," *Biochem Soc. Trans.*, 28(6):957-958, 2000.
Shewry, "Seed storage proteins: structures and biosynthesis," *Plant Cell*, 7:945-956 (1995).
Shockey et al., "Characterization of the AMP-binding protein gene family in *Arabidopsis thaliana*: will the real acyl-CoA synthetases please stand up?" *Biochem Soc. Trans.*, 28(6):955-957, 2000.
Thelen et al., "Biotin carboxyl carrier protein isoforms in Brassicaceae oilseeds," *Biochem. Soc. Trans.*, 28(6):595-598, 2000.
Weigel et al., "Activation tagging in Arabidopsis," *Plant Physiology*, 122:1003-1013 (2000).
White et al., "A new set of Arabidopsis expressed sequence tags from developing seeds. The metabolic pathway from carbohydrates to seed oil," *Plant Physiol.*, 124:1582-1594, 2000.
Wilson et al., "A Dissociation insertion causes a semidominant mutation that increases expression of Tiny, an Arabidopsis gene related to APETALA2," *Plant Cell*, 8:659-671 (1996).
Yadav et al., "Cloning of higher plant omega-3 fatty acid desaturases," *Plant Physiol.*, 103:467-476 (1993).
Zou et al., "Modification of Seed Oil Content and Acyl Composition in the Brassicaceae by Expression of a Yeast *sn*-2 Acyltransferase Gene," *The Plant Cell*, 9:909-923 (1997).

* cited by examiner

GENERATION OF PLANTS WITH ALTERED PROTEIN, FIBER, OR OIL CONTENT

CROSS REFERENCE TO RELATED APPLICATIONS

This application is a divisional of U.S. patent application Ser. No. 13/217,169, filed Aug. 24, 2011, now U.S. Pat. No. 8,217,224 which is a divisional of U.S. patent application Ser. No. 11/940,269, filed Nov. 14, 2007, now U.S. Pat. No. 8,030,541, issued Oct. 4, 2011, which claims the benefit of U.S. Provisional Application No. 60/866,055, filed Nov. 15, 2006, each of which is incorporated herein by reference in its entirety.

FIELD OF THE DISCLOSURE

The present disclosure is related to transgenic plants with altered oil, protein, and/or fiber content, as well as methods of making plants having altered oil, protein, and/or fiber content and producing oil from such plants.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on May 9, 2012, and having a size of ~260 kilobytes, as permitted under 37 CFR 1.821(c). The material in the aforementioned file is hereby incorporated by reference in its entirety.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80, 234-240; James and Dooner, 1990, *Theor. Appl. Genet.* 80, 241-245). T-DNA mutagenesis screens (Feldmann et al., 1989, *Science* 243: 1351-1354) that detected altered fatty acid composition identified the omega 3 desaturase (FADS) and delta-12 desaturase (FAD2) genes (U.S. Pat. No. 5,952,544; Yadav et al., 1993, *Plant Physiol.* 103, 467-476; Okuley et al., 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9$^{th}$ *International Conference on Arabidopsis Research*, Univ. of Wisconsin-Madison, June 24-28, Abstract 165).

SUMMARY

Provided herein are transgenic plants having an Improved Seed Quality phenotype. Transgenic plants with an Improved Seed Quality phenotype may include an improved oil quantity and/or an improved meal quality. Transgenic plants with improved meal quality have an Improved Meal Quality (IMQ) phenotype and transgenic plants with improved oil quantity have an Improved Oil Quantity (IOQ) phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Examples of the disclosed transgenic plant are produced by a method that comprises introducing into progenitor cells of the plant a plant transformation vector comprising an IMQ nucleotide sequence that encodes, or is complementary to a sequence that encodes, an IMQ polypeptide, and growing the transformed progenitor cells to produce a transgenic plant, wherein the IMQ polynucleotide sequence is expressed, causing an IOQ phenotype and/or and IMQ phenotype in the transgenic plant. In some specific, non-limiting examples, the method produces transgenic plants wherein expression of the IMQ polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. In some embodiments of the method, the method employs candidate gene/QTL methodology or TILLING methodology.

Also provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "IMQ phenotype" refers to plants, or any part of a plant (for example, seeds, or meal produced from seeds), with an altered protein and/or fiber content (phenotype). As provided herein, altered protein and/or fiber content includes either an increased or decreased level of protein and/or fiber content in plants, seeds or seed meal. Any combination of these changes can lead to an IMQ phenotype. For example, in one specific non-limiting example, an IMQ phenotype can refer to increased protein and decreased fiber content. In another specific non-limiting example, an IMQ phenotype can refer to unchanged protein and decreased fiber content. In yet another specific non-limiting example, an IMQ phenotype can refer to increased protein and unchanged fiber content. It is also provided that any combination of these changes can lead to an increase in the AME (available metabolizable energy) from the seed or meal generated from the seed. An IMQ phenotype also includes an improved seed quality (ISQ) phenotype or an improved seed meal quality phenotype.

As used herein, the term "IOQ phenotype" refers to plants, or any part of a plant (for example, seeds), with an altered oil content (phenotype). As provided herein, altered oil content includes an increased, for example a high, oil content in plants or seeds. In some embodiments, a transgenic plant can express both an IOQ phenotype and an IMQ phenotype. In specific, non-limiting examples, a transgenic plant having a combination of an IOQ phenotype and an IMQ phenotype can lead to an increase in the AME (available metabolizable energy) from the seed or meal generated from the seed. An IOQ phenotype also includes an improved seed quality (ISQ) phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a transgenic plant with an increase in AME includes transgenic plants with altered seed protein and/or fiber content and without a decrease in seed oil content (seed oil content remains unchanged or is increased), resulting in an increase in the value of animal feed derived from the seed.

As used herein, the term "content" refers to the type and relative amount of, for instance, a seed or seed meal component.

As used herein, the term "fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include an IMQ nucleic acid sequence, or a fragment, derivative (variant), or ortholog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wild-type plant is a non-transgenic plant.

As used herein, the term "modified" regarding a plant trait, refers to a change in the phenotype of a transgenic plant (for example, a transgenic plant with any combination of an altered oil content, an altered protein content, and/or an altered fiber content) in any part of the transgenic plant, for example the seeds, relative to a similar non-transgenic plant. As used herein, the term "altered" refers to either an increase or a decrease of a plant trait or phenotype (for example, oil content, protein content, and/or fiber content) in a transgenic plant, relative to a similar non-transgenic plant. In one specific, non-limiting example, a transgenic plant with a modified trait includes a plant with an increased oil content, increased protein content, and/or decreased fiber content relative to a similar non-transgenic plant. In another specific, non-limiting example, a transgenic plant with a modified trait includes unchanged oil content, increased protein content, and/or decreased fiber content relative to a similar non-transgenic plant. In yet another specific, non-limiting example, a transgenic plant with a modified trait includes an increased oil content, increased protein content, and/or unchanged fiber content relative to a similar non-transgenic plant. Specific, non-limiting examples of a change in phenotype include an IMQ phenotype or an IOQ phenotype.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an IMQ phenotype or an IOQ phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil phenotype refers to an increase in overall oil content. The phrase "altered protein content phenotype" refers to measurable phenotype of a genetically modified plant, where the plant displays a statistically significant increase or decrease in overall protein content (i.e., the percentage of seed mass that is protein), as compared to the similar, but non-modified plant. A high protein phenotype refers to an increase in overall protein content. The phrase "altered fiber content phenotype" refers to measurable phenotype of a genetically modified plant, where the plant displays a statistically significant increase or decrease in overall fiber content (i.e., the percentage of seed mass that is fiber), as compared to the similar, but non-modified plant. A low fiber phenotype refers to decrease in overall fiber content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of TO plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having an Improved Seed Quality phenotype. Transgenic plants with an Improved Seed Quality phenotype may include an improved oil quantity and/or an improved meal quality. Transgenic plants with improved meal quality have an IMQ phenotype and transgenic plants with improved oil quantity have an IOQ phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods (see, for example, WO 2007/053482 and WO 2005/107437, which are incorporated herein by reference in their entirety).

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880, U.S. Pat. No. 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin), methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, and U.S. Pat. No. 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al. (*Plant J.* 4:833-840, 1993) and Misawa et al. (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock et al. (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, *Physiol. Plant,* 15:473-497, 1962) or N6-based media (Chu et al., *Scientia Sinica* 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Improved Oil Quantity Phenotype and/or Improved Meal Quality Phenotype An *Arabidopsis* activation tagging screen (ACTTAG) was used to identify the association between 1) ACTTAG plant lines with an altered protein, fiber and/or oil content (phenotype, for example, see columns 4, 5 and 6, respectively, of Table 1, below) and 2) the nucleic acid sequences identified in column 3 of Tables 2 and 3, wherein each nucleic acid sequence is provided with a gene alias or an IMQ designation (IMQ#; see column 1 in Tables 1, 2, and 3). Briefly, and as further described in the Examples, a large number of *Arabidopsis* plants were mutated with the pSKI015 vector, which comprises a T-DNA from the Ti plasmid of *Agrobacterium tumefaciens*, a viral enhancer element, and a selectable marker gene (Weigel et al., 2000, *Plant Physiology,* 122: 1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

Quantitative determination of fatty acid (FA) content (column 7, Table 1) in T2 seeds was performed using the following methods. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 µl 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 µl of water and 400 µl of hexane were added to each vial, which was then shaken vigorously and allowed to phase separate. Reaction vials were loaded directly onto gas chromatography (GC) for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 µl of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Peaks were initially identified by comparison with standards. Integration and quantification were performed automatically, but all analyses were subsequently examined manually to verify correct peak identification and acceptable signal to noise ratio before inclusion of the derived results in the study.

The association of an IMQ nucleic acid sequence with an IMQ phenotype or an IOQ phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed IMQ nucleic acid sequences and/or polypeptides may be employed in the development of transgenic plants having an improved seed quality phenotype, including an IMQ phenotype and/or an IOQ phenotype. IMQ nucleic acid sequences may be used in the generation of transgenic plants, such as oilseed crops, that provide improved oil yield from oilseed processing and result in an increase in the quantity of oil recovered from seeds of the transgenic plant. IMQ nucleic acid sequences may also be used in the generation of transgenic plants, such as feed grain crops, that provide an IMQ phenotype resulting in increased energy for animal feeding, for example, seeds or seed meal with an altered protein and/or fiber content, resulting in an increase in AME. IMQ nucleic acid sequences may further be used to increase the oil content of specialty oil crops, in order to augment yield and/or recovery of desired unusual fatty acids. Transgenic plants that have been genetically modified to express IMQ polypeptides can be used in the production of seeds, wherein the transgenic plants are grown, and oil and seed meal are obtained from plant parts (e.g. seed) using standard methods.

IMO Nucleic Acids and Polypeptides

The IMQ designation for each of the IMQ nucleic acid sequences discovered in the activation tagging screen described herein are listed in column 1 of Tables 1-3, below. The disclosed IMQ polypeptides are listed in column 5 of Table 2 and column 4 of Table 3. As used herein, the term "IMQ polypeptide" refers to any polypeptide that when expressed in a plant causes an IMQ phenotype and/or an IOQ phenotype in any part of the plant, for example the seeds. In one embodiment, an IMQ polypeptide refers to a full-length IMQ protein, or a fragment, derivative (variant), or ortholog thereof that is "functionally active," such that the protein fragment, derivative, or ortholog exhibits one or more or the functional activities associated with one or more of the disclosed full-length IMQ polypeptides, for example, the amino acid sequences provided in the GenBank entry referenced in column 5 of Table 2, which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof. In one preferred embodiment, a functionally active IMQ polypeptide causes an IMQ phenotype and/or an IOQ phenotype in a transgenic plant. In another embodiment, a functionally active IMQ polypeptide causes an altered oil, protein, and/or fiber content phenotype (for example, an altered seed meal content phenotype) when mis-expressed in a plant. In other preferred embodiments, mis-expression of the IMQ polypeptide causes a high oil (such as, increased oil), high protein (such as, increased protein), and/or low fiber (such as, decreased fiber) phenotype in a plant. In another embodiment, mis-expression of the IMQ polypeptide causes an improved AME of meal. In yet another embodiment, a functionally active IMQ polypeptide can rescue defective (including deficient) endogenous IMQ activity when expressed in a plant or in plant cells; the rescuing polypeptide may be from the same or from a different species as the species with the defective polypeptide activity. The disclosure also provides feed, meal, grain, food, or seed comprising the IMQ polypeptide, or a fragment, derivative (variant), or ortholog thereof.

In another embodiment, a functionally active fragment of a full length IMQ polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or a naturally occurring ortholog thereof) retains one or more of the biological properties associated with the full-length IMQ polypeptide, such as signaling activity, binding activity, catalytic activity, or cellular or extra-cellular localizing activity. An IMQ fragment preferably comprises an IMQ domain, such as a C- or N-terminal or catalytic domain, among others, and preferably comprises at least 10, preferably at least 20, more preferably at least 25, and most preferably at least 50 contiguous amino acids of an IMQ protein. Functional domains of IMQ genes are listed in column 8 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length IMQ polypeptides, or fragments thereof, include polypeptides with amino acid insertions, deletions, or substitutions that retain one of more of the biological properties associated with the full-length IMQ polypeptide. In some cases, variants are generated that change the post-translational processing of an IMQ polypeptide. For instance, variants may have altered protein transport or protein localization characteristics, or altered protein half-life, compared to the native polypeptide.

As used herein, the term "IMQ nucleic acid" refers to any polynucleotide that when expressed in a plant causes an IMQ phenotype and/or an IOQ phenotype in any part of the plant, for example the seeds. In one embodiment, an IMQ polynucleotide encompasses nucleic acids with the sequence provided in or complementary to the GenBank entry referenced in column 3 of Table 2, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, as well as functionally active fragments, derivatives, or orthologs thereof. An IMQ nucleic acid of this disclosure may be DNA, derived from genomic DNA or cDNA, or RNA. Genomic sequences of the genes listed in Table 2 are known and available in public databases such as GenBank.

In one embodiment, a functionally active IMQ nucleic acid encodes or is complementary to a nucleic acid that encodes a functionally active IMQ polypeptide. A functionally active IMQ nucleic acid also includes genomic DNA that serves as a template for a primary RNA transcript (i.e., an mRNA precursor) that requires processing, such as splicing, before encoding the functionally active IMQ polypeptide. An IMQ nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed IMQ polypeptide, or an intermediate form. An IMQ polynucleotide can also include heterologous coding sequences, for example, sequences that encode a marker included to facilitate the purification of the fused polypeptide, or a transformation marker. In another embodiment, a functionally active IMQ nucleic acid is capable of being used in the generation of loss-of-function IMQ phenotypes, for instance, via antisense suppression, co-suppression, etc. The disclosure also provides feed, meal, grain, food, or seed comprising a nucleic acid sequence that encodes an IMQ polypeptide.

In one preferred embodiment, an IMQ nucleic acid used in the disclosed methods comprises a nucleic acid sequence that encodes, or is complementary to a sequence that encodes, an IMQ polypeptide having at least 50%, 60%, 70%, 75%, 80%, 85%, 90%, 95%, 97%, 98%, or 99% sequence identity to a disclosed IMQ polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

In another embodiment, an IMQ polypeptide comprises a polypeptide sequence with at least 50% or 60% identity to a disclosed IMQ polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100) and may have at least 70%, 80%, 85%, 90%, 95%, 97%, 98%, or 99% sequence identity to a disclosed IMQ polypeptide sequence. In a further embodiment, an IMQ polypeptide comprises 50%, 60%, 70%, 80%, 85%, 90%, 95%, 97%, 98%, or 99% sequence identity to a disclosed IMQ polypeptide sequence, and may include a conserved protein domain of the IMQ polypeptide (such as the protein domain(s) listed in column 8 of Table 2). In another embodiment, an IMQ polypeptide comprises a polypeptide sequence with at least 50%, 60%, 70%, 80%, 85%, 90%, 95%, 97%, 98%, or 99% sequence identity to a functionally active fragment of the polypeptide referenced in column 5 of Table 2. In yet another embodiment, an IMQ polypeptide comprises a polypeptide sequence with at least 50%, 60%, 70%, 80%, 90%, 95%, 97%, 98%, or 99% identity to the polypeptide sequence of the GenBank entry referenced in column 5 of Table 2 over its entire length and comprises a conserved protein domain(s) listed in column 8 of Table 2.

In another aspect, an IMQ polynucleotide sequence is at least 50% to 60% identical over its entire length to a disclosed IMQ nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and may comprise at least 70%, 80%, 85%, 90%, 95%, 97%, 98%, or 99% sequence identity to the disclosed IMQ sequence, or a functionally active fragment thereof, or complementary sequences. In another embodiment, a disclosed IMQ nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and nucleic acid sequences that have substantial sequence homology to a such IMQ sequences. As used herein, the phrase "substantial sequence homology" refers to those nucleic acid sequences that have slight or inconsequential sequence variations from such IMQ sequences, i.e., the sequences function in substantially the same manner and encode an IMQ polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., $J.$ $Mol.$ $Biol.,$ 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed IMQ nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99). The stringency of hybridization can be controlled by temperature, ionic strength, pH, and the presence of denaturing agents such as formamide during hybridization and washing. Conditions routinely used are well known (see, e.g., $Current$ $Protocol$ $in$ $Molecular$ $Biology,$ Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding an IMQ polypeptide can be produced. For example, codons may be selected to increase the rate at which expression of the polypeptide occurs in a particular host species, in accordance with the optimum codon usage dictated by the particular host organism (see, e.g., Nakamura et al., 1999, $Nucleic$ $Acids$ $Res.$ 27:292). Such sequence variants may be used in the methods disclosed herein.

The disclosed methods may use orthologs of a disclosed $Arabidopsis$ IMQ nucleic acid sequence. Representative putative orthologs of each of the disclosed $Arabidopsis$ IMQ genes are identified in column 3 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as $Arabidopsis,$ may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, $Proc.$ $Natl.$ $Acad.$ $Sci.,$ 95:5849-5856; Huynen M A et al., 2000, $Genome$ $Research,$ 10:1204-1210).

Programs for multiple sequence alignment, such as CLUSTAL (Thompson J D et al., 1994, $Nucleic$ $Acids$ $Res.$ 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* IMQ coding sequence may be used as a probe. IMQ ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known IMQ polypeptides are used for ortholog isolation (see, e.g., Harlow and Lane, 1988, 1999, *Antibodies: A Laboratory Manual*, Cold Spring Harbor Laboratory Press, New York). Western blot analysis can determine that an IMQ ortholog (i.e., a protein orthologous to a disclosed IMQ polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which IMQ nucleic acid and/or polypeptide sequences have been identified.

IMQ nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the IMQ nucleic acid into a plant expression vector for transformation of plant cells, and the IMQ polypeptide is expressed in the host plant. Transformed plants and plant cells expressing an IMQ polypeptide express an IMQ phenotype and/or an IOQ phenotype and, in one specific, non-limiting example, may have high (increased) oil, high (increased) protein, and/or low (decreased) fiber content.

An "isolated" IMQ nucleic acid molecule is other than in the form or setting in which it is found in nature, and is identified and separated from least one contaminant nucleic acid molecule with which it is ordinarily associated in the natural source of the IMQ nucleic acid. However, an isolated IMQ nucleic acid molecule includes IMQ nucleic acid molecules contained in cells that ordinarily express IMQ where, for example, the nucleic acid molecule is in a chromosomal location different from that of natural cells.

Generation of Genetically Modified Plants with an Improved Oil Quantity Phenotype and/or an Improved Meal Quality Phenotype The disclosed IMQ nucleic acids and polypeptides may be used in the generation of transgenic plants having a modified or altered oil, protein, and/or fiber content phenotype. As used herein, an "altered oil content (phenotype)" may refer to altered oil content in any part of the plant. In a preferred embodiment, altered expression of the IMQ gene in a plant is used to generate plants with a high oil content (phenotype). As used herein, an "altered protein content (phenotype)" may refer to altered protein content in any part of the plant. In a preferred embodiment, altered expression of the IMQ gene in a plant is used to generate plants with a high (or increased) protein content (phenotype). As used herein, an "altered fiber content (phenotype)" may refer to altered fiber content in any part of the plant. In a preferred embodiment, altered expression of the IMQ gene in a plant is used to generate plants with a low (or decreased) fiber content (phenotype). The altered oil, protein, and/or fiber content is often observed in seeds. Examples of a transgenic plant include plants comprising a plant transformation vector with a nucleotide sequence that encodes or is complementary to a sequence that encodes an IMQ polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the IMQ nucleic acid sequence (or an ortholog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species may also be a source of unique fatty acids. In other embodiments, any plant expressing the IMQ nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an IMQ polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.*, 91:694-701), sunflower (Everett et al., 1987, *Bio/Technology*, 5:1201), soybean (Christou et al., 1989, *Proc. Natl. Acad. Sci USA*, 86:7500-7504; Kline et al., 1987, *Nature*, 327:70), wheat, rice and oat.

Expression (including transcription and translation) of an IMQ nucleic acid sequence may be regulated with respect to the level of expression, the tissue type(s) where expression takes place and/or developmental stage of expression. A number of heterologous regulatory sequences (e.g., promoters and enhancers) are available for controlling the expression of an IMQ nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (*U.S.A.*) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.*, 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (*U.S.A.*) 84:6624-6628, 1987), the sucrose synthase promoter (Yang et al., *Proc. Natl. Acad. Sci.* (*U.S.A.*) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol Biol.*, 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol Bio.*, 21:625-640).

In one preferred embodiment, expression of the IMQ nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209: 219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (U.S. Application No. 2003/0046727), a soybean 7S promoter, a 7Sα promoter (U.S. Application No. 2003/0093828), the soybean 7Sα' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.*, 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No.

2003/229918) and *Zea mays* L3 oleosin promoter (Hong et al., *Plant Mol. Biol.*, 34(3):549-555, 1997). Also included are the zeins, which are a group of storage proteins found in corn endosperm. Genomic clones for zein genes have been isolated (Pedersen et al., *Cell*, 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba legumin* (Baumlein et al., 1991, *Mol. Gen. Genet.* 225:121-8; Baumlein et al., 1992, *Plant J.* 2:233-9), *V. faba usp* (Fiedler et al., 1993, *Plant Mol. Biol.* 22:669-79), pea *convicilin* (Bown et al., 1988, *Biochem. J.* 251:717-26), pea *lectin* (dePater et al., 1993, *Plant Cell* 5:877-86), *P. vulgaris beta phaseolin* (Bustos et al., 1991, *EMBO J.* 10:1469-79), *P. vulgaris* DLEC2 and PHS [beta] (Bobb et al., 1997, *Nucleic Acids Res.* 25:641-7), and soybean *beta-Conglycinin*, 7S storage protein (Chamberland et al., 1992, *Plant Mol. Biol.* 19:937-49).

Cereal genes whose promoters are associated with early seed and embryo development include rice *glutelin* ("GluA-3,"Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice *prolamin* (Zhou & Fan, 1993, *Transgenic Res.* 2:141-6), wheat *prolamin* (Hammond-Kosack et al., 1993, *EMBO J.* 12:545-54), maize *zein* (Z4, Matzke et al., 1990, *Plant Mol. Biol.* 14:323-32), and barley *B-hordeins* (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus napin*, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus oleosin* (Keddie et al., 1994, *Plant Mol. Biol.* 24:327-40), *Arabidopsis oleosin* (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of the endogenous IMQ nucleic acid sequence in a host cell. Exemplary methods for practicing this aspect of the invention include, but are not limited to antisense suppression (Smith, et al., 1988, *Nature*, 334:724-726; van der Krol et al., 1988, *BioTechniques*, 6:958-976); co-suppression (Napoli, et al., 1990, *Plant Cell*, 2:279-289); ribozymes (PCT Publication WO 97/10328); and combinations of sense and antisense (Waterhouse, et al., 1998, *Proc. Natl. Acad. Sci. USA*, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA*, 85:8805-8809), a partial cDNA sequence including fragments of 5' coding sequence, (Cannon et al., 1990, *Plant Mol. Biol.*, 15:39-47), or 3' non-coding sequences (Ch'ng et al., 1989, *Proc. Natl. Acad. Sci. USA*, 86:10006-10010). Cosuppression techniques may use the entire cDNA sequence (Napoli et al., 1990, *Plant Cell*, 2:279-289; van der Krol et al., 1990, *Plant Cell*, 2:291-299), or a partial cDNA sequence (Smith et al., 1990, *Mol. Gen. Genetics*, 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Improved Oil Quantity Phenotype and/or Improved Meal Quality Phenotype Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. For example, provided herein is a method of identifying plants that have mutations in the endogenous IMQ nucleic acid sequence that confer an IMQ phenotype and/or an IOQ phenotype and generating progeny of these plants with an IMQ and/or IOQ phenotype that are not genetically modified. In some embodiments, the plants have an IMQ phenotype with an altered protein and/or fiber content or seed meal content, or an IOQ phenotype, with an altered oil content.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the IMQ nucleic acid sequence is used to identify whether a mutated plant has a mutation in the IMQ nucleic acid sequence. Plants having IMQ mutations may then be tested for altered oil, protein, and/or fiber content, or alternatively, plants may be tested for altered oil, protein, and/or fiber content, and then PCR amplification and sequencing of the IMQ nucleic acid sequence is used to determine whether a plant having altered oil, protein, and/or fiber content has a mutated IMQ nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the IMQ nucleic acid sequence or orthologs of the IMQ nucleic acid sequence that may confer altered oil, protein, and/or fiber content (see Bert et al., *Theor Appl Genet.*, 2003 June; 107(1):181-9; and Lionneton et al., *Genome*, 2002 December; 45(6):1203-15). Thus, in a further aspect of the disclosure, an IMQ nucleic acid is used to identify whether a plant having altered oil, protein, and/or fiber content has a mutation an endogenous IMQ nucleic acid sequence or has a particular allele that causes altered oil, protein, and/or fiber content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with an IMQ Phenotype and/or an IOQ Phenotype by Transformation with an Activation Tagging Construct This Example describes the generation of transgenic plants with altered oil, protein, and/or fiber content.

Mutants were generated using the activation tagging "ACT-TAG" vector, pSKI015 (GI#6537289; Weigel D et al., 2000, Plant Physiology, 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR protein content predicting calibration was developed using total nitrogen content data of seed samples following the general method of Dumas Procedure AOAC 968.06 (Official Methods of Analysis of AOAC International $17^{th}$ Edition AOAC, Gaithersburg, Md.). A fiber content predicting calibration was developed by measuring crude fiber content in a set of seed samples. Fiber content of in a known mass of seed was determined using the method of Honig and Rackis, (1979, *J. Agri. Food Chem.*, 27: 1262-1266). Digestible protein content of in a known mass of seed was determined by quantifying the individual amino acids liberated by an acid hydrolysis Steine and Moore (1958, *Anal. Chem.*, 30:1185-1190). The quantification was performed by the Amino Quant (Agilent). The undigested protein remaining associated with the non digestible fraction is measured by the same method described for the whole seed homogenate. Digestible protein content is determined by subtracting the amount of undigested protein associated with the non digestible fraction from the total amount of protein in the seed sample.

Seed oil, protein, digestible protein and fiber values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Promoters within 9 kb of the enhancers in the ACTTAG element are considered to be within "activation space." Genes with T-DNA inserts within coding sequences were not considered to be within "activation space." The ACTTAG lines with the above average oil and protein values, and below average fiber values were identified and are listed in column 3 of Table 1.

TABLE 1

| 1. Gene alias | 2. Tair | 3. ACTTAG Line | 4. Relative Seed Protein Content | 5. Relative Seed Fiber Content | 6. Relative Seed Oil Content | 7. GC FA |
|---|---|---|---|---|---|---|
| IMQ34.3 | At2g31480 | W000137133 | 135.45% | 89.55% | 82.65% | |
| IMQ34.4 | At2g31490 | W000137133 | 135.45% | 89.55% | 82.65% | |
| IMQ35.1 | At2g34030 | W000041983 | 122.86% | 92.93% | 80.44% | |
| IMQ35.2 | At2g34040 | W000041983 | 122.86% | 92.93% | 80.44% | |
| IMQ35.2 | At2g34040 | W000041983 | 122.86% | 92.93% | 80.44% | |
| IMQ35.3 | At2g34050 | W000041983 | 122.86% | 92.93% | 80.44% | |
| IMQ35.4 | At2g34060 | W000041983 | 122.86% | 92.93% | 80.44% | |
| IMQ36.1 | At2g34400 | W000146178 | 109.53% | 93.15% | 94.98% | |
| IMQ36.2 | At2g34410 | W000146178 | 109.53% | 93.15% | 94.98% | |
| IMQ36.2 | At2g34410 | W000146178 | 109.53% | 93.15% | 94.98% | |
| IMQ36.2 | At2g34410 | W000146178 | 109.53% | 93.15% | 94.98% | |
| IMQ36.3 | At2g34420 | W000146178 | 109.53% | 93.15% | 94.98% | |
| IMQ36.3 | At2g34420 | W000146178 | 109.53% | 93.15% | 94.98% | |
| IMQ36.4 | At2g34430 | W000146178 | 109.53% | 93.15% | 94.98% | |
| IMQ36.5 | At2g34440 | W000146178 | 109.53% | 93.15% | 94.98% | |
| IMQ36.6 | At2g34450 | W000146178 | 109.53% | 93.15% | 94.98% | |
| IMQ36.6 | At2g34450 | W000146178 | 109.53% | 93.15% | 94.98% | |
| IMQ37.1 | At3g03800 | W000168536 | 105.07% | 88.55% | 98.42% | |
| IMQ37.2 | At3g03810 | W000168536 | 105.07% | 88.55% | 98.42% | |
| IMQ37.3 | At3g03820 | W000168536 | 105.07% | 88.55% | 98.42% | |
| IMQ37.4 | At3g03830 | W000168536 | 105.07% | 88.55% | 98.42% | |
| IMQ37.5 | At3g03840 | W000168536 | 105.07% | 88.55% | 98.42% | |
| IMQ37.6 | At3g03847 | W000168536 | 105.07% | 88.55% | 98.42% | 97.87% |
| IMQ37.7 | At3g03850 | W000168536 | 105.07% | 88.55% | 98.42% | |
| IMQ38.1 | At3g07100 | W000182714 | 101.56% | 90.13% | 99.68% | |
| IMQ38.2 | At3g07110 | W000182714 | 101.56% | 90.13% | 99.68% | |
| IMQ38.2 | At3g07110 | W000182714 | 101.56% | 90.13% | 99.68% | |
| IMQ38.3 | At3g07120 | W000182714 | 101.56% | 90.13% | 99.68% | |
| IMQ38.4 | At3g07130 | W000182714 | 101.56% | 90.13% | 99.68% | |
| IMQ38.5 | At3g07140 | W000182714 | 101.56% | 90.13% | 99.68% | |
| IMQ38.5 | At3g07140 | W000182714 | 101.56% | 90.13% | 99.68% | |
| IMQ38.6 | At3g07150 | W000182714 | 101.56% | 90.13% | 99.68% | |
| IMQ39.1 | At3g15480 | W000190425 | 151.85% | 106.23% | 57.69% | |
| IMQ39.2 | At3g15490 | W000190425 | 151.85% | 106.23% | 57.69% | 69.66% |
| IMQ39.3 | At3g15500 | W000190425 | 151.85% | 106.23% | 57.69% | |
| IMQ40.1 | At3g16580 | W000085366 | 119.68% | 89.13% | 84.56% | 99.63% |
| IMQ40.2 | At3g16590 | W000085366 | 119.68% | 89.13% | 84.56% | |
| IMQ40.3 | At3g16600 | W000085366 | 119.68% | 89.13% | 84.56% | |
| IMQ40.4 | At3g16610 | W000085366 | 119.68% | 89.13% | 84.56% | |
| IMQ40.5 | At3g16620 | W000085366 | 119.68% | 89.13% | 84.56% | |
| IMQ41.1 | At3g17640 | W000192636 | 101.54% | 86.92% | 102.79% | 107.27% |
| IMQ41.2 | At3g17650 | W000192636 | 101.54% | 86.92% | 102.79% | |
| IMQ41.3 | At3g17660 | W000192636 | 101.54% | 86.92% | 102.79% | |
| IMQ41.4 | At3g17670 | W000192636 | 101.54% | 86.92% | 102.79% | |
| IMQ41.5 | At3g17680 | W000192636 | 101.54% | 86.92% | 102.79% | 107.27% |
| IMQ41.5 | At3g17680 | W000192636 | 101.54% | 86.92% | 102.79% | |
| IMQ41.6 | At3g17690 | W000192636 | 101.54% | 86.92% | 102.79% | 107.27% |
| IMQ42.1 | At3g19850 | W000093675 | 112.46% | 94.21% | 95.25% | |
| IMQ42.2 | At3g19860 | W000093675 | 112.46% | 94.21% | 95.25% | |
| IMQ42.2 | At3g19860 | W000093675 | 112.46% | 94.21% | 95.25% | |

TABLE 2

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ34.3 | At2g31480 | gi|42569515 | SEQ ID NO: 1 | gi|42569516 | SEQ ID NO: 2 | unknown protein | |
| IMQ34.4 | At2g31490 | gi|18402681 | SEQ ID NO: 3 | gi|18402682 | SEQ ID NO: 4 | unknown protein | |
| IMQ35.1 | At2g34030 | gi|42569600 | SEQ ID NO: 5 | gi|42569601 | SEQ ID NO: 6 | calcium ion binding | IPR002048 Calcium-binding EF-hand |
| IMQ35.2 | At2g34040 | gi|30685905 | SEQ ID NO: 7 | gi|30685906 | SEQ ID NO: 8 | unknown protein | IPR008383 Apoptosis inhibitory 5 |
| IMQ35.2 | At2g34040 | gi|30685899 | SEQ ID NO: 9 | gi|18403429 | SEQ ID NO: 10 | unknown protein | IPR008383 Apoptosis inhibitory 5 |
| IMQ35.3 | At2g34050 | gi|30685908 | SEQ ID NO: 11 | gi|18403431 | SEQ ID NO: 12 | unknown protein | IPR010591 ATP11 |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ35.4 | At2g34060 | gi\|30685912 | SEQ ID NO: 13 | gi\|15226205 | SEQ ID NO: 14 | peroxidase | IPR002016 Haem peroxidase, plant/fungal/bacterial; IPR000823 Plant peroxidase |
| IMQ36.1 | At2g34400 | gi\|18403542 | SEQ ID NO: 15 | gi\|15226301 | SEQ ID NO: 16 | unknown protein | IPR002885 Pentatricopeptide repeat; IPR008940 Protein prenyltransferase |
| IMQ36.2 | At2g34410 | gi\|79324292 | SEQ ID NO: 17 | gi\|79324293 | SEQ ID NO: 18 | O-acetyltransferase | IPR012419 Cas1p-like |
| IMQ36.2 | At2g34410 | gi\|79324284 | SEQ ID NO: 19 | gi\|79324285 | SEQ ID NO: 20 | O-acetyltransferase | IPR012419 Cas1p-like |
| IMQ36.2 | At2g34410 | gi\|42569608 | SEQ ID NO: 21 | gi\|42569609 | SEQ ID NO: 22 | O-acetyltransferase | IPR012419 Cas1p-like |
| IMQ36.3 | At2g34420 | gi\|30686050 | SEQ ID NO: 23 | gi\|30686051 | SEQ ID NO: 24 | LHB1B2 | IPR001344 Chlorophyll A-B binding protein |
| IMQ36.3 | At2g34420 | gi\|30686047 | SEQ ID NO: 25 | gi\|18403546 | SEQ ID NO: 26 | LHB1B2 | IPR001344 Chlorophyll A-B binding protein |
| IMQ36.4 | At2g34430 | gi\|30686053 | SEQ ID NO: 27 | gi\|18403549 | SEQ ID NO: 28 | LHB1B1; chlorophyll binding | IPR001344 Chlorophyll A-B binding protein |
| IMQ36.5 | At2g34440 | gi\|18403551 | SEQ ID NO: 29 | gi\|15226309 | SEQ ID NO: 30 | transcription factor | IPR002100 Transcription factor, MADS-box |
| IMQ36.6 | At2g34450 | gi\|79324302 | SEQ ID NO: 31 | gi\|79324303 | SEQ ID NO: 32 | unknown protein | IPR000910 HMG1/2 (high mobility group) box |
| IMQ36.6 | At2g34450 | gi\|30686062 | SEQ ID NO: 33 | gi\|18403553 | SEQ ID NO: 34 | transcription factor | IPR000910 HMG1/2 (high mobility group) box |
| IMQ37.1 | At3g03800 | gi\|18396673 | SEQ ID NO: 35 | gi\|15228637 | SEQ ID NO: 36 | SYP131; t-SNARE | IPR000727 Target SNARE coiled-coil region; IPR006011 Syntaxin, N-terminal; IPR006012 Syntaxin/epimorphin family |
| IMQ37.2 | At3g03810 | gi\|30678945 | SEQ ID NO: 37 | gi\|30678946 | SEQ ID NO: 38 | unknown protein | IPR004348 Hypothetical plant protein |
| IMQ37.3 | At3g03820 | gi\|18396679 | SEQ ID NO: 39 | gi\|15228639 | SEQ ID NO: 40 | unknown protein | IPR003676 Auxin responsive SAUR protein |
| IMQ37.4 | At3g03830 | gi\|30678954 | SEQ ID NO: 41 | gi\|15228640 | SEQ ID NO: 42 | unknown protein | IPR003676 Auxin responsive SAUR protein |
| IMQ37.5 | At3g03840 | gi\|42563470 | SEQ ID NO: 43 | gi\|15228641 | SEQ ID NO: 44 | unknown protein | IPR003676 Auxin responsive SAUR protein |
| IMQ37.6 | At3g03847 | gi\|22330828 | SEQ ID NO: 45 | gi\|22330829 | SEQ ID NO: 46 | unknown protein | IPR003676 Auxin responsive SAUR protein |
| IMQ37.7 | At3g03850 | gi\|30678958 | SEQ ID NO: 47 | gi\|30678959 | SEQ ID NO: 48 | unknown protein | |
| IMQ38.1 | At3g07100 | gi\|30680128 | SEQ ID NO: 49 | gi\|30680129 | SEQ ID NO: 50 | protein binding/ transporter | IPR006896 Sec23/Sec24 trunk region; IPR006900 Sec23/Sec24 helical region; IPR006895 Zinc finger, Sec23/Sec24-type; IPR006706 Extensin-like region; IPR007123 Gelsolin region |
| IMQ38.2 | At3g07110 | gi\|79313148 | SEQ ID NO: 51 | gi\|79313149 | SEQ ID NO: 52 | structural constituent of ribosome | IPR005822 Ribosomal protein L13; IPR005755 Ribosomal protein L13, archea and eukaryotic form; IPR005823 Ribosomal protein L13, bacterial and organelle form |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ38.2 | At3g07110 | gi\|30680131 | SEQ ID NO: 53 | gi\|15231394 | SEQ ID NO: 54 | structural constituent of ribosome | IPR005822 Ribosomal protein L13; IPR005755 Ribosomal protein L13, archea and eukaryotic form; IPR005823 Ribosomal protein L13, bacterial and organelle form |
| IMQ38.3 | At3g07120 | gi\|30680134 | SEQ ID NO: 55 | gi\|15231396 | SEQ ID NO: 56 | protein binding/ ubiquitin-protein ligase/zinc ion binding | IPR001841 Zinc finger, RING-type |
| IMQ38.4 | At3g07130 | gi\|42563571 | SEQ ID NO: 57 | gi\|15231398 | SEQ ID NO: 58 | hydrolase/protein serine/threonine phosphatase | IPR004843 Metallophosphoesterase |
| IMQ38.5 | At3g07140 | gi\|42570456 | SEQ ID NO: 59 | gi\|30680143 | SEQ ID NO: 60 | GPI-anchor transamidase | IPR007245 Gpi16 subunit, GPI transamidase component |
| IMQ38.5 | At3g07140 | gi\|30680141 | SEQ ID NO: 61 | gi\|18397852 | SEQ ID NO: 62 | GPI-anchor transamidase | IPR007245 Gpi16 subunit, GPI transamidase component |
| IMQ38.6 | At3g07150 | gi\|18397855 | SEQ ID NO: 63 | gi\|15231401 | SEQ ID NO: 64 | unknown protein | |
| IMQ39.1 | At3g15480 | gi\|30683621 | SEQ ID NO: 65 | gi\|18400781 | SEQ ID NO: 66 | unknown protein | IPR009606 Protein of unknown function DUF1218 |
| IMQ39.2 | At3g15490 | gi\|42564187 | SEQ ID NO: 67 | gi\|42564188 | SEQ ID NO: 68 | unknown protein | IPR005061 Protein of unknown function DUF292, eukaryotic |
| IMQ39.3 | At3g15500 | gi\|30683631 | SEQ ID NO: 69 | gi\|15232604 | SEQ ID NO: 70 | ATNAC3; transcription factor | IPR003441 No apical meristem (NAM) protein |
| IMQ40.1 | At3g16580 | gi\|30684147 | SEQ ID NO: 71 | gi\|18401179 | SEQ ID NO: 72 | unknown protein | IPR001810 Cyclin-like F-box; IPR006527 F-box protein interaction domain |
| IMQ40.2 | At3g16590 | gi\|18401181 | SEQ ID NO: 73 | gi\|15228255 | SEQ ID NO: 74 | unknown protein | IPR006527 F-box protein interaction domain; IPR001810 Cyclin-like F-box |
| IMQ40.3 | At3g16600 | gi\|18401188 | SEQ ID NO: 75 | gi\|15228256 | SEQ ID NO: 76 | ATP binding/ATP-dependent helicase/ DNA binding/ helicase/nucleic acid binding/protein binding/ubiquitin-protein ligase/zinc ion binding | IPR000330 SNF2-related; IPR001410 DEAD/DEAH box helicase; IPR001650 Helicase, C-terminal |
| IMQ40.4 | At3g16610 | gi\|18401191 | SEQ ID NO: 77 | gi\|15228257 | SEQ ID NO: 78 | unknown protein | IPR001841 Zinc finger, RING-type; IPR002885 Pentatricopeptide repeat |
| IMQ40.5 | At3g16620 | gi\|30684161 | SEQ ID NO: 79 | gi\|15228272 | SEQ ID NO: 80 | ATTOC120; protein translocase | IPR006703 AIG1; IPR002917 GTP-binding protein, HSR1-related; IPR005688 Chloroplast protein import component Toc34; IPR005690 Chloroplast protein import component Toc86/159 |
| IMQ41.1 | At3g17640 | gi\|18401587 | SEQ ID NO: 81 | gi\|15229088 | SEQ ID NO: 82 | protein binding | IPR001611 Leucine-rich repeat; IPR007090 Leucine-rich repeat, plant specific |
| IMQ41.2 | At3g17650 | gi\|18401589 | SEQ ID NO: 83 | gi\|18401590 | SEQ ID NO: 84 | PDE321; oligopeptide transporter | IPR004813 Oligopeptide transporter OPT superfamily; IPR004814 Oligopeptide transporter OPT; IPR004648 Tetrapeptide transporter, OPT1/isp4 |
| IMQ41.3 | At3g17660 | gi\|18401594 | SEQ ID NO: 85 | gi\|15229090 | SEQ ID NO: 86 | DNA binding | IPR001164 Arf GTPase activating protein |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ41.4 | At3g17670 | gi\|18401598 | SEQ ID NO: 87 | gi\|15229091 | SEQ ID NO: 88 | unknown protein | IPR001440 TPR repeat |
| IMQ41.5 | At3g17680 | gi\|79313276 | SEQ ID NO: 89 | gi\|79313277 | SEQ ID NO: 90 | unknown protein | IPR011684 KIP1-like |
| IMQ41.5 | At3g17680 | gi\|30684630 | SEQ ID NO: 91 | gi\|30684631 | SEQ ID NO: 92 | unknown protein | IPR011684 KIP1-like |
| IMQ41.6 | At3g17690 | gi\|30684635 | SEQ ID NO: 93 | gi\|15229093 | SEQ ID NO: 94 | ATCNGC19; calmodulin binding/ cyclic nucleotide binding/ion channel | IPR005821 Ion transport protein; IPR000595 Cyclic nucleotide-binding |
| IMQ42.1 | At3g19850 | gi\|42565033 | SEQ ID NO: 95 | gi\|42565034 | SEQ ID NO: 96 | protein binding/ signal transducer | IPR004249 NPH3; IPR000210 BTB/POZ |
| IMQ42.2 | At3g19860 | gi\|79313298 | SEQ ID NO: 97 | gi\|79313299 | SEQ ID NO: 98 | DNA binding | IPR001092 Basic helix-loop-helix dimerisation region bHLH; IPR003106 Leucine zipper, homeobox-associated |
| IMQ42.2 | At3g19860 | gi\|30685522 | SEQ ID NO: 99 | gi\|15230975 | SEQ ID NO: 100 | DNA binding/ transcription factor | IPR001092 Basic helix-loop-helix dimerisation region bHLH; IPR003106 Leucine zipper, homeobox-associated |

TABLE 3

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ34.3 | At2g31480 | gi\|42569515 | gi\|42569516 | | | |
| IMQ34.4 | At2g31490 | gi\|18402681 | gi\|18402682 | gi\|15146360 | gi\|57899156 | *Oryza sativa* (*japonica* cultivar-group) |
| | | | | gi\|34910867 | gi\|34910868 | *Oryza sativa* (*japonica* cultivar-group) |
| | | | | gi\|34909561 | gi\|34909562 | *Oryza sativa* (*japonica* cultivar-group) |
| IMQ35.1 | At2g34030 | gi\|42569600 | gi\|42569601 | gi\|30690570 | gi\|15218787 | *Arabidopsis thaliana* |
| | | | | gi\|18403422 | gi\|15226191 | *Arabidopsis thaliana* |
| | | | | gi\|30695447 | gi\|30695448 | *Arabidopsis thaliana* |
| IMQ35.2 | At2g34040 | gi\|30685905 | gi\|30685906 | gi\|30685899 | gi\|18403429 | *Arabidopsis thaliana* |
| | | | | gi\|42562386 | gi\|42562387 | *Arabidopsis thaliana* |
| | | | | gi\|50907460 | gi\|50907461 | *Oryza sativa* (*japonica* cultivar-group) |
| | | | | gi\|66526466 | gi\|66526467 | *Apis mellifera* |
| IMQ35.2 | At2g34040 | gi\|30685899 | gi\|18403429 | gi\|30685905 | gi\|30685906 | *Arabidopsis thaliana* |
| | | | | gi\|42562386 | gi\|42562387 | *Arabidopsis thaliana* |
| | | | | gi\|50907460 | gi\|50907461 | *Oryza sativa* (*japonica* cultivar-group) |
| | | | | gi\|66526466 | gi\|66526467 | *Apis mellifera* |
| IMQ35.3 | At2g34050 | gi\|30685908 | gi\|18403431 | gi\|50907446 | gi\|50907447 | *Oryza sativa* (*japonica* cultivar-group) |
| | | | | gi\|66814293 | gi\|66814294 | *Dictyostelium discoideum* |
| | | | | gi\|50751555 | gi\|50751556 | *Gallus gallus* |
| IMQ35.4 | At2g34060 | gi\|30685912 | gi\|15226205 | gi\|50918940 | gi\|50918941 | *Oryza sativa* (*japonica* cultivar-group) |
| | | | | gi\|55701112 | gi\|55701113 | *Oryza sativa* (*japonica* cultivar-group) |
| | | | | gi\|537318 | gi\|537319 | *Medicago sativa* |
| IMQ36.1 | At2g34400 | gi\|18403542 | gi\|15226301 | gi\|18398256 | gi\|15231970 | *Arabidopsis thaliana* |
| | | | | gi\|18399739 | gi\|15230593 | *Arabidopsis thaliana* |
| | | | | gi\|18420159 | gi\|15233645 | *Arabidopsis thaliana* |
| IMQ36.2 | At2g34410 | gi\|79324292 | gi\|79324293 | gi\|79324284 | gi\|79324285 | *Arabidopsis thaliana* |
| | | | | gi\|42569608 | gi\|42569609 | *Arabidopsis thaliana* |
| | | | | gi\|30694937 | gi\|18422663 | *Arabidopsis thaliana* |
| | | | | gi\|42562401 | gi\|42562402 | *Arabidopsis thaliana* |
| | | | | gi\|20161482 | gi\|55297065 | *Oryza sativa* (*japonica* cultivar-group) |
| IMQ36.2 | At2g34410 | gi\|79324284 | gi\|79324285 | gi\|79324292 | gi\|79324293 | *Arabidopsis thaliana* |
| | | | | gi\|42569608 | gi\|42569609 | *Arabidopsis thaliana* |
| | | | | gi\|30694937 | gi\|18422663 | *Arabidopsis thaliana* |
| | | | | gi\|42562401 | gi\|42562402 | *Arabidopsis thaliana* |
| | | | | gi\|20161482 | gi\|55297065 | *Oryza sativa* (*japonica* cultivar-group) |
| IMQ36.2 | At2g34410 | gi\|42569608 | gi\|42569609 | gi\|79324292 | gi\|79324293 | *Arabidopsis thaliana* |
| | | | | gi\|79324284 | gi\|79324285 | *Arabidopsis thaliana* |
| | | | | gi\|30694937 | gi\|18422663 | *Arabidopsis thaliana* |
| | | | | gi\|42562401 | gi\|42562402 | *Arabidopsis thaliana* |
| | | | | gi\|20161482 | gi\|55297065 | *Oryza sativa* (*japonica* cultivar-group) |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ36.3 | At2g34420 | gi\|30686050 | gi\|30686051 | gi\|30686047 | gi\|18403546 | *Arabidopsis thaliana* |
| | | | | gi\|30690951 | gi\|15220615 | *Arabidopsis thaliana* |
| | | | | gi\|30690948 | gi\|18397288 | *Arabidopsis thaliana* |
| | | | | gi\|30690947 | gi\|18397286 | *Arabidopsis thaliana* |
| IMQ36.3 | At2g34420 | gi\|30686047 | gi\|18403546 | gi\|30690951 | gi\|15220615 | *Arabidopsis thaliana* |
| | | | | gi\|30690948 | gi\|18397288 | *Arabidopsis thaliana* |
| | | | | gi\|30690947 | gi\|18397286 | *Arabidopsis thaliana* |
| | | | | gi\|31323255 | gi\|31323256 | *Brassica oleracea* |
| IMQ36.4 | At2g34430 | gi\|30686053 | gi\|18403549 | gi\|21137 | gi\|21138 | *Sinapis alba* |
| | | | | gi\|18266038 | gi\|18266039 | *Brassica oleracea* |
| | | | | gi\|30690951 | gi\|15220615 | *Arabidopsis thaliana* |
| IMQ36.5 | At2g34440 | gi\|18403551 | gi\|15226309 | gi\|18397662 | gi\|15230767 | *Arabidopsis thaliana* |
| | | | | gi\|30682570 | gi\|30682571 | *Arabidopsis thaliana* |
| | | | | gi\|18424355 | gi\|15239333 | *Arabidopsis thaliana* |
| IMQ36.6 | At2g34450 | gi\|79324302 | gi\|79324303 | gi\|30686062 | gi\|18403553 | *Arabidopsis thaliana* |
| | | | | gi\|20161570 | gi\|56202161 | *Oryza sativa* (*japonica* cultivar-group) |
| | | | | gi\|63020535 | gi\|63020536 | *Cucumis sativus* |
| | | | | gi\|34910913 | gi\|34910914 | *Oryza sativa* (*japonica* cultivar-group) |
| IMQ36.6 | At2g34450 | gi\|30686062 | gi\|18403553 | gi\|20161570 | gi\|56202161 | *Oryza sativa* (*japonica* cultivar-group) |
| | | | | gi\|63020535 | gi\|63020536 | *Cucumis sativus* |
| | | | | gi\|42562198 | gi\|18394900 | *Arabidopsis thaliana* |
| IMQ37.1 | At3g03800 | gi\|18396673 | gi\|15228637 | gi\|18415700 | gi\|18415701 | *Arabidopsis thaliana* |
| | | | | gi\|51963279 | gi\|51963280 | *Oryza sativa* (*japonica* cultivar-group) |
| | | | | gi\|50934370 | gi\|50934371 | *Oryza sativa* (*japonica* cultivar-group) |
| | | | | gi\|55741415 | gi\|55741416 | *Oryza sativa* (*japonica* cultivar-group) |
| IMQ37.2 | At3g03810 | gi\|30678945 | gi\|30678946 | gi\|46063406 | gi\|50878393 | *Oryza sativa* (*japonica* cultivar-group) |
| | | | | gi\|30689847 | gi\|30689848 | *Arabidopsis thaliana* |
| | | | | gi\|30679041 | gi\|22329335 | *Arabidopsis thaliana* |
| IMQ37.3 | At3g03820 | gi\|18396679 | gi\|15228639 | gi\|42563470 | gi\|15228641 | *Arabidopsis thaliana* |
| | | | | gi\|30678958 | gi\|30678959 | *Arabidopsis thaliana* |
| | | | | gi\|30678954 | gi\|15228640 | *Arabidopsis thaliana* |
| IMQ37.4 | At3g03830 | gi\|30678954 | gi\|15228640 | gi\|30678958 | gi\|30678959 | *Arabidopsis thaliana* |
| | | | | gi\|18396679 | gi\|15228639 | *Arabidopsis thaliana* |
| | | | | gi\|42563470 | gi\|15228641 | *Arabidopsis thaliana* |
| IMQ37.5 | At3g03840 | gi\|42563470 | gi\|15228641 | gi\|18396679 | gi\|15228639 | *Arabidopsis thaliana* |
| | | | | gi\|30678958 | gi\|30678959 | *Arabidopsis thaliana* |
| | | | | gi\|30678954 | gi\|15228640 | *Arabidopsis thaliana* |
| IMQ37.6 | At3g03847 | gi\|22330828 | gi\|22330829 | gi\|42567926 | gi\|15238721 | *Arabidopsis thaliana* |
| | | | | gi\|42567924 | gi\|15238716 | *Arabidopsis thaliana* |
| | | | | gi\|30686621 | gi\|15238715 | *Arabidopsis thaliana* |
| IMQ37.7 | At3g03850 | gi\|30678958 | gi\|30678959 | gi\|30678954 | gi\|15228640 | *Arabidopsis thaliana* |
| | | | | gi\|42563470 | gi\|15228641 | *Arabidopsis thaliana* |
| | | | | gi\|18396679 | gi\|15228639 | *Arabidopsis thaliana* |
| IMQ38.1 | At3g07100 | gi\|30680128 | gi\|30680129 | gi\|50921574 | gi\|50921575 | *Oryza sativa* (*japonica* cultivar-group) |
| | | | | gi\|74199102 | gi\|74199103 | *Mus musculus* |
| | | | | gi\|31340743 | gi\|30424898 | *Mus musculus* |
| IMQ38.2 | At3g07110 | gi\|79313148 | gi\|79313149 | gi\|30680131 | gi\|15231394 | *Arabidopsis thaliana* |
| | | | | gi\|30695535 | gi\|15239698 | *Arabidopsis thaliana* |
| | | | | gi\|30687674 | gi\|15230197 | *Arabidopsis thaliana* |
| | | | | gi\|42566745 | gi\|15235617 | *Arabidopsis thaliana* |
| IMQ38.2 | At3g07110 | gi\|30680131 | gi\|15231394 | gi\|30695535 | gi\|15239698 | *Arabidopsis thaliana* |
| | | | | gi\|30687674 | gi\|15230197 | *Arabidopsis thaliana* |
| | | | | gi\|42566745 | gi\|15235617 | *Arabidopsis thaliana* |
| IMQ38.3 | At3g07120 | gi\|30680134 | gi\|15231396 | gi\|42565172 | gi\|15230243 | *Arabidopsis thaliana* |
| | | | | gi\|42570141 | gi\|42570142 | *Arabidopsis thaliana* |
| | | | | gi\|18413925 | gi\|15235589 | *Arabidopsis thaliana* |
| IMQ38.4 | At3g07130 | gi\|42563571 | gi\|15231398 | gi\|13925770 | gi\|13925771 | *Glycine max* |
| | | | | gi\|62177682 | gi\|62177683 | *Medicago truncatula* |
| | | | | gi\|50920094 | gi\|50920095 | *Oryza sativa* (*japonica* cultivar-group) |
| IMQ38.5 | At3g07140 | gi\|42570456 | gi\|30680143 | gi\|30680141 | gi\|18397852 | *Arabidopsis thaliana* |
| | | | | gi\|77548247 | gi\|77550830 | *Oryza sativa* (*japonica* cultivar-group) |
| | | | | gi\|73992512 | gi\|73992513 | *Canis familiaris* |
| IMQ38.5 | At3g07140 | gi\|30680141 | gi\|18397852 | gi\|42570456 | gi\|30680143 | *Arabidopsis thaliana* |
| | | | | gi\|77548247 | gi\|77550830 | *Oryza sativa* (*japonica* cultivar-group) |
| | | | | gi\|73992512 | gi\|73992513 | *Canis familiaris* |
| IMQ38.6 | At3g07150 | gi\|18397855 | gi\|15231401 | gi\|19386744 | gi\|57900451 | *Oryza sativa* (*japonica* cultivar-group) |
| | | | | gi\|34907011 | gi\|34907012 | *Oryza sativa* (*japonica* cultivar-group) |
| IMQ39.1 | At3g15480 | gi\|30683621 | gi\|18400781 | gi\|42562716 | gi\|18404242 | *Arabidopsis thaliana* |
| | | | | gi\|38016520 | gi\|38016521 | *Gossypium barbadense* |
| | | | | gi\|50936920 | gi\|50936921 | *Oryza sativa* (*japonica* cultivar-group) |
| IMQ39.2 | At3g15490 | gi\|42564187 | gi\|42564188 | gi\|18397647 | gi\|15226014 | *Arabidopsis thaliana* |
| | | | | gi\|50918206 | gi\|50918207 | *Oryza sativa* (*japonica* cultivar-group) |
| | | | | gi\|30683233 | gi\|15222251 | *Arabidopsis thaliana* |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ39.3 | At3g15500 | gi\|30683631 | gi\|15232604 | gi\|42562715 | gi\|15219112 | *Arabidopsis thaliana* |
| | | | | gi\|66394515 | gi\|66394516 | *Glycine max* |
| | | | | gi\|6175245 | gi\|6175246 | *Lycopersicon esculentum* |
| IMQ40.1 | At3g16580 | gi\|30684147 | gi\|18401179 | gi\|42569040 | gi\|15225992 | *Arabidopsis thaliana* |
| | | | | gi\|18398432 | gi\|15223198 | *Arabidopsis thaliana* |
| | | | | gi\|18401705 | gi\|18401706 | *Arabidopsis thaliana* |
| IMQ40.2 | At3g16590 | gi\|18401181 | gi\|15228255 | gi\|18391359 | gi\|15221240 | *Arabidopsis thaliana* |
| | | | | gi\|30684644 | gi\|18401609 | *Arabidopsis thaliana* |
| | | | | gi\|18391361 | gi\|15221246 | *Arabidopsis thaliana* |
| IMQ40.3 | At3g16600 | gi\|18401188 | gi\|15228256 | gi\|18403060 | gi\|18403061 | *Arabidopsis thaliana* |
| | | | | gi\|18402451 | gi\|15231009 | *Arabidopsis thaliana* |
| | | | | gi\|51964729 | gi\|51964730 | *Oryza sativa* (*japonica* cultivar-group) |
| IMQ40.4 | At3g16610 | gi\|18401191 | gi\|15228257 | gi\|50941690 | gi\|50941691 | *Oryza sativa* (*japonica* cultivar-group) |
| | | | | gi\|18483227 | gi\|18483237 | *Sorghum bicolor* |
| | | | | gi\|34906109 | gi\|34906110 | *Oryza sativa* (*japonica* cultivar-group) |
| | | | | gi\|28564706 | gi\|57899529 | *Oryza sativa* (*japonica* cultivar-group) |
| IMQ40.5 | At3g16620 | gi\|30684161 | gi\|15228272 | gi\|30679717 | gi\|15227268 | *Arabidopsis thaliana* |
| | | | | gi\|37536637 | gi\|37536638 | *Oryza sativa* (*japonica* cultivar-group) |
| | | | | gi\|44662984 | gi\|44662985 | *Physcomitrella patens* |
| IMQ41.1 | At3g17640 | gi\|18401587 | gi\|15229088 | gi\|50931366 | gi\|50931367 | *Oryza sativa* (*japonica* cultivar-group) |
| | | | | gi\|51339056 | gi\|55733924 | *Oryza sativa* (*japonica* cultivar-group) |
| | | | | gi\|30678565 | gi\|30678566 | *Arabidopsis thaliana* |
| IMQ41.2 | At3g17650 | gi\|18401589 | gi\|18401590 | gi\|30694308 | gi\|18402162 | *Arabidopsis thaliana* |
| | | | | gi\|42562981 | gi\|15218799 | *Arabidopsis thaliana* |
| | | | | gi\|74267415 | gi\|74267416 | *Oryza sativa* (*japonica* cultivar-group) |
| IMQ41.3 | At3g17660 | gi\|18401594 | gi\|15229090 | gi\|30696440 | gi\|18423615 | *Arabidopsis thaliana* |
| | | | | gi\|50510177 | gi\|50510178 | *Oryza sativa* (*japonica* cultivar-group) |
| | | | | gi\|60596222 | gi\|76152990 | *Schistosoma japonicum* |
| IMQ41.4 | At3g17670 | gi\|18401598 | gi\|15229091 | gi\|53749471 | gi\|53749491 | *Solanum demissum* |
| | | | | gi\|50929586 | gi\|50929587 | *Oryza sativa* (*japonica* cultivar-group) |
| | | | | gi\|50928358 | gi\|50928359 | *Oryza sativa* (*japonica* cultivar-group) |
| IMQ41.5 | At3g17680 | gi\|79313276 | gi\|79313277 | gi\|30684630 | gi\|30684631 | *Arabidopsis thaliana* |
| | | | | gi\|22330106 | gi\|22330107 | *Arabidopsis thaliana* |
| | | | | gi\|53749471 | gi\|53749473 | *Solanum demissum* |
| | | | | gi\|50916296 | gi\|50916297 | *Oryza sativa* (*japonica* cultivar-group) |
| IMQ41.5 | At3g17680 | gi\|30684630 | gi\|30684631 | gi\|22330106 | gi\|22330107 | *Arabidopsis thaliana* |
| | | | | gi\|53749471 | gi\|53749473 | *Solanum demissum* |
| | | | | gi\|50916296 | gi\|50916297 | *Oryza sativa* (*japonica* cultivar-group) |
| IMQ41.6 | At3g17690 | gi\|30684635 | gi\|15229093 | gi\|42564623 | gi\|18401606 | *Arabidopsis thaliana* |
| | | | | gi\|50913256 | gi\|50913257 | *Oryza sativa* (*japonica* cultivar-group) |
| | | | | gi\|51091189 | gi\|51091194 | *Oryza sativa* (*japonica* cultivar-group) |
| IMQ42.1 | At3g19850 | gi\|42565033 | gi\|42565034 | gi\|22330149 | gi\|22330150 | *Arabidopsis thaliana* |
| | | | | gi\|50929590 | gi\|50929591 | *Oryza sativa* (*japonica* cultivar-group) |
| | | | | gi\|50938220 | gi\|50938221 | *Oryza sativa* (*japonica* cultivar-group) |
| IMQ42.2 | At3g19860 | gi\|79313298 | gi\|79313299 | gi\|30685522 | gi\|15230975 | *Arabidopsis thaliana* |
| | | | | gi\|51536177 | gi\|51536178 | *Oryza sativa* (*japonica* cultivar-group) |
| | | | | gi\|30690567 | gi\|30690568 | *Arabidopsis thaliana* |
| | | | | gi\|22329203 | gi\|22329204 | *Arabidopsis thaliana* |
| IMQ42.2 | At3g19860 | gi\|30685522 | gi\|15230975 | gi\|51536177 | gi\|51536178 | *Oryza sativa* (*japonica* cultivar-group) |
| | | | | gi\|22329203 | gi\|22329204 | *Arabidopsis thaliana* |
| | | | | gi\|30690567 | gi\|30690568 | *Arabidopsis thaliana* |

Example 2

Analysis of the *Arabidopsis* IMO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318), PSORT (Nakai K, and Horton P, 1999, *Trends Biochem. Sci.* 24:34-6), and/or CLUSTAL (Thompson J D et al., 1994, *Nucleic Acids Res.* 22:4673-4680). Conserved domains for each protein are listed in column 8 of Table 2.

Example 3

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value≦0.05. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

medium for 3 days. Following co-cultivation, the segments are placed on K1D1TC (callus induction medium containing 250 mg/l Carbenicillin and 300 mg/l Timentin) for one week of recovery. Alternately, the segments are placed directly on selection medium K1D1H1 (above medium with 1 mg/l selection agent, for example an herbicide). Carbenicillin and Timentin are antibiotics used to kill the *Agrobacterium*. The selection agent is used to allow the growth of the transformed cells.

Callus samples from independent events are tested by PCR. All the samples tested are positive for the presence of the transformed gene, whereas the non-transformed controls are negative. Callus samples are confirmed to express the appropriate protein as determined by ELISA.

TABLE 4

| 1. Gene | 2. TAIR | 3. Construct | 4. ANOVA Protein | 5. ANOVA Oil | 6. ANOVA Digestible Protein | 7. ANOVA Fiber | 8. Protein | 9. Oil | 10. Digestible Protein | 11. Fiber |
|---------|---------|--------------|------------------|--------------|-----------------------------|----------------|------------|--------|------------------------|-----------|
| IMQ37.5 | At3g03840 | CsVMV::At3g03840 | 0.433 | 0.415 | 0.033 | 0.197 | 101.7% | 98.7% | 102.4% | 98.7% |
| IMQ37.6 | At3g03847 | CsVMV::At3g03847 | 0.998 | 0.503 | 0.634 | 0.864 | 100.2% | 99.4% | 100.5% | 99.8% |
| IMQ37.6 | At3g03847 | Pru::At3g03847 | 0.007 | 0.002 | 0.115 | 0.547 | 104.6% | 94.4% | 101.2% | 100.6% |
| IMQ39.1 | At3g15480 | Pru::At3g15480 | 0.521 | 0.450 | 0.026 | 0.011 | 100.9% | 100.4% | 101.4% | 97.6% |
| IMQ39.2 | At3g15490 | CsVMV::At3g15490 | 0.192 | 0.463 | 0.176 | 0.035 | 103.1% | 99.1% | 101.7% | 97.8% |
| IMQ39.2 | At3g15490 | Pru::At3g15490 | 0.125 | 0.551 | <0.0001 | <0.0001 | 100.9% | 99.4% | 101.4% | 97.8% |
| IMQ40.1 | At3g16580 | CsVMV::At3g16580 | 0.436 | 0.321 | 0.050 | 0.173 | 101.3% | 99.0% | 101.6% | 98.9% |
| IMQ40.1 | At3g16580 | Pru::At3g16580 | 0.269 | 0.972 | 0.005 | 0.003 | 101.3% | 99.7% | 101.7% | 97.4% |
| IMQ40.3 | At3g16600 | Pru::At3g16600 | 0.019 | 0.019 | 0.220 | 0.136 | 102.8% | 97.0% | 99.5% | 101.5% |
| IMQ41.1 | At3g17640 | CsVMV::At3g17640 | 0.991 | 0.671 | 0.864 | 0.725 | 99.9% | 99.5% | 99.8% | 99.8% |
| IMQ41.1 | At3g17640 | Pru::At3g17640 | 0.024 | 0.006 | 0.041 | 0.003 | 97.1% | 105.0% | 101.3% | 96.8% |
| IMQ41.5 | At3g17680 | CsVMV::At3g17680 | 0.567 | 0.873 | 0.803 | 0.290 | 101.3% | 100.2% | 100.3% | 98.9% |
| IMQ41.5 | At3g17680 | Pru::At3g17680 | 0.569 | 0.252 | 0.009 | 0.004 | 99.3% | 101.8% | 102.1% | 96.7% |
| IMQ41.6 | At3g17690 | CsVMV::At3g17690 | 0.388 | 0.856 | 0.060 | 0.039 | 102.7% | 99.8% | 102.4% | 97.3% |
| IMQ41.6 | At3g17690 | Pru::At3g17690 | 0.263 | 0.726 | 0.003 | 0.009 | 102.0% | 99.2% | 103.0% | 96.5% |

Example 4

To test whether over-expression of the genes identified in Tables 1-4 alter the seed composition phenotype, protein, digestible protein, oil, and fiber content in seeds from transgenic plants expressing these genes is compared with protein, digestible protein, oil and fiber content in seeds from non-transgenic control plants. Any one of the genes identified in Tables 1-4 is used to transform *Brassica napus* (canola). To do this, the genes are cloned into plant transformation vectors behind the strong constitutive CsVMV promoter and the seed specific phaseolin promoter. These constructs (which include a gene encoding a selection agent) are transformed into canola plants.

Transformation of canola is accomplished via *Agrobacterium*-mediated transformation. Seeds are surface-sterilized with 10% commercial bleach for 10 minutes and rinsed 3 times with sterile distilled water. The seeds are then placed on one half concentration of MS basal medium (Murashige and Skoog, *Physiol. Plant.* 15:473-497, 1962) and maintained under growth regime set at 25° C., and a photoperiod of 16 hrs light/8 hrs dark.

Hypocotyl segments (3-5 mm) are excised from 5-7 day old seedlings and placed on callus induction medium K1D1 (MS medium with 1 mg/l kinetin and 1 mg/l 2,4-D) for 3 days as pre-treatment. The segments are then transferred into a petri plate, treated with *Agrobacterium* Z7075 or LBA4404 strain containing pDAB721. The *Agrobacterium* is grown overnight at 28° C. in the dark on a shaker at 150 rpm and subsequently re-suspended in the culture medium.

After 30 minute treatment of the hypocotyl segments with *Agrobacterium*, these are placed back on the callus induction Callused hypocotyl segments are then placed on B3Z1H1 (MS medium, 3 mg/l benzylamino purine, 1 mg/l Zeatin, 0.5 gm/l MES [2-(N-morpholino) ethane sulfonic acid], 5 mg/l silver nitrate, 1 mg/l selection agent, Carbenicillin and Timentin) shoot regeneration medium. After shoots start to regenerate (approximately 3 weeks), hypocotyl segments along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, 3 mg/l selection agent, Carbenicillin and Timentin) for 3 weeks.

Shoots are excised from the hypocotyl segments and transferred to shoot elongation medium MESH10 (MS, 0.5 gm/l MES, 10 mg/l selection agent, Carbenicillin, Timentin) for 2-4 weeks. The elongated shoots are cultured for root induction on MSI.1 (MS with 0.1 mg/l Indolebutyric acid). Once the plants have a well established root system, these are transplanted into soil. The plants are acclimated under controlled environmental conditions in the Conviron for 1-2 weeks before transfer to the greenhouse. The transformed T0 plants self-pollinate in the greenhouse to obtain T1 seed. Transgenic plants are selected at the T1 generation based on resistance to a selection agent. T2 seed (from T1 plants) is harvested and sown in soil. T2 plants are grown to maturity, allowed to self-fertilize and set seed. T3 seed (from the T2 plants) is harvested in bulk for each line. Seed oil, protein, digestible protein, and fiber values are measured as discussed in Example 1.

It is claimed:

1. A method of producing meal, comprising:
   growing a transgenic plant comprising a plant transformation vector comprising a nucleotide sequence that encodes or is the complement of a sequence that encodes an IMQ polypeptide comprising the amino acid sequence as set forth in SEQ ID NO: 76, whereby the transgenic plant has an improved meal quality phenotype, relative to control plants; and
   recovering meal from the transgenic plant, thereby producing meal.

2. The method of claim 1, wherein the meal is produced from seeds of the transgenic plant.

3. A method of producing an improved meal quality phenotype in a plant, said method comprising:
   a) introducing into progenitor cells of the plant a plant transformation vector comprising a nucleotide sequence that encodes or is the compliment of a sequence that encodes an IMQ polypeptide comprising the amino acid sequence set forth in SEQ ID NO: 76,
   b) growing the transformed progenitor cells to produce a transgenic plant, wherein the nucleotide sequence is expressed, and the transgenic plant exhibits an improved meal quality phenotype relative to control plants, and
   c) recovering meal from the transgenic plant, thereby producing the improved meal quality phenotype in the plant.

4. A method of generating a plant having an improved meal quality phenotype, comprising:
   a) identifying a plant that has an allele in its ortholog of the *A. thaliana* IMQ gene where the wildtype *A. thaliana* gene has the nucleic acid sequence set forth as SEQ ID NO: 75, which allele results in improved meal quality phenotype, compared to a control plant lacking the allele, wherein identifying a plant comprises analyzing the sequence of the allele in the plant;
   b) generating progeny of said identified plant; and
   c) identifying from among the progeny at least one plant that inherits the allele and has an improved meal quality phenotype relative to the control plant lacking the allele, thereby generating a plant having an improved meal quality phenotype.

5. The method of claim 4 that employs candidate gene/QTL methodology.

6. The method of claim 4 that employs TILLING methodology.

* * * * *

SEQUENCE LISTING

<160> NUMBER OF SEQ ID NOS: 100

<210> SEQ ID NO 1
<211> LENGTH: 2022
<212> TYPE: DNA
<213> ORGANISM: Arabidopsis thaliana

<400> SEQUENCE: 1

```
aatcaaacca acattgtat tttggctctg aagattgaag gagctaaact gaaactgcaa      60
tatatatggc ttctacaggt ggtgggaaag atggatctaa aggttttgtg aagagggtta    120
catcaacttt ctccattagg aaaaagaaga acacaacaag tgatccaaaa ctacttcttc    180
ctcgatcgaa atcaaccggt gctaactatg aatctatgag gctacctcag gggaaaaagg    240
ctcttccaga tgttgttaca acaaaagaca caaagagaac caaatctgca ggtgtttcgc    300
cacaaccaag acgtgaaaag attgatgaat ccggtaaaca gtttatgaag gtgagatgtt    360
ttgatgacag tgactccatt tggttatctt cagattgtgc ctctcctacg tctcttttag    420
aggaacgtag attatctgtc tcgtttcatt tctcagtaga cgaaaagatc gtctcgtggt    480
tgtccagtgt ggctaactct tctctgtctt taaatcaaga atccaccagc tcaaacaaag    540
agaatcatca tcaaaaaagt tcaaagaaca caaaaacttc tttagaaaac gttcgaaaag    600
atggaaaagt ttgcaactca tcagctggga agctcgtgg tactggttct gcaaagccgt    660
ctttaccaga aagcaacaac aagacttgtc ctcagaaaca atgtgaagag tcatctattt    720
ccaacagatt tgtgactctt gaagaaaaga agttagctt ctcagtagca aaaacagaga    780
agtctccttc accagataac tcaactgcca ctgcgacatc atcattaaag aagagtgcag    840
agattggggt cacaaagagt aagattgttg tggagccact ttttttggcca tttgagcaga    900
agtttgattg gacaccagag gatattttaa agcatttttc aatgtctccg aggagaaaga    960
agtcgctagg atccaagatt gcaggtacct ctccaagatc aatgagggca caactccaaa   1020
caagaaagct agatctaaaa gaagggtgta agagaaagct catgttcaac ggtcctggat   1080
caaattcaaa accaacaaga atcccagaac taaacagaac aatcagcaat agcagcaaca   1140
atagtagcat gaagaaaacc gagatcagca agaaccaaca acctataagg aacagtgtga   1200
agagaaacaa aagtttaccg tcgaggttga gaaaatcgag caaatatctc tcaaaggtgg   1260
tacctattga agctgcggaa gagagtggag aaatagttaa agagcaaaaa acacctaaga   1320
agctcatcat gacccgcaag tccaggacat tcttagaaga tgactttgct ttaatgaatg   1380
atttctctat agaaaaggcg gtcgggcttt gcgagtttaa gggaagagaa ggcatagatt   1440
cagatttcaa cactgatggt ttcttgttcg acgattctct atgaaaagaa aaggctttac   1500
aggttcgata cggacgtcat agattcacca ccttctcgcg tcgtcacaac agagataccat   1560
cctgctcgcg atccgacgac accaccagca ccaccgccgg agtggttaat gagagagatg   1620
gcgaaggaaa acggctataa ccctaggctg atcatgtcta ggactctgac gaagaacgat   1680
gtaagcaaaa ggcaggcatg tctcttgatt cttgggaaac ttgaaggatc agaatttctt   1740
ggaagacaag gaagctttat tgttggaaac acaatccttg atgactgatg ctcgagcggt   1800
tcgtgagtgt cttttttgga tccgctgtaa gtgaagtcta tttgaaaaaa acggaaaacc   1860
acattgatct gtggtgtata tggggttatg ttctatttga aaggagtctt tttctctttg   1920
ttgttttcat atttcataag atcaagctat gcttcaaagc agagggatgg attgttcttg   1980
tttcaattct gatcattttt ttttgctaca cctaggaaag at                       2022
```

```
<210> SEQ ID NO 2
<211> LENGTH: 472
<212> TYPE: PRT
<213> ORGANISM: Arabidopsis thaliana

<400> SEQUENCE: 2

Met Ala Ser Thr Gly Gly Gly Lys Asp Gly Ser Lys Gly Phe Val Lys
1               5                   10                  15

Arg Val Thr Ser Thr Phe Ser Ile Arg Lys Lys Lys Asn Thr Thr Ser
            20                  25                  30

Asp Pro Lys Leu Leu Leu Pro Arg Ser Lys Ser Thr Gly Ala Asn Tyr
        35                  40                  45

Glu Ser Met Arg Leu Pro Gln Gly Lys Lys Ala Leu Pro Asp Val Val
    50                  55                  60

Thr Thr Lys Asp Thr Lys Arg Thr Lys Ser Ala Gly Val Ser Pro Gln
65                  70                  75                  80

Pro Arg Arg Glu Lys Ile Asp Glu Ser Gly Lys Gln Phe Met Lys Val
                85                  90                  95

Arg Cys Phe Asp Asp Ser Asp Ser Ile Trp Leu Ser Ser Asp Cys Ala
            100                 105                 110

Ser Pro Thr Ser Leu Leu Glu Glu Arg Arg Leu Ser Val Ser Phe His
        115                 120                 125

Phe Ser Val Asp Glu Lys Ile Val Ser Trp Leu Ser Ser Val Ala Asn
    130                 135                 140

Ser Ser Leu Ser Leu Asn Gln Glu Ser Thr Ser Ser Asn Lys Glu Asn
145                 150                 155                 160

His His Gln Lys Ser Ser Lys Asn Thr Lys Thr Ser Leu Glu Asn Val
                165                 170                 175

Arg Lys Asp Gly Lys Val Cys Asn Ser Ser Ala Gly Lys Ala Arg Gly
            180                 185                 190

Thr Gly Ser Ala Lys Pro Ser Leu Pro Glu Ser Asn Asn Lys Thr Cys
        195                 200                 205

Pro Gln Lys Gln Cys Glu Glu Ser Ser Ile Ser Asn Arg Phe Val Thr
    210                 215                 220

Leu Glu Glu Lys Lys Val Ser Phe Ser Val Ala Lys Thr Glu Lys Ser
225                 230                 235                 240

Pro Ser Pro Asp Asn Ser Thr Ala Thr Ala Thr Ser Ser Leu Lys Lys
                245                 250                 255

Ser Ala Glu Ile Gly Val Thr Lys Ser Lys Ile Val Val Glu Pro Leu
            260                 265                 270

Phe Trp Pro Phe Glu Gln Lys Phe Asp Trp Thr Pro Glu Asp Ile Leu
        275                 280                 285

Lys His Phe Ser Met Ser Pro Arg Arg Lys Lys Ser Leu Gly Ser Lys
    290                 295                 300

Ile Ala Gly Thr Ser Pro Arg Ser Met Arg Ala Gln Leu Gln Thr Arg
305                 310                 315                 320

Lys Leu Asp Leu Lys Glu Gly Cys Lys Arg Lys Leu Met Phe Asn Gly
                325                 330                 335

Pro Gly Ser Asn Ser Lys Pro Thr Arg Ile Pro Glu Leu Asn Arg Thr
            340                 345                 350

Ile Ser Asn Ser Ser Asn Asn Ser Ser Met Lys Lys Thr Glu Ile Ser
        355                 360                 365

Lys Asn Gln Gln Pro Ile Arg Asn Ser Val Lys Arg Asn Lys Ser Leu
    370                 375                 380
```

-continued

Pro Ser Arg Leu Arg Lys Ser Ser Lys Ile Ser Ser Lys Val Val Pro
385                 390                 395                 400

Ile Glu Ala Ala Glu Ser Gly Glu Ile Val Lys Glu Gln Lys Thr
            405                 410                 415

Pro Lys Lys Leu Ile Met Thr Arg Lys Ser Arg Thr Phe Leu Glu Asp
        420                 425                 430

Asp Phe Ala Leu Met Asn Asp Phe Ser Ile Glu Lys Ala Val Gly Leu
        435                 440                 445

Cys Glu Phe Lys Gly Arg Glu Gly Ile Asp Ser Asp Phe Asn Thr Asp
        450                 455                 460

Gly Phe Leu Phe Asp Asp Ser Leu
465                 470

<210> SEQ ID NO 3
<211> LENGTH: 537
<212> TYPE: DNA
<213> ORGANISM: Arabidopsis thaliana

<400> SEQUENCE: 3
aaccacagtc gcggacagag ctaaaaccac catttgaaga aggagaagaa gaagaagacg      60
attcggtgaa agcgaagatg ggtggaggaa tggaaacgaa caagaacaag ttcatcgagg     120
actggggatc tgctagagag aatctcgagc acaatttccg ctggactcgt cgtaacttcg     180
ctctcatcgg aatcttcggc atcgctctcc cgatcattgt ctacaaggga atcgtcaaag     240
atttccatat gcaagatgaa gatgcaggca gaccacacag aaagttcctc tgaggttgtt     300
tgcaagaaca ctctctgcaa taaagtctca gcaatgtgaa atttcaagac gaggatgtta     360
aaacccgctt tgttttttc atttcaatca acatctggaa cccaaggata taatttattt      420
tttggaaaag tttgttgtaa tgactacact ttgttatgca aataaacaaa actcagtttt     480
cccttgagtt tgacatactt attgtgtgtg ttgattcagc atatgcagga tttaaac        537

<210> SEQ ID NO 4
<211> LENGTH: 71
<212> TYPE: PRT
<213> ORGANISM: Arabidopsis thaliana

<400> SEQUENCE: 4

Met Gly Gly Gly Met Glu Thr Asn Lys Asn Lys Phe Ile Glu Asp Trp
1               5                   10                  15

Gly Ser Ala Arg Glu Asn Leu Glu His Asn Phe Arg Trp Thr Arg Arg
            20                  25                  30

Asn Phe Ala Leu Ile Gly Ile Phe Gly Ile Ala Leu Pro Ile Ile Val
        35                  40                  45

Tyr Lys Gly Ile Val Lys Asp Phe His Met Gln Asp Glu Asp Ala Gly
    50                  55                  60

Arg Pro His Arg Lys Phe Leu
65                  70

<210> SEQ ID NO 5
<211> LENGTH: 1701
<212> TYPE: DNA
<213> ORGANISM: Arabidopsis thaliana

<400> SEQUENCE: 5
atggcaggtg ttactctctt cttctcccct ctctctatag ctctgattat ctctggtgtg      60
agctctcgtg tcctgatcag tcatgtccct ctgaataact cgatcttgat atctgatggg     120
atccatgacg ccttgaatca cgagtttctc accctcgatc ctccaaagag cttgtcaagg     180

```
accgcgtgtg ttcatgtcta cgggtttctt ccatgtgcag acaatgttga aggttatatc    240
ttccaagttt tttcctttgg gagtctcttg attatcggtg actatttctt gtccgaagga    300
agatctaaac tctttgtaat attcgaggtc gggttctatg gtggtatcat cttccctctt    360
cttacaatgt tcccaagaat cgctcttatg ctctcgaccg gactatcatt gagtagggat    420
gttgctagct cctttataga tgataacgtt ggacttactg tgggacacac tgtgttttct    480
ctcacaattc aatggggagc ttgtgttgtg tttagcatca ctggtccacg ttctgaccaa    540
gcagatggat tgatcgaaaa actaaagata ttgaaaggct ttgttgaagc aagagtagaa    600
gcggatccta agaataagaa agctgcaggg attatgctgt tgagtctatc tccctttctc    660
atggtgacat tttcggctat atttgattca cattcttgga gtcacatcat tgtgttgatc    720
acactcataa tttcttcttc ttcaaccgtt gtctactttg tttactcgta tcttgatacg    780
gctaaccaag agaagagctt agatcacgcg aggtttgagc tcatgtcaga agttcataag    840
cacttaaaga ggttttcacc gaaacacctt ataaagatg gagaactaag caaagagagc    900
ttgaaaagtt tgttcaagaa aactgataag aacaaagatg ggaagataca aatatctgaa    960
ctaaaagact taaccataga gctttccaac tttgggagaa tgagatatga catcaatgag    1020
cttgctaaag ctttcttga ggattttgat ggagacaacg acggcgaatt agaagagaat    1080
gaattcgagg aagggattgc gagacttctc aaacaataca aattcaacgt tgaggatcaa    1140
agagagaatc agactgagga aaatggagtt cttaagctgg aaattaaacc gaagaaaaca    1200
cttgttacta agttgctatc tatggaaaca ttaatagcta cgactgaagt catcgtaggg    1260
atcctaattg tactctttct tgcaaaacca tttatgctga acatccagct cttatccatc    1320
tcagctggaa ttccttcttt ctacatcgtg ttcgcgatga tcccttttcgc tagaaactta    1380
aagaacactc tatctacacg cttctgtcgt ggcaaagaca agaaaagagt ctcgtccaat    1440
actttctccg agatctacaa agatattaca atgaacaatc tcttgggaat gtcggtaata    1500
ttggcaattg tgtatacaag gggcttgact tggaaatact cggtagaaac tcttattatg    1560
gtgatcgttg gcctcataat cggcttacca atctatataa gatcgactta cccgttctgg    1620
atgtgtgtct tggcctttgc tatgtacttc ttttctcttc tccttatcta tatccgttta    1680
aattttctag acaagaacta a                                              1701
```

<210> SEQ ID NO 6
<211> LENGTH: 566
<212> TYPE: PRT
<213> ORGANISM: Arabidopsis thaliana

<400> SEQUENCE: 6

```
Met Ala Gly Val Thr Leu Phe Phe Ser Leu Leu Ser Ile Ala Leu Ile
1               5                   10                  15

Ile Ser Gly Val Ser Ser Arg Val Leu Ile Ser His Val Pro Leu Asn
                20                  25                  30

Asn Ser Ile Leu Ile Ser Asp Gly Ile His Asp Ala Leu Asn His Glu
            35                  40                  45

Phe Leu Thr Leu Asp Pro Pro Lys Ser Leu Ser Arg Thr Ala Cys Val
        50                  55                  60

His Val Tyr Gly Phe Leu Pro Cys Ala Asp Asn Val Glu Gly Tyr Ile
65                  70                  75                  80

Phe Gln Val Phe Ser Phe Gly Ser Leu Leu Ile Ile Gly Asp Tyr Phe
                85                  90                  95

Leu Ser Glu Gly Arg Ser Lys Leu Phe Val Ile Phe Glu Val Gly Phe
```

-continued

```
                100                 105                 110
Tyr Gly Gly Ile Ile Phe Pro Leu Leu Thr Met Phe Pro Arg Ile Ala
            115                 120                 125
Leu Met Leu Ser Thr Gly Leu Ser Leu Ser Arg Asp Val Ala Ser Ser
130                 135                 140
Phe Ile Asp Asp Asn Val Gly Leu Thr Val Gly His Thr Val Phe Ser
145                 150                 155                 160
Leu Thr Ile Gln Trp Gly Ala Cys Val Val Phe Ser Ile Thr Gly Pro
                165                 170                 175
Arg Ser Asp Gln Ala Asp Gly Leu Ile Glu Lys Leu Lys Ile Leu Lys
            180                 185                 190
Gly Phe Val Glu Ala Arg Val Glu Ala Asp Pro Lys Asn Lys Lys Ala
            195                 200                 205
Ala Gly Ile Met Leu Leu Ser Leu Ser Pro Phe Leu Met Val Thr Phe
            210                 215                 220
Ser Ala Ile Phe Asp Ser His Ser Trp Ser His Ile Ile Val Leu Ile
225                 230                 235                 240
Thr Leu Ile Ile Ser Ser Ser Thr Val Val Tyr Phe Val Tyr Ser
                245                 250                 255
Tyr Leu Asp Thr Ala Asn Gln Glu Lys Ser Leu Asp His Ala Arg Phe
            260                 265                 270
Glu Leu Met Ser Glu Val His Lys His Leu Lys Arg Phe Ser Pro Lys
            275                 280                 285
His Leu Ile Lys Asp Gly Glu Leu Ser Lys Glu Ser Leu Lys Ser Leu
            290                 295                 300
Phe Lys Lys Thr Asp Lys Asn Lys Asp Gly Lys Ile Gln Ile Ser Glu
305                 310                 315                 320
Leu Lys Asp Leu Thr Ile Glu Leu Ser Asn Phe Gly Arg Met Arg Tyr
                325                 330                 335
Asp Ile Asn Glu Leu Ala Lys Ala Phe Leu Glu Asp Phe Asp Gly Asp
            340                 345                 350
Asn Asp Gly Glu Leu Glu Glu Asn Glu Phe Glu Glu Gly Ile Ala Arg
            355                 360                 365
Leu Leu Lys Gln Tyr Lys Phe Asn Val Glu Asp Gln Arg Glu Asn Gln
            370                 375                 380
Thr Glu Glu Asn Gly Val Leu Lys Leu Glu Ile Lys Pro Lys Lys Thr
385                 390                 395                 400
Leu Val Thr Lys Leu Leu Ser Met Glu Thr Leu Ile Ala Thr Thr Glu
                405                 410                 415
Val Ile Val Gly Ile Leu Ile Val Leu Phe Leu Ala Lys Pro Phe Met
            420                 425                 430
Leu Asn Ile Gln Leu Leu Ser Ile Ser Ala Gly Ile Pro Ser Phe Tyr
            435                 440                 445
Ile Val Phe Ala Met Ile Pro Phe Ala Arg Asn Leu Lys Asn Thr Leu
            450                 455                 460
Ser Thr Arg Phe Cys Arg Gly Lys Asp Lys Lys Arg Val Ser Ser Asn
465                 470                 475                 480
Thr Phe Ser Glu Ile Tyr Lys Asp Ile Thr Met Asn Asn Leu Leu Gly
                485                 490                 495
Met Ser Val Ile Leu Ala Ile Val Tyr Thr Arg Gly Leu Thr Trp Lys
            500                 505                 510
Tyr Ser Val Glu Thr Leu Ile Met Val Ile Val Gly Leu Ile Ile Gly
            515                 520                 525
```

Leu Pro Ile Tyr Ile Arg Ser Thr Tyr Pro Phe Trp Met Cys Val Leu
            530                 535                 540

Ala Phe Ala Met Tyr Phe Phe Ser Leu Leu Leu Ile Tyr Ile Arg Leu
545                 550                 555                 560

Asn Phe Leu Asp Lys Asn
            565

<210> SEQ ID NO 7
<211> LENGTH: 1436
<212> TYPE: DNA
<213> ORGANISM: Arabidopsis thaliana

<400> SEQUENCE: 7

```
aaggaaggtc gtgagaaaag aaaaacactt ctcaatcttt ctacagtctt cttcttccaa      60
aagaacacca tcttccttcg taatgtcaga gaaccagtcc gaagaagtcc agcaaatcga     120
gaagctctat gagttcagtg agcgtctcaa tgcctccaag acaagtctc agaatgttga     180
ggattatgag gggatcatta agatgtccaa gactagtatg aaggcaaagc agcttgcgtc     240
gcagctaatt cctcgctact tcaagttctt ccctagtctc tctactgagg ctttcgatgc     300
gcatatggac tgtatcgatg atggagatct tggggtacgt gttcaagcca tccgtgggct     360
cccgctgttt tgtaaggata cgccagatat tttatctaag attgttgatg ttcttgttca     420
actcttgaat acagaggaac ctgtggagcg tgatgctgtg cataaggctc tgatgtcatt     480
gttacgacaa gatccaaaag catcatcgac tgccttattt acccatgctg gggttactcc     540
aactactgat gatcaaattc gtgaaaaggt cttgaatttc atcagagata aggtgattcc     600
tcttaaaggg gaactcttaa agcctcaaga ggagatggaa agacatataa cagatttgat     660
caaacagagc ctagaagatg taactggagg agagtttaaa atgtttatgg atttcctgac     720
aagtttgagt atatttggag gcaaagctcc tccagaaaga atgcaagaac ttgtggaaat     780
tattgaagga caggcggatt taaatgcaca atttgaattt tcagatacgg accatattga     840
caggttgata tcatgcctgc aactggctct tccctttttt gcgagaggtg ctccaagcag     900
caggtttctt atctatttga acaaacatat catacctgtt tttgacaagc tcccagaaga     960
gaggaaactt gatttgctca agcacttgc tgatatttct ccatacacaa ctgctcagga    1020
agcaaggcag ctgcttcctt caatcgttga gcttttaaag atatacatgc ctgctagaaa    1080
gactggagag gaaatgaact tcacatacgt cgagtgtttg ttgtatgcgt tcatcaccct    1140
tgcccacaag gttccaaatg ctacaaacag cttgtgtggg tacaagattg tgaccggcca    1200
gccatcagac agattggggg aggacttctc agagttgaac aaagacttta ctgagagatt    1260
aaccattgtt gaggatctaa ctaaggcaac gatgaagaaa ttaactcagg gaatgactga    1320
gcacaacaaa gccatgtcgg ctgctaagac agatgaagag aaagcgagta ttgtaagtac    1380
attaacctgt gctatttct attttttccta gtgctatttg ctttcagtac taatgc        1436
```

<210> SEQ ID NO 8
<211> LENGTH: 442
<212> TYPE: PRT
<213> ORGANISM: Arabidopsis thaliana

<400> SEQUENCE: 8

Met Ser Glu Asn Gln Ser Glu Glu Val Gln Gln Ile Glu Lys Leu Tyr
1               5                   10                  15

Glu Phe Ser Glu Arg Leu Asn Ala Ser Lys Asp Lys Ser Gln Asn Val
            20                  25                  30

Glu Asp Tyr Glu Gly Ile Ile Lys Met Ser Lys Thr Ser Met Lys Ala

```
                35                  40                  45
Lys Gln Leu Ala Ser Gln Leu Ile Pro Arg Tyr Phe Lys Phe Phe Pro
 50                  55                  60

Ser Leu Ser Thr Glu Ala Phe Asp Ala His Met Asp Cys Ile Asp Asp
 65                  70                  75                  80

Gly Asp Leu Gly Val Arg Val Gln Ala Ile Arg Gly Leu Pro Leu Phe
                 85                  90                  95

Cys Lys Asp Thr Pro Asp Ile Leu Ser Lys Ile Val Asp Val Leu Val
                100                 105                 110

Gln Leu Leu Asn Thr Glu Glu Pro Val Glu Arg Asp Ala Val His Lys
            115                 120                 125

Ala Leu Met Ser Leu Leu Arg Gln Asp Pro Lys Ala Ser Ser Thr Ala
130                 135                 140

Leu Phe Thr His Ala Gly Val Thr Pro Thr Thr Asp Asp Gln Ile Arg
145                 150                 155                 160

Glu Lys Val Leu Asn Phe Ile Arg Asp Lys Val Ile Pro Leu Lys Gly
                165                 170                 175

Glu Leu Leu Lys Pro Gln Glu Glu Met Glu Arg His Ile Thr Asp Leu
            180                 185                 190

Ile Lys Gln Ser Leu Glu Asp Val Thr Gly Gly Glu Phe Lys Met Phe
        195                 200                 205

Met Asp Phe Leu Thr Ser Leu Ser Ile Phe Gly Gly Lys Ala Pro Pro
210                 215                 220

Glu Arg Met Gln Glu Leu Val Glu Ile Ile Glu Gly Gln Ala Asp Leu
225                 230                 235                 240

Asn Ala Gln Phe Glu Phe Ser Asp Thr Asp His Ile Asp Arg Leu Ile
                245                 250                 255

Ser Cys Leu Gln Leu Ala Leu Pro Phe Phe Ala Arg Gly Ala Pro Ser
            260                 265                 270

Ser Arg Phe Leu Ile Tyr Leu Asn Lys His Ile Ile Pro Val Phe Asp
        275                 280                 285

Lys Leu Pro Glu Glu Arg Lys Leu Asp Leu Leu Lys Ala Leu Ala Asp
290                 295                 300

Ile Ser Pro Tyr Thr Thr Ala Gln Glu Ala Arg Gln Leu Leu Pro Ser
305                 310                 315                 320

Ile Val Glu Leu Leu Lys Ile Tyr Met Pro Ala Arg Lys Thr Gly Glu
                325                 330                 335

Glu Met Asn Phe Thr Tyr Val Cys Leu Leu Tyr Ala Phe His His
            340                 345                 350

Leu Ala His Lys Val Pro Asn Ala Thr Asn Ser Leu Cys Gly Tyr Lys
        355                 360                 365

Ile Val Thr Gly Gln Pro Ser Asp Arg Leu Gly Glu Asp Phe Ser Glu
370                 375                 380

Leu Asn Lys Asp Phe Thr Glu Arg Leu Thr Ile Val Glu Asp Leu Thr
385                 390                 395                 400

Lys Ala Thr Met Lys Lys Leu Thr Gln Gly Met Thr Glu His Asn Lys
                405                 410                 415

Ala Met Ser Ala Ala Lys Thr Asp Glu Glu Lys Ala Ser Ile Val Ser
            420                 425                 430

Thr Leu Thr Cys Ala Ile Phe Tyr Phe Ser
        435                 440

<210> SEQ ID NO 9
<211> LENGTH: 1963
```

<212> TYPE: DNA
<213> ORGANISM: Arabidopsis thaliana

<400> SEQUENCE: 9

```
aaggaaggtc gtgagaaaag aaaaacactt ctcaatctttt ctacagtctt cttcttccaa      60
aagaacacca tcttccttcg taatgtcaga gaaccagtcc gaagaagtcc agcaaatcga     120
gaagctctat gagttcagtg agcgtctcaa tgcctccaag acaagtctc agaatgttga      180
ggattatgag gggatcatta agatgtccaa gactagtatg aaggcaaagc agcttgcgtc     240
gcagctaatt cctcgctact tcaagttctt ccctagtctc tctactgagg ctttcgatgc     300
gcatatggac tgtatcgatg atggagatct tggggtacgt gttcaagcca tccgtgggct     360
cccgctgttt tgtaaggata cgccagatat tttatctaag attgttgatg ttcttgttca     420
actcttgaat acagaggaac ctgtggagcg tgatgctgtg cataaggctc tgatgtcatt     480
gttacgacaa gatccaaaag catcatcgac tgccttattt acccatgctg gggttactcc     540
aactactgat gatcaaattc gtgaaaaggt cttgaatttc atcagagata aggtgattcc     600
tcttaaaggg gaactcttaa agcctcaaga ggagatggaa agacatataa cagatttgat     660
caaacagagc ctagaagatg taactggagg agagtttaaa atgtttatgg atttcctgac     720
aagtttgagt atatttggag gcaaagctcc tccagaaaga atgcaagaac ttgtggaaat     780
tattgaagga caggcggatt taaatgcaca atttgaattt tcagatacgg accatattga     840
caggttgata tcatgcctgc aactggctct tccctttttt gcgagaggtg ctccaagcag     900
caggtttctt atctatttga acaaacatat catacctgtt tttgacaagc tcccagaaga     960
gaggaaactt gatttgctca agcacttgc tgatatttct ccatacacaa ctgctcagga    1020
agcaaggcag ctgcttcctt caatcgttga gcttttaaag atatacatgc ctgctagaaa    1080
gactggagag gaaatgaact tcacatacgt cgagtgtttg ttgtatgcgt tcatcacct     1140
tgcccacaag gttccaaatg ctacaaacag cttgtgtggg tacaagattg tgaccggcca    1200
gccatcagac agattggggg aggacttctc agagttgaac aaagacttta ctgagagatt    1260
aaccattgtt gaggatctaa ctaaggcaac gatgaagaaa ttaactcagg gaatgactga    1320
gcacaacaaa gccatgtcgg ctgctaagac agatgaagag aaagcgagta ttaaaacaaa    1380
gaggcagaat actacaactg gactaggac ctgtaataac atattggcga tgacaaagcc     1440
attgcatgca aaagtgccac cttttatcgg agacactaat ctcaacctgt cttggaaaga    1500
agccacaaag ccgttagcct caacaacaac aacaattgga ggaaagcggc ctgctaatag    1560
caacaatgga agtggtaaca atgttgcagc aaagaaggga cgtgggtcgg gtactatgca    1620
aaaccagctt gtgaacaagg cctttgaggg gatatcatcc tatggagctg gtagaggcgg    1680
aaaccgaggt tggggaagac gtggaggtgg tcgaggaaga ggacaaggaa gaggtcactg    1740
gtaataacaa gttccagta gaggattcca tgactgtgtt tctgttctg tgtctgtctg       1800
tcagtacaag ttttgatttt ggtacttagt agagtttgga gacttctctt ctcatatcag    1860
aatagatcat ctgtgttttt ctctgttcac taaagatatt tcgagcatta gaaaaaaga     1920
tatttcgagc atttatgacc ttagttatac aatctttcta gtc                      1963
```

<210> SEQ ID NO 10
<211> LENGTH: 553
<212> TYPE: PRT
<213> ORGANISM: Arabidopsis thaliana

<400> SEQUENCE: 10

Met Ser Glu Asn Gln Ser Glu Glu Val Gln Gln Ile Glu Lys Leu Tyr

-continued

```
1               5               10              15
Glu Phe Ser Glu Arg Leu Asn Ala Ser Lys Asp Lys Ser Gln Asn Val
                20              25              30

Glu Asp Tyr Glu Gly Ile Ile Lys Met Ser Lys Thr Ser Met Lys Ala
                35              40              45

Lys Gln Leu Ala Ser Gln Leu Ile Pro Arg Tyr Phe Lys Phe Phe Pro
                50              55              60

Ser Leu Ser Thr Glu Ala Phe Asp Ala His Met Asp Cys Ile Asp Asp
65              70              75              80

Gly Asp Leu Gly Val Arg Val Gln Ala Ile Arg Gly Leu Pro Leu Phe
                85              90              95

Cys Lys Asp Thr Pro Asp Ile Leu Ser Lys Ile Val Asp Val Leu Val
                100             105             110

Gln Leu Leu Asn Thr Glu Glu Pro Val Glu Arg Asp Ala Val His Lys
                115             120             125

Ala Leu Met Ser Leu Leu Arg Gln Asp Pro Lys Ala Ser Ser Thr Ala
                130             135             140

Leu Phe Thr His Ala Gly Val Thr Pro Thr Thr Asp Asp Gln Ile Arg
145             150             155             160

Glu Lys Val Leu Asn Phe Ile Arg Asp Lys Val Ile Pro Leu Lys Gly
                165             170             175

Glu Leu Leu Lys Pro Gln Glu Glu Met Glu Arg His Ile Thr Asp Leu
                180             185             190

Ile Lys Gln Ser Leu Glu Asp Val Thr Gly Gly Glu Phe Lys Met Phe
                195             200             205

Met Asp Phe Leu Thr Ser Leu Ser Ile Phe Gly Gly Lys Ala Pro Pro
210             215             220

Glu Arg Met Gln Glu Leu Val Glu Ile Ile Glu Gly Gln Ala Asp Leu
225             230             235             240

Asn Ala Gln Phe Glu Phe Ser Asp Thr Asp His Ile Ala Arg Leu Ile
                245             250             255

Ser Cys Leu Gln Leu Ala Leu Pro Phe Phe Ala Arg Gly Ala Pro Ser
                260             265             270

Ser Arg Phe Leu Ile Tyr Leu Asn Lys His Ile Ile Pro Val Phe Asp
                275             280             285

Lys Leu Pro Glu Glu Arg Lys Leu Asp Leu Leu Lys Ala Leu Ala Asp
                290             295             300

Ile Ser Pro Tyr Thr Thr Ala Gln Glu Ala Arg Gln Leu Leu Pro Ser
305             310             315             320

Ile Val Glu Leu Leu Lys Ile Tyr Met Pro Ala Arg Lys Thr Gly Glu
                325             330             335

Glu Met Asn Phe Thr Tyr Val Glu Cys Leu Leu Tyr Ala Phe His His
                340             345             350

Leu Ala His Lys Val Pro Asn Ala Thr Asn Ser Leu Cys Gly Tyr Lys
                355             360             365

Ile Val Thr Gly Gln Pro Ser Asp Arg Leu Gly Glu Asp Phe Ser Glu
                370             375             380

Leu Asn Lys Asp Phe Thr Glu Arg Leu Thr Ile Val Glu Asp Leu Thr
385             390             395             400

Lys Ala Thr Met Lys Lys Leu Thr Gln Gly Met Thr Glu His Asn Lys
                405             410             415

Ala Met Ser Ala Ala Lys Thr Asp Glu Glu Lys Ala Ser Ile Lys Thr
                420             425             430
```

```
Lys Arg Gln Asn Thr Thr Thr Gly Leu Arg Thr Cys Asn Asn Ile Leu
        435                 440                 445

Ala Met Thr Lys Pro Leu His Ala Lys Val Pro Pro Phe Ile Gly Asp
    450                 455                 460

Thr Asn Leu Asn Leu Ser Trp Lys Glu Ala Thr Lys Pro Leu Ala Ser
465                 470                 475                 480

Thr Thr Thr Thr Ile Gly Gly Lys Arg Pro Ala Asn Ser Asn Gly
                485                 490                 495

Ser Gly Asn Asn Val Ala Ala Lys Lys Gly Arg Gly Ser Gly Thr Met
            500                 505                 510

Gln Asn Gln Leu Val Asn Lys Ala Phe Glu Gly Ile Ser Ser Tyr Gly
        515                 520                 525

Ala Gly Arg Gly Gly Asn Arg Gly Trp Gly Arg Gly Gly Arg
    530                 535                 540

Gly Arg Gly Gln Gly Arg Gly His Trp
545                 550

<210> SEQ ID NO 11
<211> LENGTH: 987
<212> TYPE: DNA
<213> ORGANISM: Arabidopsis thaliana

<400> SEQUENCE: 11
agggttctaa atctgagatt ccagagaac tgtgcatatc ttcatagttt ctttgaattt      60
caccgtattc ataccataaa aatgagaaga atcgtcggtt caatttcgag tcttgctaaa   120
gataagctct cttcatcttc ttattcttcg tctagacaaa ttttcactgc gcgttcatct   180
tcttggcaac gagatgcatc aagtaagctc tcagaagctt cttttacctgg aaaccacata   240 aaatgggctt cgcttggttc agtcagaaat tcgagattcg catctggttt tacaccattg   300
cagcaaaaac ctttggattc aatcatggat ttggccagag ccaagactaa atcccctgaa   360
gaactcactt cgatctggga cgattatcat ttgggacgag gtcatattgg gttaacgatg   420
aaagctcagc tttatcgatt gttggagcaa cgagcctccg agtgccgata ctttgtcatt   480
ccattgtgga gagaaatgg ttacataaca atgtttgctc aagttgaagc gcctcacatg   540 attttttactg gtctcgaaga ctacaaagca agaggaactc aagcggctcc ttacctgact   600
acaaccttct acactgagct ttcagagaca aaagacttgg tctttatccg aggcgatgtt   660
gtgttcacaa gcaaactcac tgacgaggag gctaaatgga tcatggagac agctcaatcg   720 tttatttga cgactctccg ctacaagctg cttgagcggt tcaataaaca tactcatgac   780
tttgagttca aggatgtgtt acaagctctg gatatgcctc ttctgtgatt atcaggagaa   840
aaaacttttc tggcttttga gttcttgaga caacaacacc ttgtattaga atttttttg    900 tatggtaata agactatttc atgaccaaac taggtttggt tggatactta ctgtgttttg   960 ctttttataaa taaacaattt tgagtaa                                      987

<210> SEQ ID NO 12
<211> LENGTH: 248
<212> TYPE: PRT
<213> ORGANISM: Arabidopsis thaliana

<400> SEQUENCE: 12

Met Arg Arg Ile Val Gly Ser Ile Ser Ser Leu Ala Lys Asp Lys Leu
1               5                   10                  15

Ser Ser Ser Ser Tyr Ser Ser Ser Arg Gln Ile Phe Thr Ala Arg Ser
            20                  25                  30
```

```
Ser Ser Trp Gln Arg Asp Ala Ser Ser Lys Leu Ser Glu Ala Ser Leu
        35                  40                  45

Pro Gly Asn His Ile Lys Trp Ala Ser Leu Gly Ser Val Arg Asn Ser
 50                  55                  60

Arg Phe Ala Ser Gly Phe Thr Pro Leu Gln Gln Lys Pro Leu Asp Ser
 65                  70                  75                  80

Ile Met Asp Leu Ala Arg Ala Lys Thr Lys Ser Pro Glu Gly Leu Thr
                 85                  90                  95

Ser Ile Trp Asp Asp Tyr His Leu Gly Arg Gly His Ile Gly Leu Thr
                100                 105                 110

Met Lys Ala Gln Leu Tyr Arg Leu Leu Glu Gln Arg Ala Ser Glu Cys
            115                 120                 125

Arg Tyr Phe Val Ile Pro Leu Trp Arg Gly Asn Gly Tyr Ile Thr Met
130                 135                 140

Phe Ala Gln Val Glu Ala Pro His Met Ile Phe Thr Gly Leu Glu Asp
145                 150                 155                 160

Tyr Lys Ala Arg Gly Thr Gln Ala Ala Pro Tyr Leu Thr Thr Thr Phe
                165                 170                 175

Tyr Thr Glu Leu Ser Glu Thr Lys Asp Leu Val Phe Ile Arg Gly Asp
                180                 185                 190

Val Val Phe Thr Ser Lys Leu Thr Asp Glu Glu Ala Lys Trp Ile Met
            195                 200                 205

Glu Thr Ala Gln Ser Phe Tyr Leu Asn Asp Ser Arg Tyr Lys Leu Leu
210                 215                 220

Glu Arg Phe Asn Lys His Thr His Asp Phe Glu Phe Lys Asp Val Leu
225                 230                 235                 240

Gln Ala Leu Asp Met Pro Leu Leu
                245

<210> SEQ ID NO 13
<211> LENGTH: 1180
<212> TYPE: DNA
<213> ORGANISM: Arabidopsis thaliana

<400> SEQUENCE: 13
atgcatgtca tatctctttc gttatcctca tatattcttt tcctcttcct cacatcaacc      60
attttgattt ctccggtaca acccacaacc tctaagcctc cggcaccacg gccccacaga     120
gagctctccg ccgattacta ctccaagaaa tgtcctcagc ttgaaactct cgtcggttcc     180
gtcacttctc agcggttcaa agaagtcccc atctcagctc cagccaccat cgcctcttc      240 tttcacgact gcttcgttga gggttgtgat gggtcgatat tgatagaaac aaagaaagga     300
agcaagaaat tagcagagag agaagcatat gagaataagg aattgagaga ggaaggattt     360
gatagtatca tcaaggcgaa ggccttggtt gagtctcatt gcccttctct cgtctcttgc     420
tctgatattc tcgctattgc cgctcgagat ttcattcatc tggcaggtgg gccttactat     480
caagtgaaaa aaggaaggtg ggacggaaaa agatcaacgg caaagaacgt ccctccaaac     540
atacctcgat caaactccac cgttgatcaa ctcatcaagc tcttcgcgtc caaaggacta     600
accgtagagg aactcgtcgt cctttctggt tcccacacca tcggcttcgc ccattgtaaa     660
aatttccttg gtcgtctcta cgactacaaa ggcacaaaac gacccgaccc gagtcttgac     720
caaagattac taaagagct  ccggatgtct tgtccttttt ccggcggaag ctctggagtc     780
gtccttccgc tcgacgctac aactccgttt gtgtttgata atggatattt cacaggtcta     840
ggaaccaaca tgggccttct cggggtcggac caagctttgt tccttgaccc gaggacgaag     900
```

```
cccattgcac ttgagatggc aagagataag cagaagtttc tcaaggcgtt tggagacgct      960
atggataaaa tgggttccat tggtgtaaag agagggaaga acatgggga aatacgtacg      1020 gattgtcgag tcttttata gatttctttt attgtcttgt ctgatggttt tgtcttgat      1080 cttgatgtgt tctgtgtcat gtgtccttta attattagc attttcgtga ttgttttgtt      1140
gatagtataa ggtattttt taaagcaaca ctaacttatc                            1180
```

<210> SEQ ID NO 14
<211> LENGTH: 248
<212> TYPE: PRT
<213> ORGANISM: Arabidopsis thaliana

<400> SEQUENCE: 14

```
Met Arg Arg Ile Val Gly Ser Ile Ser Ser Leu Ala Lys Asp Lys Leu
1               5                   10                  15

Ser Ser Ser Ser Tyr Ser Ser Arg Gln Ile Phe Thr Ala Arg Ser
            20                  25                  30

Ser Ser Trp Gln Arg Asp Ala Ser Ser Lys Leu Ser Glu Ala Ser Leu
        35                  40                  45

Pro Gly Asn His Ile Lys Trp Ala Ser Leu Gly Ser Val Arg Asn Ser
    50                  55                  60

Arg Phe Ala Ser Gly Phe Thr Pro Leu Gln Gln Lys Pro Leu Asp Ser
65                  70                  75                  80

Ile Met Asp Leu Ala Arg Ala Lys Thr Lys Ser Pro Glu Glu Leu Thr
                85                  90                  95

Ser Ile Trp Asp Asp Tyr His Leu Gly Arg Gly His Ile Gly Leu Thr
            100                 105                 110

Met Lys Ala Gln Leu Tyr Arg Leu Leu Glu Gln Arg Ala Ser Glu Cys
        115                 120                 125

Arg Tyr Phe Val Ile Pro Leu Trp Arg Gly Asn Gly Tyr Ile Thr Met
    130                 135                 140

Phe Ala Gln Val Glu Ala Pro His Met Ile Phe Thr Gly Leu Glu Asp
145                 150                 155                 160

Tyr Lys Ala Arg Gly Thr Gln Ala Ala Pro Tyr Leu Thr Thr Thr Phe
                165                 170                 175

Tyr Thr Glu Leu Ser Glu Thr Lys Asp Leu Val Phe Ile Arg Gly Asp
            180                 185                 190

Val Val Phe Thr Ser Lys Leu Thr Asp Glu Glu Ala Lys Trp Ile Met
        195                 200                 205

Glu Thr Ala Gln Ser Phe Tyr Leu Asn Asp Ser Arg Tyr Lys Leu Leu
    210                 215                 220

Glu Arg Phe Asn Lys His Thr His Asp Phe Glu Phe Lys Asp Val Leu
225                 230                 235                 240

Gln Ala Leu Asp Met Pro Leu Leu
                245
```

<210> SEQ ID NO 15
<211> LENGTH: 1854
<212> TYPE: DNA
<213> ORGANISM: Arabidopsis thaliana

<400> SEQUENCE: 15

```
atgctcatca aaccagagaa actagcgttc tcgatttacc gccaatttcc taaattcaaa      60
cctagacaat ttgaagaagc acgacgcggc gatctcgaga gggactttct tttcctgttg     120
aaaaaatgta tctccgtgaa ccaattgcga cagattcaag cccagatgtt gttacactcc     180
```

```
gtcgaaaaac cgaattttct gattcccaag gccgtcgaac ttggagactt caattactcc    240
tcttttctct tctccgtcac ggaagaacca aaccattact ctttcaatta catgatccga    300
gggttgacca acacatggaa tgatcacgaa gctgctctgt ctctgtatcg acggatgaag    360
ttttctgggt taaagcctga taagttcact tataattttg ttttcatcgc ttgtgcgaag    420
cttgaggaga taggagttgg tagatctgtc cactcgtcgt tgttcaaagt tggattggaa    480
agagacgttc atataaatca ttctctgatt atgatgtatg cgaaatgtgg tcaggtgggt    540
tatgcccgga agttgttcga tgaaattact gagagagata cggtgtcttg gaactcgatg    600
atctctgggt attctgaggc gggttacgct aaagatgcta tggatttgtt taggaagatg    660
gaggaggaag gatttgaacc agatgagagg acgttggtga gtatgttggg tgcttgctca    720
catttgggtg atttgagaac tggtagattg ctggaggaga tggccatcac caagaagatc    780
gggttaagca cgtttctggg gtctaagttg atcagtatgt atggaaaatg tggtgatttg    840
gattctgcca aagggtttt caatcaaatg attaagaagg atcgtgttgc ttggactgct    900
atgatcactg tatactcaca aaatgggaag tcaagtgagg cttttaaact gttttttgag    960
atggaaaaaa ccggagtttc accagacgcg ggcacattgt ctacagttct gtctgcttgt   1020
ggttcagttg gagctcttga attaggcaaa caaattgaga cccatgcatc agaactttcc   1080
ttgcaacata atatctatgt ggccacagga ctagtcgaca tgtatggaaa gtgcggacgg   1140
gtagaggaag ctctgagagt atttgaagct atgccagtga aaaacgaagc cacttggaac   1200
gctatgataa ccgcttatgc gcatcaagga cacgctaaag aagctctttt gctgtttgat   1260
cgaatgtcag ttcctccaag tgatataaca ttcataggag tgctctctgc ttgtgtgcac   1320
gcgggttttgg tccatcaggg ctgtcgatat ttccatgaga tgagttctat gttcgggttg   1380
gtcccaaaaa tcgagcatta cacaaacata atcgatctcc tgtctcgtgc ggggatgtta   1440
gacgaggctt gggagttcat ggagaggttt cctgggaagc ctgatgagat catgttagca   1500
gcgatccttg gagcatgtca aagagaaaa gatgttgcga tcagagagaa ggcgatgagg   1560
atgttgatgg agatgaaaga ggcgaagaac gcaggaaact atgtaatctc ttctaatgtt   1620
ttagctgata tgaagatgtg ggatgagtct gcgaagatga gggcgttgat gagagacaga   1680
ggcgtcgtta agacaccagg atgcagctgg attgagatcg agggtgagct aatggaattt   1740
cttgccggaa gcgattattt acagtgtggc agggaagatt ccggttcgtt atttgatttg   1800
ttggtggagg agatgaagag ggaaaggtat gaatttggtt acattcacct gtga         1854
```

<210> SEQ ID NO 16
<211> LENGTH: 617
<212> TYPE: PRT
<213> ORGANISM: Arabidopsis thaliana
<400> SEQUENCE: 16

```
Met Leu Ile Lys Pro Glu Lys Leu Ala Phe Ser Ile Tyr Arg Gln Phe
 1               5                  10                  15

Pro Lys Phe Lys Pro Arg Gln Phe Glu Glu Ala Arg Arg Gly Asp Leu
            20                  25                  30

Glu Arg Asp Phe Leu Phe Leu Lys Lys Cys Ile Ser Val Asn Gln
        35                  40                  45

Leu Arg Gln Ile Gln Ala Gln Met Leu Leu His Ser Val Glu Lys Pro
    50                  55                  60

Asn Phe Leu Ile Pro Lys Ala Val Glu Leu Gly Asp Phe Asn Tyr Ser
65                  70                  75                  80

Ser Phe Leu Phe Ser Val Thr Glu Glu Pro Asn His Tyr Ser Phe Asn
```

```
                85                  90                  95
Tyr Met Ile Arg Gly Leu Thr Asn Thr Trp Asn Asp His Glu Ala Ala
            100                 105                 110

Leu Ser Leu Tyr Arg Arg Met Lys Phe Ser Gly Leu Lys Pro Asp Lys
            115                 120                 125

Phe Thr Tyr Asn Phe Val Phe Ile Ala Cys Ala Lys Leu Glu Glu Ile
            130                 135                 140

Gly Val Gly Arg Ser Val His Ser Ser Leu Phe Lys Val Gly Leu Glu
145                 150                 155                 160

Arg Asp Val His Ile Asn His Ser Leu Ile Met Met Tyr Ala Lys Cys
                165                 170                 175

Gly Gln Val Gly Tyr Ala Arg Lys Leu Phe Asp Glu Ile Thr Glu Arg
            180                 185                 190

Asp Thr Val Ser Trp Asn Ser Met Ile Ser Gly Tyr Ser Glu Ala Gly
            195                 200                 205

Tyr Ala Lys Asp Ala Met Asp Leu Phe Arg Lys Met Glu Glu Glu Gly
210                 215                 220

Phe Glu Pro Asp Glu Arg Thr Leu Val Ser Met Leu Gly Ala Cys Ser
225                 230                 235                 240

His Leu Gly Asp Leu Arg Thr Gly Arg Leu Leu Glu Glu Met Ala Ile
                245                 250                 255

Thr Lys Lys Ile Gly Leu Ser Thr Phe Leu Gly Ser Lys Leu Ile Ser
            260                 265                 270

Met Tyr Gly Lys Cys Gly Asp Leu Asp Ser Ala Arg Arg Val Phe Asn
            275                 280                 285

Gln Met Ile Lys Lys Asp Arg Val Ala Trp Thr Ala Met Ile Thr Val
            290                 295                 300

Tyr Ser Gln Asn Gly Lys Ser Ser Glu Ala Phe Lys Leu Phe Phe Glu
305                 310                 315                 320

Met Glu Lys Thr Gly Val Ser Pro Asp Ala Gly Thr Leu Ser Thr Val
                325                 330                 335

Leu Ser Ala Cys Gly Ser Val Gly Ala Leu Glu Leu Gly Lys Gln Ile
            340                 345                 350

Glu Thr His Ala Ser Glu Leu Ser Leu Gln His Asn Ile Tyr Val Ala
            355                 360                 365

Thr Gly Leu Val Asp Met Tyr Gly Lys Cys Gly Arg Val Glu Glu Ala
            370                 375                 380

Leu Arg Val Phe Glu Ala Met Pro Val Lys Asn Glu Ala Thr Trp Asn
385                 390                 395                 400

Ala Met Ile Thr Ala Tyr Ala His Gln Gly His Ala Lys Glu Ala Leu
                405                 410                 415

Leu Leu Phe Asp Arg Met Ser Val Pro Pro Ser Asp Ile Thr Phe Ile
            420                 425                 430

Gly Val Leu Ser Ala Cys Val His Ala Gly Leu Val His Gln Gly Cys
            435                 440                 445

Arg Tyr Phe His Glu Met Ser Ser Met Phe Gly Leu Val Pro Lys Ile
            450                 455                 460

Glu His Tyr Thr Asn Ile Ile Asp Leu Leu Ser Arg Ala Gly Met Leu
465                 470                 475                 480

Asp Glu Ala Trp Glu Phe Met Glu Arg Phe Pro Gly Lys Pro Asp Glu
                485                 490                 495

Ile Met Leu Ala Ala Ile Leu Gly Ala Cys His Lys Arg Lys Asp Val
            500                 505                 510
```

```
Ala Ile Arg Glu Lys Ala Met Arg Met Leu Met Glu Met Lys Glu Ala
        515                 520                 525
Lys Asn Ala Gly Asn Tyr Val Ile Ser Ser Asn Val Leu Ala Asp Met
530                 535                 540
Lys Met Trp Asp Glu Ser Ala Lys Met Arg Ala Leu Met Arg Asp Arg
545                 550                 555                 560
Gly Val Val Lys Thr Pro Gly Cys Ser Trp Ile Glu Ile Gly Glu
                565                 570                 575
Leu Met Glu Phe Leu Ala Gly Ser Asp Tyr Leu Gln Cys Gly Arg Glu
            580                 585                 590
Asp Ser Gly Ser Leu Phe Asp Leu Leu Val Glu Met Lys Arg Glu
            595                 600                 605
Arg Tyr Glu Phe Gly Tyr Ile His Leu
        610                 615

<210> SEQ ID NO 17
<211> LENGTH: 3299
<212> TYPE: DNA
<213> ORGANISM: Arabidopsis thaliana

<400> SEQUENCE: 17
gaacggacca gaaaagagaa cattcgccaa accaaccaac aaccgtttgg gtgagcttga      60
cgagaacgac gtcgcacccg ccattttctc catccttgaa gcaacacctt cttcacttca     120
gatctcttct tcttcttctt cttcttcttc ttcttcttct ttgctcgcac cttccgtgct     180
attgtatttc tagggtttcg gatcctgtgc cttaccttag atccgacggt ggagtagaaa     240
tcactctccc tgtctcttcc cttcttttt gtttccagtt tttgattgaa gatcccttcg     300
tggatccact ataatggcgg attctcagcc aatcacgcct ggtcaggttt cgtttctact     360
cggagtcatt cctgtcttca tagcatggat ttactcagag tttctagagt ataagaggtc     420
ttcattgcac tctaaagttc attcagataa taatttggtt gaacttggtg aggtaaaaaa     480
caaggaagat gaaggagtag ttttacttga aggaggtctt ccaagatcag tctctacaaa     540
gttttataac tcacctatca aaacaaactt gattagattt ctgacgctgg aagactcttt     600
cttgattgaa aatcgagcaa ccttgagagc gatggctgag tttggggcta ttctttttta     660
cttttatatt agtgatcgaa caagcttgct tggagagtct aaaaagaatt acaacagaga     720
tcttttcctc tttctctact gtcttctcat catagtttca gccatgacat ccttgaagaa     780
acacaatgac aaatcaccta aacaggaaa atccattctc tatcttaatc gtcaccagac     840
tgaagagtgg aagggatgga tgcaggttct atttcttatg tatcattact ttgctgcggc     900
tgagatatat aatgcaatca gggttttcat tgctgcctac gtctggatga ctgggtttgg     960
gaacttctct tattactata tcagaaagga tttctcccta gcacgattta ctcagatgat    1020
gtggcgtctt aacttatttg tggcgtttag ctgcattatt ctcaataatg attatatgct    1080
gtactacatc tgtccaatgc acactctgtt cactcttatg gtgtatggag cccttggtat    1140
cttcagtcga tataacgaaa taccatcagt aatggctttg aagattgctt catgctttct    1200
cgtggttatc gtgatgtggg agattcctgg cgttttgag attttctgga gtcctttaac    1260
attcttactg ggatacactg atccagctaa accagaacta ccactttac atgaatggca    1320 cttcagatca ggacttgacc gctacatatg gatcattgga atgatatatg cctatttcca    1380
tcccactgta gagagatgga tggagaaatt ggaggagtgt gatgccaaga gaaagatgtc    1440
aataaagaca agcataattg caatttcctc atttgttggt tacctatggt atgaatacat    1500
atacaagctt gacaaggtta catacaacaa atatcatccc tacacatcgt ggattccaat    1560
```

```
aaccgtctac atctgtctgc gaaattctac acaacagctg cgtaatttct ccatgacact   1620
atttgcgtgg ctcggcaaga ttactctgga aacctatatt tctcagtttc acatctggtt   1680
aagatcgaat gtgccaaatg gacagcctaa gtggctatta tgcattattc cagaataccc   1740
aatgctcaac ttcatgctcg tcacggccat ctatgtcttg gtgtcccacc gacttttcga   1800
gcttacaaac acgttaaagt ctgttttcat accaacaaaa gacgacaaga ggctgctcca   1860
caatgttctc gctggagctg ccatctcgtt ctgtttatat ttaacatctc tcattcttct   1920
ccagatccca cactaaccat gagggactag aaacatgttg aaaaacatga atctaaagct   1980
gcacagaggt ttctatgtga aacttgctaa aatagataca acacacatct catatcgaca   2040
ataaaaattt gttttcaaag atcagtattt tttgaagctt gccaagtgaa gcatcttttg   2100
ggtaattaga accagagaag cttcaaaaaa tggcttagag tgaagcatct tgtggcattt   2160
cgacggcatc atcttaggac gacttatctt gttcgttttc tttctcgtct ctgttgtaat   2220
tttgctataa gtttctcata tatagtttca ttttgtcttt tgttcgtccg tatttggtag   2280
tttgtccaaa tacagaacat atgaatttta caagagtgga tatttcaatt caattgagtc   2340
ttcagataaa acgccaacac agttagaaaa aagaggttc gatttctata caagatacc    2400 acaaggaaa gttcacaaat ttacatagaa tagaccacaa acaaactctc tttctctgct   2460
ctcattcaca taataagcag ccgctcactt tccggggacg aagttggtgg cgaaggccca   2520
agcgttgttg ttgactgggt cggccaaatg gtcggcgagg ttctccaaag gtcccttttcc   2580 ggtgacgatg gcttgaacga agaatccaaa catagagaac atagccaacc ttccgttctt   2640
gagctccttc accttcaact ctgcgaaagc ctcggggtca gtagcgaggc ccaatgggtc   2700
gaagctgcca cctgggtaaa gcaagtcctc tgcttctccc aatggaccat ctccggcgac   2760
tctgtagcct tcaacaatgc tctgagcgtg gaccaagctc gggttgccca agtagtccaa   2820
tcctccgtcg ctgaagatct gtgaaccggc cttgaaccaa accgcttctc cgaacttcac   2880
tccgttccta gccaatagct cagggaaaac gcagcctagg gctccgagca tggcccatct   2940
gctgtggata acttctagct cacggttcct ggcgaaggtc tctgggtcgg cggatagacc   3000
agcggtgtcc catccgtagt caccggggaa ctcaccggta aggtagctcg ggggctcgcc   3060
ggagaatgga cccaagtact tgactcggtc agatccgtac catgggctgc ctgatggacc   3120
ctttggcttg gcgacagtct tcctcatggt cacacggccg cttccgagga catctgatgc   3180
ggcaggcttc acagcctttc cggcgaaggc aggggaggac aaagccatgg ttgaggaagc   3240
cattataatc tttgtttttg tgttttcttt tttttggttg tgactggtga gagtgattg    3299
```

<210> SEQ ID NO 18
<211> LENGTH: 540
<212> TYPE: PRT
<213> ORGANISM: Arabidopsis thaliana

<400> SEQUENCE: 18

```
Met Ala Asp Ser Gln Pro Ile Thr Pro Gly Gln Val Ser Phe Leu Leu
1               5                   10                  15

Gly Val Ile Pro Val Phe Ile Ala Trp Ile Tyr Ser Glu Phe Leu Glu
            20                  25                  30

Tyr Lys Arg Ser Ser Leu His Ser Lys Val His Ser Asp Asn Asn Leu
        35                  40                  45

Val Glu Leu Gly Glu Val Lys Asn Lys Glu Asp Glu Gly Val Val Leu
    50                  55                  60

Leu Glu Gly Gly Leu Pro Arg Ser Val Ser Thr Lys Phe Tyr Asn Ser
```

```
                65                  70                  75                  80
            Pro Ile Lys Thr Asn Leu Ile Arg Phe Leu Thr Leu Glu Asp Ser Phe
                            85                  90                  95
            Leu Ile Glu Asn Arg Ala Thr Leu Arg Ala Met Ala Glu Phe Gly Ala
                           100                 105                 110
            Ile Leu Phe Tyr Phe Tyr Ile Ser Asp Arg Thr Ser Leu Leu Gly Glu
                           115                 120                 125
            Ser Lys Lys Asn Tyr Asn Arg Asp Leu Phe Leu Phe Leu Tyr Cys Leu
                           130                 135                 140
            Leu Ile Ile Val Ser Ala Met Thr Ser Leu Lys Lys His Asn Asp Lys
            145                 150                 155                 160
            Ser Pro Ile Thr Gly Lys Ser Ile Leu Tyr Leu Asn Arg His Gln Thr
                           165                 170                 175
            Glu Glu Trp Lys Gly Trp Met Gln Val Leu Phe Leu Met Tyr His Tyr
                           180                 185                 190
            Phe Ala Ala Ala Glu Ile Tyr Asn Ala Ile Arg Val Phe Ile Ala Ala
                           195                 200                 205
            Tyr Val Trp Met Thr Gly Phe Gly Asn Phe Ser Tyr Tyr Tyr Ile Arg
                           210                 215                 220
            Lys Asp Phe Ser Leu Ala Arg Phe Thr Gln Met Met Trp Arg Leu Asn
            225                 230                 235                 240
            Leu Phe Val Ala Phe Ser Cys Ile Ile Leu Asn Asn Asp Tyr Met Leu
                           245                 250                 255
            Tyr Tyr Ile Cys Pro Met His Thr Leu Phe Thr Leu Met Val Tyr Gly
                           260                 265                 270
            Ala Leu Gly Ile Phe Ser Arg Tyr Asn Glu Ile Pro Ser Val Met Ala
                           275                 280                 285
            Leu Lys Ile Ala Ser Cys Phe Leu Val Val Ile Val Met Trp Glu Ile
                           290                 295                 300
            Pro Gly Val Phe Glu Ile Phe Trp Ser Pro Leu Thr Phe Leu Leu Gly
            305                 310                 315                 320
            Tyr Thr Asp Pro Ala Lys Pro Glu Leu Pro Leu Leu His Glu Trp His
                           325                 330                 335
            Phe Arg Ser Gly Leu Asp Arg Tyr Ile Trp Ile Ile Gly Met Ile Tyr
                           340                 345                 350
            Ala Tyr Phe His Pro Thr Val Glu Arg Trp Met Glu Lys Leu Glu Glu
                           355                 360                 365
            Cys Asp Ala Lys Arg Lys Met Ser Ile Lys Thr Ser Ile Ile Ala Ile
                           370                 375                 380
            Ser Ser Phe Val Gly Tyr Leu Trp Tyr Glu Tyr Ile Tyr Lys Leu Asp
            385                 390                 395                 400
            Lys Val Thr Tyr Asn Lys Tyr His Pro Tyr Thr Ser Trp Ile Pro Ile
                           405                 410                 415
            Thr Val Tyr Ile Cys Leu Arg Asn Ser Thr Gln Gln Leu Arg Asn Phe
                           420                 425                 430
            Ser Met Thr Leu Phe Ala Trp Leu Gly Lys Ile Thr Leu Glu Thr Tyr
                           435                 440                 445
            Ile Ser Gln Phe His Ile Trp Leu Arg Ser Asn Val Pro Asn Gly Gln
                           450                 455                 460
            Pro Lys Trp Leu Leu Cys Ile Ile Pro Glu Tyr Pro Met Leu Asn Phe
            465                 470                 475                 480
            Met Leu Val Thr Ala Ile Tyr Val Leu Val Ser His Arg Leu Phe Glu
                           485                 490                 495
```

```
Leu Thr Asn Thr Leu Lys Ser Val Phe Ile Pro Thr Lys Asp Asp Lys
            500                 505                 510

Arg Leu Leu His Asn Val Leu Ala Gly Ala Ala Ile Ser Phe Cys Leu
            515                 520                 525

Tyr Leu Thr Ser Leu Ile Leu Leu Gln Ile Pro His
            530                 535                 540

<210> SEQ ID NO 19
<211> LENGTH: 3338
<212> TYPE: DNA
<213> ORGANISM: Arabidopsis thaliana

<400> SEQUENCE: 19
gaacggacca gaaaagagaa cattcgccaa accaaccaac aaccgtttgg gtgagcttga      60
cgagaacgac gtcgcacccg ccattttctc catccttgaa gcaacacctt cttcacttca     120
gatctcttct tcttcttctt cttcttcttc ttcttcttct ttgctcgcac cttccgtgct     180
attgtatttc tagggtttcg gatcctgtgc cttaccttag atccgacggt ggagtagaaa     240
tcactctccc tgtctcttcc cttctttttt gtttccagtt tttgattgaa gatcccttcg     300
tggatccact ataatggcgg attctcagcc aatcacgcct ggtcaggttt cgtttctact     360
cggagtcatt cctgtcttca tagcatggat ttactcagag tttctagagt ataagaggtc     420
ttcattgcac tctaaagttc attcagataa taatttggtt gaacttggtg aggtaaaaaa     480
caaggaagat gaaggagtag ttttacttga aggaggtctt ccaagatcag tctctacaaa     540
gttttataac tcacctatca aaacaaactt gattagattt ctgacgctgg aagactcttt     600
cttgattgaa aatcgagcaa ccttgagagc gatggctgag tttggggcta ttcttttttta    660
cttttatatt agtgatcgaa caagcttgct tggagagtct aaaaagaatt acaacagaga     720
tcttttcctc tttctctact gtcttctcat catagtttca gccatgacat ccttgaagaa     780
acacaatgac aaatcaccta aacaggaaaa atccattctc tatcttaatc gtcaccagac     840
tgaagagtgg aagggatgga tgcaggttct atttcttatg tatcattact ttgctgcggc     900
tgagatatat aatgcaatca gggttttcat tgctgcctac gtctggatga ctgggtttgg     960
gaacttctct tattactata tcagaaagga tttctcccta gcacgattta ctcagatgat    1020
gtggcgtctt aacttatttg tggcgtttag ctgcattatt ctcaataatg attatatgct    1080
gtactacatc tgtccaatgc acactctgtt cactcttatg gtgtatggag cccttggtat    1140
cttcagtcga tataacgaaa taccatcagt aatggctttg aagattgctt catgcttttct   1200
cgtggttatc gtgatgtggg agattcctgg cgttttttgag attttctgga gtcctttaac    1260
attcttactg ggatacactg atccagctaa accagaacta ccacttttac atgaatggca    1320
cttcagatca ggacttgacc gctacatatg gatcattgga atgatatatg cctatttcca    1380
tcccactgta gagagatgga tggagaaatt ggaggagtgt gatgccaaga gaaagatgtc    1440
aataaagaca agcataattg caatttcctc atttgttggt tacctatggt atgaatacat    1500
atacaagctt gacaaggtta catacaacaa atatcatccc tacacatcgt ggattccaat    1560
aaccgtctac atctgtctgc gaaattctac acaacagctg cgtaatttct ccatgacact    1620
atttgcgtgg ctcggcaaga ttactctgga aacctatatt tctcagtttc acatctggtt    1680
aagatcgaat gtgccaaatg gacagcctaa gtggctatta tgcattattc agaataccc     1740
aatgctcaac ttcatgctcg tcacggccat ctatgtcttg gtgtcccacc gacttttcga    1800
gcttacaaac acgttaaagt ctgttttcat accaacaaaa gacgcacaaga ggctgctcca   1860
caatgttctc gctggagctg ccatctcgtt ctgtttatat ttaacatctc tcattcttct    1920
```

```
ccagatccca cactaaccat gagggactag aaacatgttg aaaaacatga atctaaagct    1980
gcacagaggt ttctatgtga aacttgctaa aatagataca acacacatct catatcgaca    2040
ataaaaattt gttttcaaag atcagtattt tttgaagctt gccaagtgaa gcatcttttg    2100
ggtaattaga accagagaag cttcaaaaaa tggcttagag tgaagcatct tgtggcattt    2160
cgacggcatc atcttaggac gacttatctt gttcgttttc tttctcgtct ctgttgtaat    2220
tttgctataa gtttctcata tatagtttca ttttgtcttt tgttcgtccg tatttggtag    2280
tttgtccaaa tacagaacat atgaatttta caagagtgga tatttcaatt caattgagtc    2340
ttcagataaa acgccaacac agttagagaa aaagaggttc gatttctata caaagatacc    2400
acaaaggaaa gttcacaaat ttacatagaa tagaccacaa acaaactctc tttctctgct    2460
ctcattcaca taataagcag ccgctcactt tccggggacg aagttggtgg cgaaggccca    2520
agcgttgttg ttgactgggt cggccaaatg gtcggcgagg ttctccaaag gtccctttcc    2580
ggtgacgatg gcttgaacga agaatccaaa catagagaac atagccaacc ttccgttctt    2640
gagctccttc accttcaact ctgcgaaagc ctcggggtca gtagcgaggc ccaatgggtc    2700
gaagctgcca cctgggtaaa gcaagtcctc tgcttctccc aatggaccat ctccggcgac    2760
tctgtagcct tcaacagctc ccatgaggat aacttgagta gcccaaatgg ctaagatgct    2820
ctgagcgtgg accaagctcg ggttgcccaa gtagtccaat cctccgtcgc tgaagatctg    2880
tgaaccggcc ttgaaccaaa ccgcttctcc gaacttcact ccgttcctag ccaatagctc    2940
agggaaaacg cagcctaggg ctccgagcat ggcccatctg ctgtggataa cttctagctc    3000
acggttcctg gcgaaggtct ctgggtcggc ggatagacca gcggtgtccc atccgtagtc    3060
accggggaac tcaccggtaa ggtagctcgg gggctcgccg gagaatggac ccaagtactt    3120
gactcggtca gatccgtacc atgggctgcc tgatggaccc tttggcttgg cgacagtctt    3180
cctcatggtc acacggccgc ttccgaggac atctgatgcg gcaggcttca cagccttttcc   3240 ggcgaaggca ggggaggaca aagccatggt tgaggaagcc attataatct tgttttttgt    3300
gttttctttt ttttggttgt gactggtgag agtgattg                             3338
```

<210> SEQ ID NO 20
<211> LENGTH: 540
<212> TYPE: PRT
<213> ORGANISM: Arabidopsis thaliana

<400> SEQUENCE: 20

```
Met Ala Asp Ser Gln Pro Ile Thr Pro Gly Gln Val Ser Phe Leu Leu
1               5                   10                  15

Gly Val Ile Pro Val Phe Ile Ala Trp Ile Tyr Ser Glu Phe Leu Glu
            20                  25                  30

Tyr Lys Arg Ser Ser Leu His Ser Lys Val His Ser Asp Asn Asn Leu
        35                  40                  45

Val Glu Leu Gly Glu Val Lys Asn Lys Glu Asp Gly Val Val Leu
    50                  55                  60

Leu Glu Gly Gly Leu Pro Arg Ser Val Ser Thr Lys Phe Tyr Asn Ser
65                  70                  75                  80

Pro Ile Lys Thr Asn Leu Ile Arg Phe Leu Thr Leu Glu Asp Ser Phe
                85                  90                  95

Leu Ile Glu Asn Arg Ala Thr Leu Arg Ala Met Ala Glu Phe Gly Ala
            100                 105                 110

Ile Leu Phe Tyr Phe Tyr Ile Ser Asp Arg Thr Ser Leu Leu Gly Glu
        115                 120                 125
```

-continued

Ser Lys Lys Asn Tyr Asn Arg Asp Leu Phe Leu Phe Leu Tyr Cys Leu
    130                 135                 140

Leu Ile Ile Val Ser Ala Met Thr Ser Leu Lys Lys His Asn Asp Lys
145                 150                 155                 160

Ser Pro Ile Thr Gly Lys Ser Ile Leu Tyr Leu Asn Arg His Gln Thr
                165                 170                 175

Glu Glu Trp Lys Gly Trp Met Gln Val Leu Phe Leu Met Tyr His Tyr
                180                 185                 190

Phe Ala Ala Ala Glu Ile Tyr Asn Ala Ile Arg Val Phe Ile Ala Ala
                195                 200                 205

Tyr Val Trp Met Thr Gly Phe Gly Asn Phe Ser Tyr Tyr Ile Arg
                210                 215                 220

Lys Asp Phe Ser Leu Ala Arg Phe Thr Gln Met Met Trp Arg Leu Asn
225                 230                 235                 240

Leu Phe Val Ala Phe Ser Cys Ile Ile Leu Asn Asn Asp Tyr Met Leu
                245                 250                 255

Tyr Tyr Ile Cys Pro Met His Thr Leu Phe Thr Leu Met Val Tyr Gly
                260                 265                 270

Ala Leu Gly Ile Phe Ser Arg Tyr Asn Glu Ile Pro Ser Val Met Ala
                275                 280                 285

Leu Lys Ile Ala Ser Cys Phe Leu Val Val Ile Val Met Trp Glu Ile
                290                 295                 300

Pro Gly Val Phe Glu Ile Phe Trp Ser Pro Leu Thr Phe Leu Leu Gly
305                 310                 315                 320

Tyr Thr Asp Pro Ala Lys Pro Glu Leu Pro Leu Leu His Glu Trp His
                325                 330                 335

Phe Arg Ser Gly Leu Asp Arg Tyr Ile Trp Ile Gly Met Ile Tyr
                340                 345                 350

Ala Tyr Phe His Pro Thr Val Glu Arg Trp Met Glu Lys Leu Glu Glu
                355                 360                 365

Cys Asp Ala Lys Arg Lys Met Ser Ile Lys Thr Ser Ile Ile Ala Ile
                370                 375                 380

Ser Ser Phe Val Gly Tyr Leu Trp Tyr Glu Tyr Ile Tyr Lys Leu Asp
385                 390                 395                 400

Lys Val Thr Tyr Asn Lys Tyr His Pro Tyr Thr Ser Trp Ile Pro Ile
                405                 410                 415

Thr Val Tyr Ile Cys Leu Arg Asn Ser Thr Gln Gln Leu Arg Asn Phe
                420                 425                 430

Ser Met Thr Leu Phe Ala Trp Leu Gly Lys Ile Thr Leu Glu Thr Tyr
                435                 440                 445

Ile Ser Gln Phe His Ile Trp Leu Arg Ser Asn Val Pro Asn Gly Gln
                450                 455                 460

Pro Lys Trp Leu Leu Cys Ile Ile Pro Glu Tyr Pro Met Leu Asn Phe
465                 470                 475                 480

Met Leu Val Thr Ala Ile Tyr Val Leu Val Ser His Arg Leu Phe Glu
                485                 490                 495

Leu Thr Asn Thr Leu Lys Ser Val Phe Ile Pro Thr Lys Asp Asp Lys
                500                 505                 510

Arg Leu Leu His Asn Val Leu Ala Gly Ala Ile Ser Phe Cys Leu
                515                 520                 525

Tyr Leu Thr Ser Leu Ile Leu Leu Gln Ile Pro His
530                 535                 540

```
<210> SEQ ID NO 21
<211> LENGTH: 1936
<212> TYPE: DNA
<213> ORGANISM: Arabidopsis thaliana

<400> SEQUENCE: 21
gaacggacca gaaaagagaa cattcgccaa accaaccaac aaccgtttgg gtgagcttga      60
cgagaacgac gtcgcacccg ccattttctc catccttgaa gcaacacctt cttcacttca     120
gatctcttct tcttcttctt cttcttcttc ttcttcttct ttgctcgcac cttccgtgct     180
attgtatttc tagggtttcg gatcctgtgc cttaccttag atccgacggt ggagtagaaa     240
tcactctccc tgtctcttcc cttcttttt gtttccagtt tttgattgaa gatcccttcg      300
tggatccact ataatggcgg attctcagcc aatcacgcct ggtcaggttt cgtttctact     360
cggagtcatt cctgtcttca tagcatggat ttactcagag tttctagagt ataagaggtc     420
ttcattgcac tctaaagttc attcagataa taatttggtt gaacttggtg aggtaaaaaa     480
caaggaagat gaaggagtag ttttacttga aggaggtctt ccaagatcag tctctacaaa     540
gttttataac tcacctatca aaacaaactt gattagattt ctgacgctgg aagactcttt     600
cttgattgaa aatcgagcaa ccttgagagc gatggctgag tttggggcta ttcttttta      660 cttttatatt agtgatcgaa caagcttgct tggagagtct aaaaagaatt acaacagaga     720
tcttttcctc tttctctact gtcttctcat catagtttca gccatgacat ccttgaagaa     780
acacaatgac aaatcaccta acaggaaa atccattctc tatcttaatc gtcaccagac      840
tgaagagtgg aagggatgga tgcaggttct atttcttatg tatcattact ttgctgcggc     900
tgagatatat aatgcaatca gggttttcat tgctgcctac gtctggatga ctgggtttgg     960
gaacttctct tattactata tcagaaagga tttctcccta gcacgattta ctcagatgat    1020
gtggcgtctt aacttatttg tggcgtttag ctgcattatt ctcaataatg attatatgct    1080
gtactacatc tgtccaatgc acactctgtt cactcttatg gtgtatggag cccttggtat    1140
cttcagtcga tataacgaaa taccatcagt aatggctttg aagattgctt catgctttct    1200
cgtggttatc gtgatgtggg agattcctgg cgttttttgag attttctgga gtccttaac    1260 attcttactg ggatacactg atccagctaa accagaacta ccacttttac atgaatggca    1320
cttcagatca ggacttgacc gctacatatg gatcattgga atgatatatg cctatttcca    1380
tcccactgta gagagatgga tggagaaatt ggaggagtgt gatgccaaga gaaagatgtc    1440
aataaagaca agcataattg caatttcctc atttgttggt tacctatggt atgaatacat    1500
atacaagctt gacaaggtta catacaacaa atatcatccc tacacatcgt ggattccaat    1560
aaccgtctac atctgtctgc gaaattctac acaacagctg cgtaatttct ccatgacact    1620
atttgcgtgg ctcggcaaga ttactctgga aacctatatt tctcagtttc acatctggtt    1680
aagatcgaat gtgccaaatg gacagcctaa gtggctatta tgcattattc cagaataccc    1740
aatgctcaac ttcatgctcg tcacggccat ctatgtcttg gtgtcccacc gacttttcga    1800
gcttacaaac acgttaaagt ctgttttcat accaacaaaa gacgacaaga ggctgctcca    1860
caatgttctc gctggagctg ccatctcgtt ctgtttatat ttaacatctc tcattcttct    1920
ccagatccca cactaa                                                   1936

<210> SEQ ID NO 22
<211> LENGTH: 540
<212> TYPE: PRT
<213> ORGANISM: Arabidopsis thaliana

<400> SEQUENCE: 22
```

-continued

```
Met Ala Asp Ser Gln Pro Ile Thr Pro Gly Gln Val Ser Phe Leu Leu
1               5                   10                  15

Gly Val Ile Pro Val Phe Ile Ala Trp Ile Tyr Ser Glu Phe Leu Glu
            20                  25                  30

Tyr Lys Arg Ser Ser Leu His Ser Lys Val His Ser Asp Asn Asn Leu
            35                  40                  45

Val Glu Leu Gly Glu Val Lys Asn Lys Glu Asp Gly Val Val Leu
50                  55                  60

Leu Glu Gly Gly Leu Pro Arg Ser Val Ser Thr Lys Phe Tyr Asn Ser
65                  70                  75                  80

Pro Ile Lys Thr Asn Leu Ile Arg Phe Leu Thr Leu Glu Asp Ser Phe
                85                  90                  95

Leu Ile Glu Asn Arg Ala Thr Leu Arg Ala Met Ala Glu Phe Gly Ala
                100                 105                 110

Ile Leu Phe Tyr Phe Tyr Ile Ser Asp Arg Thr Ser Leu Leu Gly Glu
            115                 120                 125

Ser Lys Lys Asn Tyr Asn Arg Asp Leu Phe Leu Phe Leu Tyr Cys Leu
            130                 135                 140

Leu Ile Ile Val Ser Ala Met Thr Ser Leu Lys Lys His Asn Asp Lys
145                 150                 155                 160

Ser Pro Ile Thr Gly Lys Ser Ile Leu Tyr Leu Asn Arg His Gln Thr
                165                 170                 175

Glu Glu Trp Lys Gly Trp Met Gln Val Leu Phe Leu Met Tyr His Tyr
                180                 185                 190

Phe Ala Ala Ala Glu Ile Tyr Asn Ala Ile Arg Val Phe Ile Ala Ala
            195                 200                 205

Tyr Val Trp Met Thr Gly Phe Gly Asn Phe Ser Tyr Tyr Tyr Ile Arg
210                 215                 220

Lys Asp Phe Ser Leu Ala Arg Phe Thr Gln Met Met Trp Arg Leu Asn
225                 230                 235                 240

Leu Phe Val Ala Phe Ser Cys Ile Ile Leu Asn Asn Asp Tyr Met Leu
            245                 250                 255

Tyr Tyr Ile Cys Pro Met His Thr Leu Phe Thr Leu Met Val Tyr Gly
            260                 265                 270

Ala Leu Gly Ile Phe Ser Arg Tyr Asn Glu Ile Pro Ser Val Met Ala
            275                 280                 285

Leu Lys Ile Ala Ser Cys Phe Leu Val Val Ile Val Met Trp Glu Ile
            290                 295                 300

Pro Gly Val Phe Glu Ile Phe Trp Ser Pro Leu Thr Phe Leu Leu Gly
305                 310                 315                 320

Tyr Thr Asp Pro Ala Lys Pro Glu Leu Pro Leu Leu His Glu Trp His
                325                 330                 335

Phe Arg Ser Gly Leu Asp Arg Tyr Ile Trp Ile Ile Gly Met Ile Tyr
                340                 345                 350

Ala Tyr Phe His Pro Thr Val Glu Arg Trp Met Glu Lys Leu Glu Glu
            355                 360                 365

Cys Asp Ala Lys Arg Lys Met Ser Ile Lys Thr Ser Ile Ile Ala Ile
            370                 375                 380

Ser Ser Phe Val Gly Tyr Leu Trp Tyr Glu Tyr Ile Tyr Lys Leu Asp
385                 390                 395                 400

Lys Val Thr Tyr Asn Lys Tyr His Pro Tyr Thr Ser Trp Ile Pro Ile
                405                 410                 415

Thr Val Tyr Ile Cys Leu Arg Asn Ser Thr Gln Gln Leu Arg Asn Phe
```

```
                 420               425               430
Ser Met Thr Leu Phe Ala Trp Leu Gly Lys Ile Thr Leu Glu Thr Tyr
            435               440               445

Ile Ser Gln Phe His Ile Trp Leu Arg Ser Asn Val Pro Asn Gly Gln
        450               455               460

Pro Lys Trp Leu Leu Cys Ile Ile Pro Glu Tyr Pro Met Leu Asn Phe
465               470               475               480

Met Leu Val Thr Ala Ile Tyr Val Leu Val Ser His Arg Leu Phe Glu
                485               490               495

Leu Thr Asn Thr Leu Lys Ser Val Phe Ile Pro Thr Lys Asp Asp Lys
            500               505               510

Arg Leu Leu His Asn Val Leu Ala Gly Ala Ala Ile Ser Phe Cys Leu
        515               520               525

Tyr Leu Thr Ser Leu Ile Leu Leu Gln Ile Pro His
    530               535               540

<210> SEQ ID NO 23
<211> LENGTH: 1312
<212> TYPE: DNA
<213> ORGANISM: Arabidopsis thaliana

<400> SEQUENCE: 23
aatcactctc accagtcaca accaaaaaaa agaaaacaca aaaacaaaga ttataatggc      60
ttcctcaacc atggctttgt cctcccctgc cttcgccgga aaggctgtga agcctgccgc     120
atcagatgtc ctcggaagcg ccgtgtgac catgaggaag actgtcgcca agccaaaggg     180
tccatcaggc agcccatggt acggatctga ccgagtcaag tacttgggtc cattctccgg     240 cgagccccg agctacctta ccggtgagtt ccccggtgac tacggatggg acaccgctgg     300
tctatccgcc gacccagaga ccttcgccag gaaccgtgag ctagaagtta ccacagcag      360 atgggccatg ctcggagccc taggctgcgt tttccctgag ctattggcta ggaacggagt     420
gaagttcgga gaagcggttt ggttcaaggc cggttcacag atcttcagcg acggaggatt     480
ggactacttg gcaacccga gcttggtcca cgctcagact gttgaaggct acagagtcgc     540
cggagatggt ccattgggag aagcagagga cttgctttac ccaggtggca gcttcgaccc     600
attgggcctc gctactgacc ccgaggcttt cgcagagttg aaggtgaagg agctcaagaa     660
cggaaggttg gctatgttct ctatgtttgg attcttcgtt caagccatcg tcaccggaaa     720
gggacctttg gagaacctcg ccgaccattt ggccgaccca gtcaacaaca acgcttgggc     780
cttcgccacc aacttcgtcc ccggaaagtg agcggctgct tattatgtga atgagagcag     840
agaaagagag tttgtttgtg gtctattcta tgtaaatttg tgaactttcc tttgtggtat     900
ctttgtatag aaatcgaacc tcttttttctc taactgtgtt ggcgtttat ctgaagactc     960 aattgaattg aaatatccac tcttgtaaaa ttcatatgtt ctgtatttgg acaaactacc    1020
aaatacggac gaacaaaaga caaatgaaa ctatatatga gaaacttata gcaaaattac     1080
aacagagacg agaaagaaaa cgaacaagat aagtcgtcct aagatgatgc cgtcgaaatg    1140
ccacaagatg cttcactcta agccattttt tgaagcttct ctggttctaa ttacccaaaa    1200
gatgcttcac ttggcaagct tcaaaaaata ctgatctttg aaaacaaatt tttattgtcg    1260
atatgagatg tgtgttgtat ctattttagc aagtttcaca tagaaacctc tg            1312

<210> SEQ ID NO 24
<211> LENGTH: 251
<212> TYPE: PRT
<213> ORGANISM: Arabidopsis thaliana
```

<400> SEQUENCE: 24

```
Met Ala Ser Ser Thr Met Ala Leu Ser Ser Pro Ala Phe Ala Gly Lys
1               5                   10                  15

Ala Val Lys Pro Ala Ala Ser Asp Val Leu Gly Ser Gly Arg Val Thr
            20                  25                  30

Met Arg Lys Thr Val Ala Lys Pro Lys Gly Pro Ser Gly Ser Pro Trp
        35                  40                  45

Tyr Gly Ser Asp Arg Val Lys Tyr Leu Gly Pro Phe Ser Gly Glu Pro
    50                  55                  60

Pro Ser Tyr Leu Thr Gly Glu Phe Pro Gly Asp Tyr Gly Trp Asp Thr
65                  70                  75                  80

Ala Gly Leu Ser Ala Asp Pro Glu Thr Phe Ala Arg Asn Arg Glu Leu
                85                  90                  95

Glu Val Ile His Ser Arg Trp Ala Met Leu Gly Ala Leu Gly Cys Val
            100                 105                 110

Phe Pro Glu Leu Leu Ala Arg Asn Gly Val Lys Phe Gly Glu Ala Val
        115                 120                 125

Trp Phe Lys Ala Gly Ser Gln Ile Phe Ser Asp Gly Gly Leu Asp Tyr
    130                 135                 140

Leu Gly Asn Pro Ser Leu Val His Ala Gln Thr Val Glu Gly Tyr Arg
145                 150                 155                 160

Val Ala Gly Asp Gly Pro Leu Gly Glu Ala Glu Asp Leu Leu Tyr Pro
                165                 170                 175

Gly Gly Ser Phe Asp Pro Leu Gly Leu Ala Thr Asp Pro Glu Ala Phe
            180                 185                 190

Ala Glu Leu Lys Val Lys Glu Leu Lys Asn Gly Arg Leu Ala Met Phe
        195                 200                 205

Ser Met Phe Gly Phe Phe Val Gln Ala Ile Val Thr Gly Lys Gly Pro
    210                 215                 220

Leu Glu Asn Leu Ala Asp His Leu Ala Asp Pro Val Asn Asn Asn Ala
225                 230                 235                 240

Trp Ala Phe Ala Thr Asn Phe Val Pro Gly Lys
                245                 250
```

<210> SEQ ID NO 25
<211> LENGTH: 1354
<212> TYPE: DNA
<213> ORGANISM: Arabidopsis thaliana

<400> SEQUENCE: 25

```
aatcactctc accagtcaca accaaaaaaa agaaaacaca aaaacaaaga ttataatggc      60
ttcctcaacc atggctttgt cctcccctgc cttcgccgga aaggctgtga agcctgccgc     120
atcagatgtc ctcggaagcg gccgtgtgac catgaggaag actgtcgcca agccaaaggg     180
tccatcaggc agcccatggt acggatctga ccgagtcaag tacttgggtc cattctccgg     240 cgagccccg agctacctta ccggtgagtt ccccggtgac tacggatggg acaccgctgg      300
tctatccgcc gacccagaga ccttcgccag gaaccgtgag ctagaagtta tccacagcag     360
atgggccatg ctcggagccc taggctgcgt tttccctgag ctattggcta ggaacggagt     420
gaagttcgga gaagcggttt ggttcaaggc cggttcacag atcttcagcg acggaggatt     480
ggactacttg ggcaacccga gcttggtcca cgctcagagc atcttagcca tttgggctac     540
tcaagttatc ctcatgggag ctgttgaagg ctacagagtc gccggagatg gtccattggg     600
agaagcagag gacttgcttt acccaggtgg cagcttcgac ccattgggcc tcgctactga     660
```

```
cccgaggct tcgcagagt tgaaggtgaa ggagctcaag aacgaaggt tggctatgtt    720 ctctatgttt ggattcttcg ttcaagccat cgtcaccgga aagggacctt tggagaacct    780
cgccgaccat ttggccgacc cagtcaacaa caacgcttgg gccttcgcca ccaacttcgt    840
ccccggaaag tgagcggctg cttattatgt gaatgagagc agagaaagag agtttgtttg    900
tggtctattc tatgtaaatt tgtgaacttt cctttgtggt atctttgtat agaaatcgaa    960 cctcttttc tctaactgtg ttggcgtttt atctgaagac tcaattgaat tgaaatatcc   1020
actcttgtaa aattcatatg ttctgtattt ggacaaacta ccaaatacgg acgaacaaaa   1080
gacaaaatga aactatatat gagaaactta tagcaaaatt acaacagaga cgagaaagaa   1140
aacgaacaag ataagtcgtc ctaagatgat gccgtcgaaa tgccacaaga tgcttcactc   1200
taagccattt tttgaagctt ctctggttct aattacccaa aagatgcttc acttggcaag   1260
cttcaaaaaa tactgatctt tgaaaacaaa tttttattgt cgatatgaga tgtgtgttgt   1320 atctattta gcaagtttca catagaaacc tctg                                1354

<210> SEQ ID NO 26
<211> LENGTH: 265
<212> TYPE: PRT
<213> ORGANISM: Arabidopsis thaliana

<400> SEQUENCE: 26

Met Ala Ser Ser Thr Met Ala Leu Ser Ser Pro Ala Phe Ala Gly Lys
1               5                   10                  15

Ala Val Lys Pro Ala Ala Ser Asp Val Leu Gly Ser Gly Arg Val Thr
            20                  25                  30

Met Arg Lys Thr Val Ala Lys Pro Lys Gly Pro Ser Gly Ser Pro Trp
        35                  40                  45

Tyr Gly Ser Asp Arg Val Lys Tyr Leu Gly Pro Phe Ser Gly Glu Pro
    50                  55                  60

Pro Ser Tyr Leu Thr Gly Glu Phe Pro Gly Asp Tyr Gly Trp Asp Thr
65                  70                  75                  80

Ala Gly Leu Ser Ala Asp Pro Glu Thr Phe Ala Arg Asn Arg Glu Leu
                85                  90                  95

Glu Val Ile His Ser Arg Trp Ala Met Leu Gly Ala Leu Gly Cys Val
            100                 105                 110

Phe Pro Glu Leu Leu Ala Arg Asn Gly Val Lys Phe Gly Glu Ala Val
        115                 120                 125

Trp Phe Lys Ala Gly Ser Gln Ile Phe Ser Asp Gly Gly Leu Asp Tyr
    130                 135                 140

Leu Gly Asn Pro Ser Leu Val His Ala Gln Ser Ile Leu Ala Ile Trp
145                 150                 155                 160

Ala Thr Gln Val Ile Leu Met Gly Ala Val Glu Gly Tyr Arg Val Ala
                165                 170                 175

Gly Asp Gly Pro Leu Gly Glu Ala Glu Asp Leu Leu Tyr Pro Gly Gly
            180                 185                 190

Ser Phe Asp Pro Leu Gly Leu Ala Thr Asp Pro Glu Ala Phe Ala Glu
        195                 200                 205

Leu Lys Val Lys Glu Leu Lys Asn Gly Arg Leu Ala Met Phe Ser Met
    210                 215                 220

Phe Gly Phe Phe Val Gln Ala Ile Val Thr Gly Lys Gly Pro Leu Glu
225                 230                 235                 240

Asn Leu Ala Asp His Leu Ala Asp Pro Val Asn Asn Ala Trp Ala
                245                 250                 255
```

```
Phe Ala Thr Asn Phe Val Pro Gly Lys
            260                 265
```

<210> SEQ ID NO 27
<211> LENGTH: 1008
<212> TYPE: DNA
<213> ORGANISM: Arabidopsis thaliana

<400> SEQUENCE: 27

| | | | | | |
|---|---|---|---|---|---|
| atccaatttc | atcacatctt | attaactaaa | gagccttta | cttgcgccac | actctcaccg | 60 |
| caatggccgc | ctcgacaatg | gctctctcct | ctcctgcttt | gaccggaaag | gccgttaagc | 120 |
| tatccccggc | ggcctccgaa | gtatttggaa | ccggccgaat | caccatgcgc | aaagcctcca | 180 |
| agcccaccgg | tccatccggc | agcccatggt | acggatccga | ccgagtcaag | tacttgggtc | 240 |
| cattctccgg | tgagcctccg | agctacctca | ctggagagtt | ccccggtgat | tacgggtggg | 300 |
| acactgccgg | tctatccgcc | gatcccgaga | ccttcgctag | gaaccgtgag | ctagaagtta | 360 |
| tccacagcag | atgggccatg | ctcggagccc | taggctgcgt | tttccctgag | ctattggcta | 420 |
| ggaacggagt | gaagttcgga | gaagcggttt | ggttcaaggc | tggttcacag | atcttcagcg | 480 |
| acggaggatt | ggactacttg | gcaacccga | gcttggtcca | cgctcagagc | atcttagcca | 540 |
| tttgggctac | tcaagttatc | ctcatgggag | ctgttgaggg | ctacagagtc | gccgagatg | 600 |
| gtccattggg | agaagcagag | gacttgcttt | acccaggtgg | gagcttcgac | ccattgggcc | 660 |
| tcgctactga | ccccgaggct | ttcgcggagt | tgaaggtgaa | ggagctcaag | aacggaaggt | 720 |
| tggctatgtt | ctctatgttt | ggattcttcg | ttcaggccat | tgtcaccgga | aagggaccgt | 780 |
| tggagaacct | cgcggaccac | ttggctgatc | cagtcaacaa | caatgcatgg | gccttcgcta | 840 |
| ccaacttcgt | ccccggaaag | tgagtttaat | ttgtgatcga | gttgtgtgta | tccggtttgt | 900 |
| tgcatcttgg | aaatgtgatg | cagatttcat | atccttgtaaa | ttactttgta | tgtgtgtgaa | 960 |
| atatttaaga | agctttatga | tattgatgga | tcagtcactt | actattta | | 1008 |

<210> SEQ ID NO 28
<211> LENGTH: 266
<212> TYPE: PRT
<213> ORGANISM: Arabidopsis thaliana

<400> SEQUENCE: 28

```
Met Ala Ala Ser Thr Met Ala Leu Ser Ser Pro Ala Leu Thr Gly Lys
1               5                   10                  15

Ala Val Lys Leu Ser Pro Ala Ala Ser Glu Val Phe Gly Thr Gly Arg
            20                  25                  30

Ile Thr Met Arg Lys Ala Ser Lys Pro Thr Gly Pro Ser Gly Ser Pro
        35                  40                  45

Trp Tyr Gly Ser Asp Arg Val Lys Tyr Leu Gly Pro Phe Ser Gly Glu
    50                  55                  60

Pro Pro Ser Tyr Leu Thr Gly Glu Phe Pro Gly Asp Tyr Gly Trp Asp
65                  70                  75                  80

Thr Ala Gly Leu Ser Ala Asp Pro Glu Thr Phe Ala Arg Asn Arg Glu
                85                  90                  95

Leu Glu Val Ile His Ser Arg Trp Ala Met Leu Gly Ala Leu Gly Cys
            100                 105                 110

Val Phe Pro Glu Leu Leu Ala Arg Asn Gly Val Lys Phe Gly Glu Ala
        115                 120                 125

Val Trp Phe Lys Ala Gly Ser Gln Ile Phe Ser Asp Gly Gly Leu Asp
    130                 135                 140
```

```
Tyr Leu Gly Asn Pro Ser Leu Val His Ala Gln Ser Ile Leu Ala Ile
145                 150                 155                 160

Trp Ala Thr Gln Val Ile Leu Met Gly Ala Val Glu Gly Tyr Arg Val
                165                 170                 175

Ala Gly Asp Gly Pro Leu Gly Glu Ala Glu Asp Leu Leu Tyr Pro Gly
            180                 185                 190

Gly Ser Phe Asp Pro Leu Gly Leu Ala Thr Asp Pro Glu Ala Phe Ala
        195                 200                 205

Glu Leu Lys Val Lys Glu Leu Lys Asn Gly Arg Leu Ala Met Phe Ser
    210                 215                 220

Met Phe Gly Phe Phe Val Gln Ala Ile Val Thr Gly Lys Gly Pro Leu
225                 230                 235                 240

Glu Asn Leu Ala Asp His Leu Ala Asp Pro Val Asn Asn Asn Ala Trp
                245                 250                 255

Ala Phe Ala Thr Asn Phe Val Pro Gly Lys
                260                 265

<210> SEQ ID NO 29
<211> LENGTH: 519
<212> TYPE: DNA
<213> ORGANISM: Arabidopsis thaliana

<400> SEQUENCE: 29
atgggtcgga gaaagatcaa gatggagatg gttcaggaca tgaacacacg acaggttacc      60
ttttcaaaac ggaggactgg tttgttcaag aaggcgagcg agttagccac gctctgcaac     120
gctgagttgg gcatcgttgt cttttcacca ggaggcaagc ctttctccta cgggaaaccg     180
aatcttgatt ctgttgcaga gcgattcatg agagaatatg atgattcaga cagtggcgat     240
gaagaaaaaa gtggtaatta caggcctaaa ctgaagaggc tgagtgaacg tctcgatttg     300
ctcaaccaag aggttgaagc tgagaaggaa cgaggcgaga gagtcagga gaagcttgaa      360 tctgctgggg atgagagatt caaggagtcc attgagacgc ttaccctcga tgaactcaat     420
gaatacaaag ataggcttca gacagtccat ggtaggattg aaggtcaagt caatcacttg     480
caggcttcgt cttgcctcat gcttctctcc agaaaatag                            519

<210> SEQ ID NO 30
<211> LENGTH: 172
<212> TYPE: PRT
<213> ORGANISM: Arabidopsis thaliana

<400> SEQUENCE: 30

Met Gly Arg Arg Lys Ile Lys Met Glu Met Val Gln Asp Met Asn Thr
1               5                   10                  15

Arg Gln Val Thr Phe Ser Lys Arg Arg Thr Gly Leu Phe Lys Lys Ala
                20                  25                  30

Ser Glu Leu Ala Thr Leu Cys Asn Ala Glu Leu Gly Ile Val Val Phe
            35                  40                  45

Ser Pro Gly Gly Lys Pro Phe Ser Tyr Gly Lys Pro Asn Leu Asp Ser
        50                  55                  60

Val Ala Glu Arg Phe Met Arg Glu Tyr Asp Asp Ser Asp Ser Gly Asp
65                  70                  75                  80

Glu Glu Lys Ser Gly Asn Tyr Arg Pro Lys Leu Lys Arg Leu Ser Glu
                85                  90                  95

Arg Leu Asp Leu Leu Asn Gln Glu Val Glu Ala Glu Lys Glu Arg Gly
            100                 105                 110
```

```
Glu Lys Ser Gln Glu Lys Leu Glu Ser Ala Gly Asp Glu Arg Phe Lys
        115                 120                 125

Glu Ser Ile Glu Thr Leu Thr Leu Asp Glu Leu Asn Glu Tyr Lys Asp
    130                 135                 140

Arg Leu Gln Thr Val His Gly Arg Ile Glu Gly Gln Val Asn His Leu
145                 150                 155                 160

Gln Ala Ser Ser Cys Leu Met Leu Leu Ser Arg Lys
        165                 170
```

<210> SEQ ID NO 31
<211> LENGTH: 685
<212> TYPE: DNA
<213> ORGANISM: Arabidopsis thaliana

<400> SEQUENCE: 31

```
aagaggcagc gaacgaaagt tcgattccga gaaagtgaga gaaaatgacg aagagagctc    60
ccaagtcagg gcctttgtct ccgtcgtgca gcggaggctc tagtcggaac ttagagttgg   120
ctgtgaagtc aagtgaaggt gcaaggaggt ctacaagact gagacttcag cctttgagaa   180
agccaaagac aagccccaag aagaaacccg ttaaactcca aacgaagatg cccaagaaac   240
ctgccactgc tttcttcttt ttcctggatg atttccggaa gcaatatcaa gaggagaatc   300
cagatgtcaa gtccatgcgc gaggttattg ggaagacatg tggagagaaa tggaaaacaa   360
tgacttacga ggaaaaggta agtattatg atatagctac tgagaagagg gaagaatttc   420
accgagcaat gacagaatat accaagagaa tggaatcagg tgcccacgat gaatcagaga   480
ccgactcaga ctattctgaa tagattactt tttagtttct accacattag aaacattgtt   540
ctaagccttc taggatgggt tgtatatcg gtgatattta agagtttctg tttcgttttt   600
gagatcattc tttcactgat actcatgttt ctgtggattg catttggaga tcaatgaata   660
ctaaccagtt tcttgagtgg ttgcc                                          685
```

<210> SEQ ID NO 32
<211> LENGTH: 152
<212> TYPE: PRT
<213> ORGANISM: Arabidopsis thaliana

<400> SEQUENCE: 32

```
Met Thr Lys Arg Ala Pro Lys Ser Gly Pro Leu Ser Pro Ser Cys Ser
1               5                   10                  15

Gly Gly Ser Ser Arg Asn Leu Glu Leu Ala Val Lys Ser Ser Glu Gly
            20                  25                  30

Ala Arg Arg Ser Thr Arg Leu Arg Leu Gln Pro Leu Arg Lys Pro Lys
        35                  40                  45

Thr Ser Pro Lys Lys Pro Val Lys Leu Gln Thr Lys Met Pro Lys
    50                  55                  60

Lys Pro Ala Thr Ala Phe Phe Phe Phe Leu Asp Asp Phe Arg Lys Gln
65                  70                  75                  80

Tyr Gln Glu Glu Asn Pro Asp Val Lys Ser Met Arg Glu Val Ile Gly
                85                  90                  95

Lys Thr Cys Gly Glu Lys Trp Lys Thr Met Thr Tyr Glu Glu Lys Val
            100                 105                 110

Lys Tyr Tyr Asp Ile Ala Thr Glu Lys Arg Glu Phe His Arg Ala
        115                 120                 125

Met Thr Glu Tyr Thr Lys Arg Met Glu Ser Gly Ala His Asp Glu Ser
    130                 135                 140

Glu Thr Asp Ser Asp Tyr Ser Glu
```

<210> SEQ ID NO 33
<211> LENGTH: 682
<212> TYPE: DNA
<213> ORGANISM: Arabidopsis thaliana

<400> SEQUENCE: 33

| | | |
|---|---|---|
| aagaggcagc gaacgaaagt tcgattccga gaaagtgaga gaaaatgacg aagagagctc | 60 |
| ccaagtcagg gcctttgtct ccgtcgtgca gcggaggctc tagtcggaac ttagagttgg | 120 |
| ctgtgaagtc aagtgaaggt gcaaggaggt ctacaagact gagacttcag cctttgagaa | 180 |
| agccaaagac aagccccaag aagaaacccg ttaaactcca aacgaagatg cccaagaaac | 240 |
| ctgccactgc tttcttcttt ttcctggatg atttccggaa gcaatatcaa gaggagaatc | 300 |
| cagatgtcaa gtccatgcgc gagattggga agacatgtgg agagaaatgg aaaacaatga | 360 |
| cttacgagga aaaggtaaag tattatgata tagctactga aagagggaa gaatttcacc | 420 |
| gagcaatgac agaatatacc aagagaatgg aatcaggtgc ccacgatgaa tcagagaccg | 480 |
| actcagacta ttctgaatag attacttttt agtttctacc acattagaaa cattgttcta | 540 |
| agccttctag gatgggtttg tatatcggtg atatttaaga gtttctgttt cgttttgag | 600 |
| atcattcttt cactgatact catgtttctg tggattgcat ttggagatca atgaatacta | 660 |
| accagtttct tgagtggttg cc | 682 |

<210> SEQ ID NO 34
<211> LENGTH: 151
<212> TYPE: PRT
<213> ORGANISM: Arabidopsis thaliana

<400> SEQUENCE: 34

Met Thr Lys Arg Ala Pro Lys Ser Gly Pro Leu Ser Pro Ser Cys Ser
1               5                   10                  15

Gly Gly Ser Ser Arg Asn Leu Glu Leu Ala Val Lys Ser Ser Glu Gly
            20                  25                  30

Ala Arg Arg Ser Thr Arg Leu Arg Leu Gln Pro Leu Arg Lys Pro Lys
        35                  40                  45

Thr Ser Pro Lys Lys Lys Pro Val Lys Leu Gln Thr Lys Met Pro Lys
    50                  55                  60

Lys Pro Ala Thr Ala Phe Phe Phe Phe Leu Asp Asp Phe Arg Lys Gln
65                  70                  75                  80

Tyr Gln Glu Glu Asn Pro Asp Val Lys Ser Met Arg Glu Ile Gly Lys
                85                  90                  95

Thr Cys Gly Glu Lys Trp Lys Thr Met Thr Tyr Glu Glu Lys Val Lys
            100                 105                 110

Tyr Tyr Asp Ile Ala Thr Glu Lys Arg Glu Glu Phe His Arg Ala Met
        115                 120                 125

Thr Glu Tyr Thr Lys Arg Met Glu Ser Gly Ala His Asp Glu Ser Glu
    130                 135                 140

Thr Asp Ser Asp Tyr Ser Glu
145                 150

<210> SEQ ID NO 35
<211> LENGTH: 921
<212> TYPE: DNA
<213> ORGANISM: Arabidopsis thaliana

<400> SEQUENCE: 35

```
atgaacgacc tcttaaaggg ttcgttagag ttctccaggg atcgctctaa tagaagcgat    60
attgagtcag gacatggccc tggtaactct ggagatctcg ggctctctgg tttcttcaaa   120
aaggtccagg aaatcgaaaa gcaatatgag aagcttgaca agcatctcaa caagcttcag   180
ggggcacatg aggagactaa agccgtcacc aaggctcctg caatgaaatc aatcaagcaa   240
aggatggaga gagatgttga tgaagtggga agaatttctc gtttcatcaa aggaaagatc   300
gaggaactgg accgagagaa tctggagaac cggactaaac cggggttgtgg gaaaggaaca   360 ggtgtagaca gaacaagaac agccacaact attgcggtga agaagaaatt taaggacaag   420
atatctgaat ccaaactcct aagacaaaac attcaacaag aatacagaga agttgtagag   480
aggcgtgtgt ttacagtgac tggccaacga gctgatgaag aggcaattga tagattgatt   540
gaaactggag acagtgagca aatttttccag aaagcaatca gggagcaagg acgaggacag   600
ataatggaca cactggctga gattcaggaa cgccatgacg ctgtcagaga tttagagaag   660
aaactccttg acctgcaaca ggtgtttctc gatatggccg tgctggtgga tgcacaggga   720
gagatgttag acaacataga gaatatggtc tcaagtgctg tggatcatgt tcaatccgga   780
aacaatcaac taacaaaggc agtaaaaagc cagaaaagtt caaggaaatg gatgtgcatt   840
gccatcctta tccttcttat cattattatc attactgtca tctctgttct caaaccatgg   900
acacagaaaa atggtgccta a                                            921
```

<210> SEQ ID NO 36
<211> LENGTH: 306
<212> TYPE: PRT
<213> ORGANISM: Arabidopsis thaliana

<400> SEQUENCE: 36

```
Met Asn Asp Leu Leu Lys Gly Ser Leu Glu Phe Ser Arg Asp Arg Ser
 1               5                  10                  15

Asn Arg Ser Asp Ile Glu Ser Gly His Gly Pro Gly Asn Ser Gly Asp
             20                  25                  30

Leu Gly Leu Ser Gly Phe Phe Lys Lys Val Gln Glu Ile Glu Lys Gln
         35                  40                  45

Tyr Glu Lys Leu Asp Lys His Leu Asn Lys Leu Gln Gly Ala His Glu
     50                  55                  60

Glu Thr Lys Ala Val Thr Lys Ala Pro Ala Met Lys Ser Ile Lys Gln
 65                  70                  75                  80

Arg Met Glu Arg Asp Val Asp Glu Val Gly Arg Ile Ser Arg Phe Ile
                 85                  90                  95

Lys Gly Lys Ile Glu Glu Leu Asp Arg Glu Asn Leu Glu Asn Arg Thr
            100                 105                 110

Lys Pro Gly Cys Gly Lys Gly Thr Gly Val Asp Arg Thr Arg Thr Ala
        115                 120                 125

Thr Thr Ile Ala Val Lys Lys Lys Phe Lys Asp Lys Ile Ser Glu Phe
    130                 135                 140

Gln Thr Leu Arg Gln Asn Ile Gln Gln Glu Tyr Arg Glu Val Val Glu
145                 150                 155                 160

Arg Arg Val Phe Thr Val Thr Gly Gln Arg Ala Asp Glu Glu Ala Ile
                165                 170                 175

Asp Arg Leu Ile Glu Thr Gly Asp Ser Glu Gln Ile Phe Gln Lys Ala
            180                 185                 190

Ile Arg Glu Gln Gly Arg Gly Gln Ile Met Asp Thr Leu Ala Glu Ile
        195                 200                 205

Gln Glu Arg His Asp Ala Val Arg Asp Leu Glu Lys Lys Leu Leu Asp
```

```
                210                 215                 220
Leu Gln Gln Val Phe Leu Asp Met Ala Val Leu Val Asp Ala Gln Gly
225                 230                 235                 240

Glu Met Leu Asp Asn Ile Glu Asn Met Val Ser Ser Ala Val Asp His
                245                 250                 255

Val Gln Ser Gly Asn Asn Gln Leu Thr Lys Ala Val Lys Ser Gln Lys
            260                 265                 270

Ser Ser Arg Lys Trp Met Cys Ile Ala Ile Leu Ile Leu Leu Ile Ile
        275                 280                 285

Ile Ile Ile Thr Val Ile Ser Val Leu Lys Pro Trp Thr Gln Lys Asn
    290                 295                 300

Gly Ala
305

<210> SEQ ID NO 37
<211> LENGTH: 2323
<212> TYPE: DNA
<213> ORGANISM: Arabidopsis thaliana

<400> SEQUENCE: 37
gtctgttaac aaagcaaccc tcgtcgcagg aaaaatcata aataaatttg cgttcttcga      60
tttctggaaa atctgtcagt gagtcttgtc tcctataagt ctccttctct cttcctcttg     120
atctgactct gaattaaatt caactacttc ctcctctgcc tggcacgggt ttttgtttg     180 ttttctcctg gaaagttcga agatgcgaga atctccagt tttttaatca gatcctaagc     240
gtgcttcgtt tcgaggctct ttcagtgatc atttacctcg tttgaccctg gatctcgcct    300
tgatttgggg ttcttagct ggggaaagag ctcgatttcg ggctggtgga agatggtgtt     360
taaatctaga ataaaatgga ttgcgctatt tgtgttgatc ttatcaatgg atctctggt    420 tgttcatctt tccatgacga agtcttcagg tgtacagttg gcgtattctg caagagataa     480
cctttggcag gattttgatt ctttgttagg tgcacaggat tttagaaata agcacttatg     540
gcggcctgtc aaatcgttag agaccttgca gccttatgcc aatccaagaa atagttatcc     600
tgcgcccagt tcgaaaaaca atggtttcat ttatgcaaag atatttggtg gatttgacaa    660
gattagatct tctatatgtg atcttgtcac catatccagg cttctaaatg ctactcttgt     720
cattccagag cttcaagaaa gtcttcgctc aaaaggcatt agcaacaagt tcaagagttt    780
ctcctatctt tatgatgaag agcagtttat agccttctct aaaaatgatg ttatagttat    840
gaagaccctc cctgagagct tgaaagccgc aagaaaaagg aatgagttcc ctcttttaa     900 gcccaaaaac tctgcgtcac caaaattta cctcgaggat gtgttgccaa agttaaagaa     960
agctaatgtt attggattga tcgtctctga tggggatgc ttgcagtcag ctttgcccgc    1020
ttcaatgcct gaacttcaaa gattaaggtg tagagttgcc ttccatgccc tccagcttcg    1080 tccagaaaatt caggtgctgg ccaaggagat ggttgacagg ttacgtaaat caggtcaacc    1140
tttcctagct tatcatcctg gcttagtaag ggagaaattg gcatatcatg ttgtgctga    1200 gcttttccag gatattcaca gtgaactcat ccaatatcgg cgtgctcaga tgatcaagca    1260
gaggtttatt ttagaagaac ttattgtaga ctcgcgcttg cgcagggata atggcttatg    1320
tcctctcatg ccagaagagg ttggaattct tttgaaagca ttgggttatt ctcaaaaagc    1380
gatcatatac ttggctggtt ctgaaatatt tggcggccaa cgggttttga tccctctacg    1440
tgccatgttc cctaatttag tggatcggac ttctttatgc agcacggagg aattatcaga    1500
attggttggt cctgagacac tcttccaga gaatacatat aaaatgcctc ctcgaaaaag    1560
```

```
cgataagcag ctcaaggaag agtggaacaa ggcaggtcct cgacctcgac ctctacctcc    1620
tcctccagac agacctatct accagcacga aaaagaagga tggtatggtt ggcttacaga    1680
gaatgacaca gaaccaagcc cttcgcctat ggatcttagg aatcaagcac acaggttact    1740
gtgggatgcc cttgattttg ctgtttctgt agaagctgat gtgttcttcc ctgggttcaa    1800
caacgatggt agtggatggc cagattttcc aagtttggtg atgggtcaaa ggctctatga    1860
aagaccctct tcacgaacat atagactgga caggaaagtt attcaagaac ttttcaacat    1920
tactcgtgag acatgtacc atcccaaccg taactggaca cttcgtgtga ggaaacatct    1980
taactcaagt ttgggtgaaa gtgggcttat caggcagtct atgttgtcga aacctaggtc    2040
gttcctttcg catccacttc ctgaatgctc atgcagaacc tcagcccttg aggattccag    2100
gcaaatacag agtgatgatg gtagatttct ctatggaggt gaggatgaat gccctaaatg    2160
gataaaatca gcgggagtgg aaaagagtaa aactgatgat ggtgatcagc ctgattatga    2220
ccatgacctt ctcgctgaac agtcagaaac tgaagaagaa tttgcaaaaa gtaaggtagc    2280
ttcagctttt gaccaagatg aagagtggga tcctaatgac tag                      2323
```

<210> SEQ ID NO 38
<211> LENGTH: 656
<212> TYPE: PRT
<213> ORGANISM: Arabidopsis thaliana

<400> SEQUENCE: 38

```
Met Val Phe Lys Ser Arg Ile Lys Trp Ile Ala Leu Phe Val Leu Ile
1               5                   10                  15

Leu Ser Met Gly Ser Leu Val Val His Leu Ser Met Thr Lys Ser Ser
            20                  25                  30

Gly Val Gln Leu Ala Tyr Ser Ala Arg Asp Asn Leu Trp Gln Asp Phe
        35                  40                  45

Asp Ser Leu Leu Gly Ala Gln Asp Phe Arg Asn Lys His Leu Trp Arg
    50                  55                  60

Pro Val Lys Ser Leu Glu Thr Leu Gln Pro Tyr Ala Asn Pro Arg Asn
65                  70                  75                  80

Ser Tyr Pro Ala Pro Ser Ser Lys Asn Asn Gly Phe Ile Tyr Ala Lys
                85                  90                  95

Ile Phe Gly Gly Phe Asp Lys Ile Arg Ser Ser Ile Cys Asp Leu Val
            100                 105                 110

Thr Ile Ser Arg Leu Leu Asn Ala Thr Leu Val Ile Pro Glu Leu Gln
        115                 120                 125

Glu Ser Leu Arg Ser Lys Gly Ile Ser Asn Lys Phe Lys Ser Phe Ser
    130                 135                 140

Tyr Leu Tyr Asp Glu Glu Gln Phe Ile Ala Phe Leu Lys Asn Asp Val
145                 150                 155                 160

Ile Val Met Lys Thr Leu Pro Glu Ser Leu Lys Ala Ala Arg Lys Arg
                165                 170                 175

Asn Glu Phe Pro Leu Phe Lys Pro Lys Asn Ser Ala Ser Pro Lys Phe
            180                 185                 190

Tyr Leu Glu Asp Val Leu Pro Lys Leu Lys Ala Asn Val Ile Gly
        195                 200                 205

Leu Ile Val Ser Asp Gly Gly Cys Leu Gln Ser Ala Leu Pro Ala Ser
    210                 215                 220

Met Pro Glu Leu Gln Arg Leu Arg Cys Arg Val Ala Phe His Ala Leu
225                 230                 235                 240

Gln Leu Arg Pro Glu Ile Gln Val Leu Ala Lys Glu Met Val Asp Arg
```

```
                   245                 250                 255
Leu Arg Lys Ser Gly Gln Pro Phe Leu Ala Tyr His Pro Gly Leu Val
                260                 265                 270
Arg Glu Lys Leu Ala Tyr His Gly Cys Ala Glu Leu Phe Gln Asp Ile
            275                 280                 285
His Ser Glu Leu Ile Gln Tyr Arg Arg Ala Gln Met Ile Lys Gln Arg
        290                 295                 300
Phe Ile Leu Glu Glu Leu Ile Val Asp Ser Arg Leu Arg Arg Asp Asn
305                 310                 315                 320
Gly Leu Cys Pro Leu Met Pro Glu Val Gly Ile Leu Leu Lys Ala
                325                 330                 335
Leu Gly Tyr Ser Gln Lys Ala Ile Ile Tyr Leu Ala Gly Ser Glu Ile
                340                 345                 350
Phe Gly Gly Gln Arg Val Leu Ile Pro Leu Arg Ala Met Phe Pro Asn
            355                 360                 365
Leu Val Asp Arg Thr Ser Leu Cys Ser Thr Glu Leu Ser Glu Leu
        370                 375                 380
Val Gly Pro Glu Thr Pro Leu Pro Glu Asn Thr Tyr Lys Met Pro Pro
385                 390                 395                 400
Arg Lys Ser Asp Lys Gln Leu Lys Glu Glu Trp Asn Lys Ala Gly Pro
                405                 410                 415
Arg Pro Arg Pro Leu Pro Pro Pro Asp Arg Pro Ile Tyr Gln His
                420                 425                 430
Glu Lys Glu Gly Trp Tyr Gly Trp Leu Thr Glu Asn Asp Thr Glu Pro
            435                 440                 445
Ser Pro Ser Pro Met Asp Leu Arg Asn Gln Ala His Arg Leu Leu Trp
        450                 455                 460
Asp Ala Leu Asp Phe Ala Val Ser Val Glu Ala Asp Val Phe Phe Pro
465                 470                 475                 480
Gly Phe Asn Asn Asp Gly Ser Gly Trp Pro Asp Phe Ser Ser Leu Val
                485                 490                 495
Met Gly Gln Arg Leu Tyr Glu Arg Pro Ser Ser Arg Thr Tyr Arg Leu
                500                 505                 510
Asp Arg Lys Val Ile Gln Glu Leu Phe Asn Ile Thr Arg Glu Asp Met
            515                 520                 525
Tyr His Pro Asn Arg Asn Trp Thr Leu Arg Val Arg Lys His Leu Asn
        530                 535                 540
Ser Ser Leu Gly Glu Ser Gly Leu Ile Arg Gln Ser Met Leu Ser Lys
545                 550                 555                 560
Pro Arg Ser Phe Leu Ser His Pro Leu Pro Glu Cys Ser Cys Arg Thr
                565                 570                 575
Ser Ala Leu Glu Asp Ser Arg Gln Ile Gln Ser Asp Asp Gly Arg Phe
            580                 585                 590
Leu Tyr Gly Gly Glu Asp Glu Cys Pro Lys Trp Ile Lys Ser Ala Gly
        595                 600                 605
Val Glu Lys Ser Lys Thr Asp Asp Gly Asp Gln Pro Asp Tyr Asp His
    610                 615                 620
Asp Leu Leu Ala Glu Gln Ser Glu Thr Glu Glu Phe Ala Lys Ser
625                 630                 635                 640
Lys Val Ala Ser Ala Phe Asp Gln Asp Glu Glu Trp Asp Pro Asn Asp
                645                 650                 655

<210> SEQ ID NO 39
<211> LENGTH: 291
```

```
<212> TYPE: DNA
<213> ORGANISM: Arabidopsis thaliana

<400> SEQUENCE: 39
atggctttgg taagaggttt catggctgca agaagattc ttggtggctc agtagcagga      60
acgaggaaag aaacttcagc accaaaaggg tttcttgcag tgtacgtcgg tgagagccag    120
aggaagaagc agagacacct tgtgccggtc tcatacttga accagccttt gtttcaagct    180
ctactcatca agctgaaga agagttcgga ttcaatcatc cgatgggcgg cttgacgatc     240
ccttgtcctg aagatacttt cctcactgta acgtctcaga tccaaggatg a            291

<210> SEQ ID NO 40
<211> LENGTH: 96
<212> TYPE: PRT
<213> ORGANISM: Arabidopsis thaliana

<400> SEQUENCE: 40

Met Ala Leu Val Arg Gly Phe Met Ala Ala Lys Lys Ile Leu Gly Gly
1               5                   10                  15

Ser Val Ala Gly Thr Arg Lys Glu Thr Ser Ala Pro Lys Gly Phe Leu
                20                  25                  30

Ala Val Tyr Val Gly Glu Ser Gln Arg Lys Lys Gln Arg His Leu Val
            35                  40                  45

Pro Val Ser Tyr Leu Asn Gln Pro Leu Phe Gln Ala Leu Leu Ile Lys
        50                  55                  60

Ala Glu Glu Glu Phe Gly Phe Asn His Pro Met Gly Gly Leu Thr Ile
65                  70                  75                  80

Pro Cys Pro Glu Asp Thr Phe Leu Thr Val Thr Ser Gln Ile Gln Gly
                85                  90                  95

<210> SEQ ID NO 41
<211> LENGTH: 505
<212> TYPE: DNA
<213> ORGANISM: Arabidopsis thaliana

<400> SEQUENCE: 41
atcatcaacc acaagcaatc cagaacttta gtccttcctt tgatcccata catattcaga     60
agcttcgaga tcaaacttc tagacaagaa aatggctttg gtgagaagta tcttcagtgc    120
aaagaagatt cttggcggct ccttagcaag aacgagcaaa gcaccaaaag gttttcttgc    180
ggtgtacgtc ggtgagaacc aagaagaa gcagagatac tttgtaccag tctcatactt     240
gaagcagcct tcatttcagg cccttctcag taaatgcgaa gaagagtttg gttttgatca    300
tccaatgggc ggcttgacaa tttgttgtcc tgaatacaca tttatcagca taacttctag    360
gatccaatga tgatcatcag taggaaaaac aataattttc ttgtaaatag attgacaaat    420
tttcatctta ttaaccaaaa gatttgttcc aaacatatga agccagtttt tgtgtaagaa    480
acaatgctat taacatataa tcagt                                           505

<210> SEQ ID NO 42
<211> LENGTH: 92
<212> TYPE: PRT
<213> ORGANISM: Arabidopsis thaliana

<400> SEQUENCE: 42

Met Ala Leu Val Arg Ser Ile Phe Ser Ala Lys Lys Ile Leu Gly Gly
1               5                   10                  15

Ser Leu Ala Arg Thr Ser Lys Ala Pro Lys Gly Phe Leu Ala Val Tyr
                20                  25                  30
```

```
Val Gly Glu Asn Gln Glu Lys Lys Gln Arg Tyr Phe Val Pro Val Ser
             35                  40                  45

Tyr Leu Lys Gln Pro Ser Phe Gln Ala Leu Leu Ser Lys Cys Glu Glu
 50                  55                  60

Glu Phe Gly Phe Asp His Pro Met Gly Gly Leu Thr Ile Cys Cys Pro
 65                  70                  75                  80

Glu Tyr Thr Phe Ile Ser Ile Thr Ser Arg Ile Gln
                 85                  90

<210> SEQ ID NO 43
<211> LENGTH: 727
<212> TYPE: DNA
<213> ORGANISM: Arabidopsis thaliana

<400> SEQUENCE: 43
ggcagacaga agcatgtgaa actctcaatt catatacgtc cccacagttt tcaaatatcc      60
cttaaaatgt tcaactctct tattgatcta tttaaaagac ccaaaacaga acaacatctc     120 cataccctatt aacaataagc aatctaagaa ctctaagctt caaaagatca agacttataa    180
acaaaaatgg ctttggtgag aagtctcttt gtttcaaaca agatacttgg aggctcatta    240
gcaggaatga aaaatcaac ttcagcacca aaagggtttc ttgcagtgta cgtaggggag     300
agccagaaga agcagagata cttagtgcta gtctcatact tgagccagcc attgtttcaa    360
gatcttctca gtaaatccga ggaagagttc ggatttgatc atccgatggg gggcttgacg    420
atcccttgtc ctgaagatac cttcctcact gtaacttctc ggatccaagg atgatcatca    480
tctgaagaaa aacttaacac ttttctttct tcttttttt gacagcaaca ctttaattac    540
tgtagataga tgagaatttt tttcattttt cttgaattat ttgatcaaga agatagaaat   600
tccaatgtaa atgccagttt tgtcatttgt cattttattt atggaatcaa acaaaagatc    660
cagacagatt tctaagttct gtttatatga tgtgtttatc aacagttata tactataaag   720
tataaaa                                                                727

<210> SEQ ID NO 44
<211> LENGTH: 95
<212> TYPE: PRT
<213> ORGANISM: Arabidopsis thaliana

<400> SEQUENCE: 44

Met Ala Leu Val Arg Ser Leu Phe Val Ser Asn Lys Ile Leu Gly Gly
  1               5                  10                  15

Ser Leu Ala Gly Met Arg Lys Ser Thr Ser Ala Pro Lys Gly Phe Leu
             20                  25                  30

Ala Val Tyr Val Gly Glu Ser Gln Lys Lys Gln Arg Tyr Leu Val Leu
             35                  40                  45

Val Ser Tyr Leu Ser Gln Pro Leu Phe Gln Asp Leu Leu Ser Lys Ser
 50                  55                  60

Glu Glu Glu Phe Gly Phe Asp His Pro Met Gly Gly Leu Thr Ile Pro
 65                  70                  75                  80

Cys Pro Glu Asp Thr Phe Leu Thr Val Thr Ser Arg Ile Gln Gly
                 85                  90                  95

<210> SEQ ID NO 45
<211> LENGTH: 396
<212> TYPE: DNA
<213> ORGANISM: Arabidopsis thaliana

<400> SEQUENCE: 45
```

```
atgacagagc agaacgatac agctggacaa aaccatgtca aactctctgc ccctacgctt    60
ttagaccaca aaacaaaaca ccattgtcat atcatcaata accagcaatc aaataactca   120
tatatgcttc aaaccaagac tttcaagatt caaatggctt tggttagagg tatttatgct   180
tcaaagaaga cacttgaccg ctctatagca gctgcagcag caacattgag caaaagacat   240
gtgggttctg cgctagcctt tgtcctagct tcttacttga accagccttt gtttcaagct   300
cttctcagta aatccgaaga ggagttaggg tttgattatc cgatggttgg cctgacgatt   360
cgttgcccag agataacttt tctcactata ctgtaa                              396

<210> SEQ ID NO 46
<211> LENGTH: 131
<212> TYPE: PRT
<213> ORGANISM: Arabidopsis thaliana

<400> SEQUENCE: 46

Met Thr Glu Gln Asn Asp Thr Ala Gly Gln Asn His Val Lys Leu Ser
1               5                   10                  15

Ala Pro Thr Leu Leu Asp His Lys Thr Lys His His Cys His Ile Ile
            20                  25                  30

Asn Asn Gln Gln Ser Asn Asn Ser Tyr Met Leu Gln Thr Lys Thr Phe
        35                  40                  45

Lys Ile Gln Met Ala Leu Val Arg Gly Ile Tyr Ala Ser Lys Lys Thr
    50                  55                  60

Leu Asp Arg Ser Ile Ala Ala Ala Ala Thr Leu Ser Lys Arg His
65                  70                  75                  80

Val Gly Ser Ala Leu Ala Phe Val Leu Ala Ser Tyr Leu Asn Gln Pro
                85                  90                  95

Leu Phe Gln Ala Leu Leu Ser Lys Ser Glu Glu Leu Gly Phe Asp
            100                 105                 110

Tyr Pro Met Val Gly Leu Thr Ile Arg Cys Pro Gly Asp Asn Phe Leu
        115                 120                 125

Thr Ile Leu
    130

<210> SEQ ID NO 47
<211> LENGTH: 472
<212> TYPE: DNA
<213> ORGANISM: Arabidopsis thaliana

<400> SEQUENCE: 47
atggctttgg tgagaagtct ctttagcgca aagaagattc ttggcggttc tttagtaaaa    60
acaagcaagg caccgccaaa agggtttctt gcagtgtacg tcggcgagag ccagaagaag   120
cagagacatt tgtaccagt ctcatacttg aaccagcctt tgtttcaaga tcttctaagc   180
aaatgtgaag aagagtttgg ttttgatcat ccgatgggcg gcttgacaat cccttgtcct   240
gtagatactt ttatcagtat aacatctcag ctccaaggat gaagatgatg atgatccaac   300
aaaaatacat taacaatttt ttttttttac tcaaactaga gatggaggag tattccatgt   360
gaatagataa catttttttc tcctctttcc tatttgatag agtttgttct agacgattag   420
aaaatttcga atgtgattgc cgttttgta taacaaagat caaatcattt ac             472

<210> SEQ ID NO 48
<211> LENGTH: 93
<212> TYPE: PRT
<213> ORGANISM: Arabidopsis thaliana
```

-continued

```
<400> SEQUENCE: 48

Met Ala Leu Val Arg Ser Leu Phe Ser Ala Lys Lys Ile Leu Gly Gly
1               5                   10                  15

Ser Leu Val Lys Thr Ser Lys Ala Pro Pro Lys Gly Phe Leu Ala Val
            20                  25                  30

Tyr Val Gly Glu Ser Gln Lys Lys Gln Arg His Phe Val Pro Val Ser
        35                  40                  45

Tyr Leu Asn Gln Pro Leu Phe Gln Asp Leu Leu Ser Lys Cys Glu Glu
    50                  55                  60

Glu Phe Gly Phe Asp His Pro Met Gly Gly Leu Thr Ile Pro Cys Pro
65                  70                  75                  80

Val Asp Thr Phe Ile Ser Ile Thr Ser Gln Leu Gln Gly
                85                  90

<210> SEQ ID NO 49
<211> LENGTH: 4091
<212> TYPE: DNA
<213> ORGANISM: Arabidopsis thaliana

<400> SEQUENCE: 49
cgtatcgaaa atcttcttcg ggtcagacga tctgaagccg atcgctgtag aatcagtttc     60
gtgctccgca gtttctcgag tttcctctca cttcagatct tcataagaga attcacttac    120
ggagagggac tttttcgtag acgattctca ctggatatct atcacccggt aagatcgtct    180
tgctcgaaaa gaattgaaaa gttttttaagt aattgaataa ggaactgtga atcggagagg    240 cttactttt  tgaaaagatc taaaccatcg tagaagatcg tcctcaaata tctcacagaa    300
gttaccaatt tgaaagatc actagagata gctacggatt tgagaggcg atctgtcca    360 ggtcggcact gtgaaagaga actacactgg ttttttccag atgatatgaa gcttccgtga    420
acgaatctga ttctaaggta ctcatcgaag agaatctggg attgtattga tctggtccct    480
tagcttccag tttggctata actctgacaa ctgttgtaag tgataagttg tgatcaataa    540
tgggtacgga gaatcagggc tatccaaatt ttccagctag gcctgcttcc tctccatttg    600
catctgctcc gccaccaggg attcctcctc aatcaggtgg accacccact ggatcagagg    660
cggttggctt tagaccttt acaccatctg catcccaacc tacaagacct ttcactgcct    720
ctggtcctcc tccggctcca ccagtgggta cgatgaggcc tggccagccg tctccttttg    780
tttctcagat tcctgggagt agacctccac cgccatcatc aaattcgttt ccttcaccag    840
catatggtcc tcctggtggt gccccttttc agcgttttcc atcccgcca ttcccgacta    900 cacaaaaccc tcctcagggc ccaccaccac ctcaaactct gcaggtcac ttatctcctc    960 ctatgtctct tcgcccacag caaccgatgg cacctgtagc aatgggcct ccgccacaaa    1020 gtacgacttc tgggctacct ggagcaaatg cttatccccc tgctacagat tatcatatgc    1080
ctgccaggcc tggttttcaa cagtcaatgc ctccagttac tccgtcttat cctggcgtgg    1140
gcggttcgca gccatctttt cctggttatc ctagcaagca ggtcttacag gctccgacgc    1200
cattccagac atctcaaggt cccccaggac cccctccagt ctcatcatat cctcctcaca    1260
caggaggttt tgctcagcga ccaaatatgg cagcacagca gaatctgcat ccaaactatg    1320
cacctcctcc cagtaacgtt caaggcttga ctgaagattt taactcgcta tctctttcat    1380
ctattcctgg atcgctggaa ccaggacttg atcataaatc attcccaagg ccattggatg    1440
gtgacgtgga gccaaattca tttgctgaaa tgtaccaat gaattgccat tctagatatc    1500
tacgactgac gactagtgct ataccaaatt cccagtctct ggcttcaagg tggcatttac    1560
```

```
ctctaggagc tgtggtttgt ccacttgctg agactcctga aggggaggag gtaccactta    1620
ttgattttgg ctcaactggc atcatccgct gcagaagatg ccgtacctat gtgaatcctt    1680
ttgtgacttt tacagattct ggaagaaagt ggcggtgtaa tatatgttcg atgcttaatg    1740
atgtgcctgg tgaatacttc tcacatttgg atgctactgg ccgaagaatg gatatggatc    1800
aacgacctga gctgactaaa ggcagtgttg aaatcatagc tccaactgaa tacatggttc    1860
ggcctccgat gccacctatc tacttcttcc tcattgatgt ttcgatttcg gctactaaaa    1920
gtggaatgct tgaggttgtt gctcaaacga ttaagtcttg tttggataac ctgcctggtt    1980
atccaagaac tcaaattgga tttattactt atgacagcac gttacatttt tacaacatga    2040
agtcatcttt gagccagccg cagatgatgg ttgtatcaga tctagatgat atctttgtcc    2100
cattgccaga cgatctgctt gtaaatctat ctgaatctag aactgtggtg gacgcctttt    2160
tggacagtct accttttgatg tttcaagata atttcaatgt ggaatcagct tttggcccag    2220
ccctcagagc ggcgtttatg gttatgaacc aacttggggg caagttacta attttccaga    2280
actcattacc ttctcttggt gctgggaggt aaagttgcg gggagatgat cctcgtgtct    2340
atggaactga caaagaatat gcattaaggg tagctgaaga tcccttctat aaacaaatgg    2400
ctgctgattg taccaagttc cagataggaa ttaatgttta tgcattcagt gataagtaca    2460
ctgatattgc ctcattaggg actctggcaa aatacactgg aggacaggtg tactattatc    2520
caggtttcca atcatctgtt catggagata agttaagaca cgagcttgct agagaccta    2580
caagggaaac tgcgtgggag gcggttatgc gaataagatg tggaaaagga attcgtttct    2640
cgtcctacca tgggaacttc atgctaaggt ctactgacct gcttgctctt cctgctgttg    2700
actgtgacaa agcgtatgca atgcagctat ctcttgagga actttgcta acatcccaga    2760
ctgtgtattt ccaagtggct ttgctatata ccgcctcttg tggagagaga cgtataaggg    2820
tacacacatc tgttgcacca gtggttacag atcttgggga gatgtataga caagcagaca    2880
ctggttccat tgtgtcttta tatgctagat tagcaattga gaaatctttg tccgcaaaat    2940
tggatgatgc acggaatgca atacagcaaa agattgttaa agccctcaaa gaatatcgta    3000
atcttcacgc ggtgcagcat cgcttggggt ccagattagt atacccagag tctctgaagt    3060
tcttgccatt gtacggattg gcaattacta agtccactcc tcttctaggt ggacctgctg    3120
atacttctct tgatgagcgc tgtgctgcag gcttcaccat gatggctctg cctgtcaaaa    3180
agctattgaa gcttttgtat cccaatttat tccgtgttga cgaatggctc ttaaagccat    3240
cagcagccca cgatgacttt aaagacgtat taaggagatt gccgctggct gcagagagtt    3300
tggattctag aggcctttac atatatgatg atggttttcg attagttttg tggtttggcc    3360
ggatgctttc acctgacatt gctaaaaatc ttccttgggt tgactttgca gcagacctct    3420
caagggttac ctttcaagag caagagaatg ggatgtcaaa gaagctaatg aggttggtaa    3480
agaaactgag ggagagtgat ccttcatatc accccatgtg ttttctagtg agacaaggag    3540
aacaaccccg agaaggcttc cttctcctca gaaatctcat tgaggaccag atgggcggtt    3600
cgagtggtta tgtcgattgg attctacaac ttcaccgcca agttcaacaa actaagata    3660
gctcacaatg acaactcggg tgctaggatg ccacctcttt gtaaccattg aagaactctt    3720
gagctcaaaa atcttctact taagcaggat catggcggcc ttcttccttg gccataatg    3780
tgttgttttg gataaagaag tgctactttt tgatttttct tcatttgttt ttctatatag    3840
accttttttc tcaagattag cttttattt gcctaaccag aatggttatc tccgtaagat    3900
tagtcgtttt ttaaatcttt tgttgccttt tttttttgtc ctcattcgat tttttgttga    3960
```

```
tgtgcgtctg ttctagattt attttgggag ttgcagttca tgaatctgtc ctaattaggg    4020
ttattaacaa gaagatgcta ctgttaaaat tttaaaatat ttttatgaat aaataatgtt    4080
gtgaaaacct t                                                         4091
```

<210> SEQ ID NO 50
<211> LENGTH: 1038
<212> TYPE: PRT
<213> ORGANISM: Arabidopsis thaliana

<400> SEQUENCE: 50

```
Met Gly Thr Glu Asn Gln Gly Tyr Pro Asn Phe Pro Ala Arg Pro Ala
1               5                   10                  15

Ser Ser Pro Phe Ala Ser Ala Pro Pro Gly Ile Pro Pro Gln Ser
            20                  25                  30

Gly Gly Pro Pro Thr Gly Ser Glu Ala Val Gly Phe Arg Pro Phe Thr
        35                  40                  45

Pro Ser Ala Ser Gln Pro Thr Arg Pro Phe Thr Ala Ser Gly Pro Pro
    50                  55                  60

Pro Ala Pro Pro Val Gly Thr Met Arg Pro Gly Gln Pro Ser Pro Phe
65                  70                  75                  80

Val Ser Gln Ile Pro Gly Ser Arg Pro Pro Pro Ser Ser Asn Ser
                85                  90                  95

Phe Pro Ser Pro Ala Tyr Gly Pro Gly Gly Ala Pro Phe Gln Arg
            100                 105                 110

Phe Pro Ser Pro Pro Phe Pro Thr Thr Gln Asn Pro Pro Gln Gly Pro
        115                 120                 125

Pro Pro Gln Thr Leu Ala Gly His Leu Ser Pro Pro Met Ser Leu
    130                 135                 140

Arg Pro Gln Gln Pro Met Ala Pro Val Ala Met Gly Pro Pro Pro Gln
145                 150                 155                 160

Ser Thr Thr Ser Gly Leu Pro Gly Ala Asn Ala Tyr Pro Pro Ala Thr
                165                 170                 175

Asp Tyr His Met Pro Ala Arg Pro Gly Phe Gln Gln Ser Met Pro Pro
            180                 185                 190

Val Thr Pro Ser Tyr Pro Gly Val Gly Gly Ser Gln Pro Ser Phe Pro
        195                 200                 205

Gly Tyr Pro Ser Lys Gln Val Leu Gln Ala Pro Thr Pro Phe Gln Thr
    210                 215                 220

Ser Gln Gly Pro Pro Gly Pro Pro Val Ser Ser Tyr Pro Pro His
225                 230                 235                 240

Thr Gly Gly Phe Ala Gln Arg Pro Asn Met Ala Ala Gln Gln Asn Leu
                245                 250                 255

His Pro Asn Tyr Ala Pro Pro Ser Asn Val Gln Gly Leu Thr Glu
            260                 265                 270

Asp Phe Asn Ser Leu Ser Leu Ser Ser Ile Pro Gly Ser Leu Glu Pro
        275                 280                 285

Gly Leu Asp His Lys Ser Phe Pro Arg Pro Leu Asp Gly Asp Val Glu
    290                 295                 300

Pro Asn Ser Phe Ala Glu Met Tyr Pro Met Asn Cys His Ser Arg Tyr
305                 310                 315                 320

Leu Arg Leu Thr Thr Ser Ala Ile Pro Asn Ser Gln Ser Leu Ala Ser
                325                 330                 335

Arg Trp His Leu Pro Leu Gly Ala Val Val Cys Pro Leu Ala Glu Thr
            340                 345                 350
```

-continued

```
Pro Glu Gly Glu Glu Val Pro Leu Ile Asp Phe Gly Ser Thr Gly Ile
        355                 360                 365

Ile Arg Cys Arg Arg Cys Arg Thr Tyr Val Asn Pro Phe Val Thr Phe
    370                 375                 380

Thr Asp Ser Gly Arg Lys Trp Arg Cys Asn Ile Cys Ser Met Leu Asn
385                 390                 395                 400

Asp Val Pro Gly Glu Tyr Phe Ser His Leu Asp Ala Thr Gly Arg Arg
                405                 410                 415

Met Asp Met Asp Gln Arg Pro Glu Leu Thr Lys Gly Ser Val Glu Ile
            420                 425                 430

Ile Ala Pro Thr Glu Tyr Met Val Arg Pro Met Pro Pro Ile Tyr
        435                 440                 445

Phe Phe Leu Ile Asp Val Ser Ile Ser Ala Thr Lys Ser Gly Met Leu
    450                 455                 460

Glu Val Val Ala Gln Thr Ile Lys Ser Cys Leu Asp Asn Leu Pro Gly
465                 470                 475                 480

Tyr Pro Arg Thr Gln Ile Gly Phe Ile Thr Tyr Asp Ser Thr Leu His
                485                 490                 495

Phe Tyr Asn Met Lys Ser Ser Leu Ser Gln Pro Gln Met Met Val Val
            500                 505                 510

Ser Asp Leu Asp Asp Ile Phe Val Pro Leu Pro Asp Asp Leu Leu Val
        515                 520                 525

Asn Leu Ser Glu Ser Arg Thr Val Val Asp Ala Phe Leu Asp Ser Leu
    530                 535                 540

Pro Leu Met Phe Gln Asp Asn Phe Asn Val Ser Ala Phe Gly Pro
545                 550                 555                 560

Ala Leu Arg Ala Ala Phe Met Val Met Asn Gln Leu Gly Gly Lys Leu
                565                 570                 575

Leu Ile Phe Gln Asn Ser Leu Pro Ser Leu Gly Ala Gly Arg Leu Lys
            580                 585                 590

Leu Arg Gly Asp Asp Pro Arg Val Tyr Gly Thr Asp Lys Glu Tyr Ala
        595                 600                 605

Leu Arg Val Ala Glu Asp Pro Phe Tyr Lys Gln Met Ala Ala Asp Cys
    610                 615                 620

Thr Lys Phe Gln Ile Gly Ile Asn Val Tyr Ala Phe Ser Asp Lys Tyr
625                 630                 635                 640

Thr Asp Ile Ala Ser Leu Gly Thr Leu Ala Lys Tyr Thr Gly Gly Gln
                645                 650                 655

Val Tyr Tyr Tyr Pro Gly Phe Gln Ser Ser Val His Gly Asp Lys Leu
            660                 665                 670

Arg His Glu Leu Ala Arg Asp Leu Thr Arg Glu Thr Ala Trp Glu Ala
        675                 680                 685

Val Met Arg Ile Arg Cys Gly Lys Gly Ile Arg Phe Ser Ser Tyr His
    690                 695                 700

Gly Asn Phe Met Leu Arg Ser Thr Asp Leu Leu Ala Leu Pro Ala Val
705                 710                 715                 720

Asp Cys Asp Lys Ala Tyr Ala Met Gln Leu Ser Leu Glu Glu Thr Leu
                725                 730                 735

Leu Thr Ser Gln Thr Val Tyr Phe Gln Val Ala Leu Leu Tyr Thr Ala
            740                 745                 750

Ser Cys Gly Glu Arg Arg Ile Arg Val His Thr Ser Val Ala Pro Val
        755                 760                 765

Val Thr Asp Leu Gly Glu Met Tyr Arg Gln Ala Asp Thr Gly Ser Ile
    770                 775                 780
```

Val Ser Leu Tyr Ala Arg Leu Ala Ile Glu Lys Ser Leu Ser Ala Lys
785                 790                 795                 800

Leu Asp Asp Ala Arg Asn Ala Ile Gln Gln Lys Ile Val Lys Ala Leu
        805                 810                 815

Lys Glu Tyr Arg Asn Leu His Ala Val Gln His Arg Leu Gly Ser Arg
    820                 825                 830

Leu Val Tyr Pro Glu Ser Leu Lys Phe Leu Pro Leu Tyr Gly Leu Ala
        835                 840                 845

Ile Thr Lys Ser Thr Pro Leu Leu Gly Gly Pro Ala Asp Thr Ser Leu
    850                 855                 860

Asp Glu Arg Cys Ala Ala Gly Phe Thr Met Met Ala Leu Pro Val Lys
865                 870                 875                 880

Lys Leu Leu Lys Leu Leu Tyr Pro Asn Leu Phe Arg Val Asp Glu Trp
            885                 890                 895

Leu Leu Lys Pro Ser Ala Ala His Asp Asp Phe Lys Asp Val Leu Arg
        900                 905                 910

Arg Leu Pro Leu Ala Ala Glu Ser Leu Asp Ser Arg Gly Leu Tyr Ile
    915                 920                 925

Tyr Asp Asp Gly Phe Arg Leu Val Leu Trp Phe Gly Arg Met Leu Ser
930                 935                 940

Pro Asp Ile Ala Lys Asn Leu Leu Gly Val Asp Phe Ala Ala Asp Leu
945                 950                 955                 960

Ser Arg Val Thr Phe Gln Glu Gln Glu Asn Gly Met Ser Lys Lys Leu
            965                 970                 975

Met Arg Leu Val Lys Lys Leu Arg Glu Ser Asp Pro Ser Tyr His Pro
        980                 985                 990

Met Cys Phe Leu Val Arg Gln Gly Glu Gln Pro Arg Glu Gly Phe Leu
    995                 1000                1005

Leu Leu Arg Asn Leu Ile Glu Asp Gln Met Gly Gly Ser Ser Gly
    1010                1015                1020

Tyr Val Asp Trp Ile Leu Gln Leu His Arg Gln Val Gln Gln Asn
    1025                1030                1035

<210> SEQ ID NO 51
<211> LENGTH: 893
<212> TYPE: DNA
<213> ORGANISM: Arabidopsis thaliana

<400> SEQUENCE: 51
taatttgaat aagctgctca cttttaatca ccccggagta gtaagcttgc ggctgatcag      60
agctgagtga aaatggtgt ctggatcagg aatttgcgcg aagcgcgtgg tggttgatgc      120
tcgtcaccac atgctaggtc gcttggcttc ggttgtagca aaggatctgc tcaatggcca     180
gaatattgtg gttgtccggt gcgaggagat ttgtctctcc ggcggacttg ttcgtcagaa     240
gatgaagtac atgaggtttc tccgtaagcg tatgaacact aaaccttctc acggacctat     300
tcacttccgt gctccctcca agatcttctg gcgtaccgtt cgcggtatga ttccacacaa     360
gactaagcgt ggagctaatg cacttgcccg cttgaaggtc tttgaaggag ttcctactcc     420
atatgacaag atcaagagga tggtcgttcc tgatgctctc aaggtcttga ggctgcaggc     480
tggacacaaa tactgtctgt gggtcgcct tcttctgaa gtcgggtgga accactacga      540
caccatcaag caggagctgg agaacaagag aaaggaaaga gctcaagctg tttatgagag     600
aaagaagcaa cttagcaaac tcagagctaa ggccgagaag gttgctgaag agaagcttgg     660
atctcaattg gatgttcttg cacccgtcaa gtactgaatt caatcagttt atcgtatttg     720

```
aatgttttg caagttttgc tcagacatta tactattata ttacgaggtt ttgttgtatg      780
cgattttgac ttagtttatt tcttgaattc gactttactt agtttatttc ttgaattcgt      840
cttttgtcat gcgcctcctc caaaacgttt cgtgatttat ttttcctctg cat             893
```

<210> SEQ ID NO 52
<211> LENGTH: 207
<212> TYPE: PRT
<213> ORGANISM: Arabidopsis thaliana

<400> SEQUENCE: 52

```
Met Val Ser Gly Ser Gly Ile Cys Ala Lys Arg Val Val Asp Ala
1               5                   10                  15

Arg His His Met Leu Gly Arg Leu Ala Ser Val Val Ala Lys Asp Leu
                20                  25                  30

Leu Asn Gly Gln Asn Ile Val Val Arg Cys Glu Glu Ile Cys Leu
            35                  40                  45

Ser Gly Gly Leu Val Arg Gln Lys Met Lys Tyr Met Arg Phe Leu Arg
        50                  55                  60

Lys Arg Met Asn Thr Lys Pro Ser His Gly Pro Ile His Phe Arg Ala
65                  70                  75                  80

Pro Ser Lys Ile Phe Trp Arg Thr Val Arg Gly Met Ile Pro His Lys
                85                  90                  95

Thr Lys Arg Gly Ala Asn Ala Leu Ala Arg Leu Lys Val Phe Glu Gly
                100                 105                 110

Val Pro Thr Pro Tyr Asp Lys Ile Lys Arg Met Val Val Pro Asp Ala
            115                 120                 125

Leu Lys Val Leu Arg Leu Gln Ala Gly His Lys Tyr Cys Leu Leu Gly
        130                 135                 140

Arg Leu Ser Ser Glu Val Gly Trp Asn His Tyr Asp Thr Ile Lys Gln
145                 150                 155                 160

Glu Leu Glu Asn Lys Arg Lys Glu Arg Ala Gln Ala Val Tyr Glu Arg
                165                 170                 175

Lys Lys Gln Leu Ser Lys Leu Arg Ala Lys Ala Glu Lys Val Ala Glu
            180                 185                 190

Glu Lys Leu Gly Ser Gln Leu Asp Val Leu Ala Pro Val Lys Tyr
        195                 200                 205
```

<210> SEQ ID NO 53
<211> LENGTH: 881
<212> TYPE: DNA
<213> ORGANISM: Arabidopsis thaliana

<400> SEQUENCE: 53

```
taagctgctc acttttaatc accccggagt agtaagcttg cggctgatca gagctgagtg      60
aaaaatggtg tctggatcag gaatttgcgc gaagcgcgtg gtggttgatg ctcgtcacca     120
catgctaggt cgcttggctt cggttgtagc aaaggatctg ctcaatggcc agaatattgt     180
ggttgtccgg tgcgaggaga tttgtctctc cggcggactt gttcgtcaga agatgaagta     240
catgaggttt ctccgtaagc gtatgaacac taaaccttct cacggaccta ttcacttccg     300
tgctccctcc aagatcttct ggcgtaccgt tcgcggtatg attccacaca agactaagcg     360
tggagctaat gcacttgccc gcttgaaggt cttTgaagga gttcctactc catatgacaa     420
gatcaagagg atggtcgttc ctgatgctct caaggtcttg aggctgcagg ctggacacaa     480
atactgtctg ttgggtcgcc tttcttctga agtcgggtgg aaccactacg acaccatcaa     540
```

```
ggagctggag aacaagagaa aggaaagagc tcaagctgtt tatgagagaa agaagcaact    600
tagcaaactc agagctaagg ccgagaaggt tgctgaagag aagcttggat ctcaattgga    660
tgttcttgca cccgtcaagt actgaattca atcagtttat cgtatttgaa tgttttttgca   720 agttttgctc agacattata ctattatatt acgaggtttt gttgtatgcg attttgactt   780
agtttatttc ttgaattcga ctttacttag tttatttctt gaattcgtct tttgtcatgc   840
gcctcctcca aaacgtttcg tgatttattt ttcctctgca t                        881

<210> SEQ ID NO 54
<211> LENGTH: 206
<212> TYPE: PRT
<213> ORGANISM: Arabidopsis thaliana

<400> SEQUENCE: 54

Met Val Ser Gly Ser Gly Ile Cys Ala Lys Arg Val Val Asp Ala
1               5                   10                  15

Arg His His Met Leu Gly Arg Leu Ala Ser Val Val Ala Lys Asp Leu
                20                  25                  30

Leu Asn Gly Gln Asn Ile Val Val Arg Cys Glu Glu Ile Cys Leu
            35                  40                  45

Ser Gly Gly Leu Val Arg Gln Lys Met Lys Tyr Met Arg Phe Leu Arg
50                  55                  60

Lys Arg Met Asn Thr Lys Pro Ser His Gly Pro Ile His Phe Arg Ala
65                  70                  75                  80

Pro Ser Lys Ile Phe Trp Arg Thr Val Arg Gly Met Ile Pro His Lys
                85                  90                  95

Thr Lys Arg Gly Ala Asn Ala Leu Ala Arg Leu Lys Val Phe Glu Gly
            100                 105                 110

Val Pro Thr Pro Tyr Asp Lys Ile Lys Arg Met Val Val Pro Asp Ala
        115                 120                 125

Leu Lys Val Leu Arg Leu Gln Ala Gly His Lys Tyr Cys Leu Leu Gly
    130                 135                 140

Arg Leu Ser Ser Glu Val Gly Trp Asn His Tyr Asp Thr Ile Lys Glu
145                 150                 155                 160

Leu Glu Asn Lys Arg Lys Glu Arg Ala Gln Ala Val Tyr Glu Arg Lys
                165                 170                 175

Lys Gln Leu Ser Lys Leu Arg Ala Lys Ala Glu Lys Val Ala Glu Glu
            180                 185                 190

Lys Leu Gly Ser Gln Leu Asp Val Leu Ala Pro Val Lys Tyr
        195                 200                 205

<210> SEQ ID NO 55
<211> LENGTH: 1164
<212> TYPE: DNA
<213> ORGANISM: Arabidopsis thaliana

<400> SEQUENCE: 55
gaattctttc attaagcaaa tccaatgttt tcgactctct aaattcaatg cacgaggtaa    60
catttcgatg catggagtta aatgtcagcg ttaaagagcc gtagtaactc gttagccgga   120
ctaagtctag acgctgtgct tggcggcgag atccttatag aaccgccatc tctaccgtcg   180
ccaccacctt taccatcaaa atctcttgta ccgcaccgtc caacaagcca aacccttttt   240
gatatcatac gtgaggaata cgccaaagaa gggcacaaag atcggaccac gtggcagatt   300
ttccgtgaga aactccgtct taacgaacc  ggttctgctt ggacctcgtc tcttcatatc   360
cctgcttcgg atatccttat ccctaatccc aaacacattg aacagcgtt ccggtctcac    420
```

```
tccgccggtt taaacatccg agatctggtt cacgctatac cgatgtcaga tccacctggt    480
tcttcaggac gcgctatgtt cacgcgcgga tcttcaatgc gggtcgggtc gagtaaaaac    540
ccggacgatt cgcctgacat cagcgttctt gaagatgggc caccgtctag gagttttaag    600
ccgcagttat cacggcacga ttccgttaga gatcacagcg aaggcgaaga aaacaacaga    660
cgacgtcatc cgatcgtcac gttcgtggaa gagagacaaa tgtcggcgag agaagcggtt    720
gctgctcaag aagcggcgga agctgaagcg gcggcggctg gaggaagcga agatgaagac    780
gacgatgacg aagaggatga ttcaggagaa acagaggaga tgaaatcatc ttcagcttct    840
gagccgaaac agacgatgtc tctgatggat ctgttggaag aaacagatcg acaaatggga    900
ttaacaggat cgagatacgc catggatgaa gatgaagagt acgaagaaga cgaagaagat    960
gagaacaacg aggaagaagg agatagtcat ggaggaggag aaggagagct tagttgctgc   1020
gtttgcatgg tgaaaataaa aggcgcttct tttacacctt gtggtcacac gttttgtaag   1080
ctctgttcta aagagcttat ggctcagaaa ggtcactgtc ctgtttgcag cagcttcgtt   1140
ctcgagttcc ttgagatctt ttag                                          1164
```

<210> SEQ ID NO 56
<211> LENGTH: 360
<212> TYPE: PRT
<213> ORGANISM: Arabidopsis thaliana

<400> SEQUENCE: 56

```
Met Ser Ala Leu Lys Ser Arg Ser Asn Ser Leu Ala Gly Leu Ser Leu
1               5                   10                  15

Asp Ala Val Leu Gly Gly Glu Ile Leu Ile Glu Pro Pro Ser Leu Pro
            20                  25                  30

Ser Pro Pro Leu Pro Ser Lys Ser Leu Val Pro His Arg Pro Thr
        35                  40                  45

Ser Gln Thr Leu Phe Asp Ile Ile Arg Glu Glu Tyr Ala Lys Glu Gly
    50                  55                  60

His Lys Asp Arg Thr Thr Trp Gln Ile Phe Arg Glu Lys Leu Arg Leu
65                  70                  75                  80

Lys Arg Thr Gly Ser Ala Trp Thr Ser Ser Leu His Ile Pro Ala Ser
                85                  90                  95

Asp Ile Leu Ile Pro Asn Pro Lys His Ile Gly Thr Ala Phe Arg Ser
            100                 105                 110

His Ser Ala Gly Leu Asn Ile Arg Asp Leu Val His Ala Ile Pro Met
        115                 120                 125

Ser Asp Pro Pro Gly Ser Ser Gly Arg Ala Met Phe Thr Arg Gly Ser
    130                 135                 140

Ser Met Arg Val Gly Ser Ser Lys Asn Pro Asp Asp Ser Pro Asp Ile
145                 150                 155                 160

Ser Val Leu Glu Asp Gly Pro Pro Ser Arg Ser Phe Lys Pro Gln Leu
                165                 170                 175

Ser Arg His Asp Ser Val Arg Asp His Ser Glu Gly Glu Asn Asn
            180                 185                 190

Arg Arg Arg His Pro Ile Val Thr Phe Val Glu Glu Arg Gln Met Ser
        195                 200                 205

Ala Arg Glu Ala Val Ala Ala Gln Glu Ala Ala Glu Ala Ala
    210                 215                 220

Ala Ala Gly Gly Ser Glu Asp Glu Asp Asp Asp Glu Glu Asp Asp
225                 230                 235                 240
```

```
Ser Gly Glu Thr Glu Met Lys Ser Ser Ala Ser Glu Pro Lys
            245                 250                 255

Gln Thr Met Ser Leu Met Asp Leu Leu Glu Glu Thr Asp Arg Gln Met
            260                 265                 270

Gly Leu Thr Gly Ser Arg Tyr Ala Met Asp Glu Asp Glu Tyr Glu
            275                 280                 285

Glu Asp Glu Glu Asp Glu Asn Asn Glu Glu Glu Gly Asp Ser His Gly
            290                 295                 300

Gly Gly Glu Gly Glu Leu Ser Cys Cys Val Cys Met Val Lys Ile Lys
305                 310                 315                 320

Gly Ala Ser Phe Thr Pro Cys Gly His Thr Phe Cys Lys Leu Cys Ser
            325                 330                 335

Lys Glu Leu Met Ala Gln Lys Gly His Cys Pro Val Cys Ser Ser Phe
            340                 345                 350

Val Leu Glu Phe Leu Glu Ile Phe
            355                 360

<210> SEQ ID NO 57
<211> LENGTH: 1676
<212> TYPE: DNA
<213> ORGANISM: Arabidopsis thaliana

<400> SEQUENCE: 57
ccaccaccac caccctctgg aacgatgacg tttctactac ttctactctt ctgctttctc        60
tcgccggcaa tctcctccgc ccactctatt ccgtcaactt tagatggacc gttcgttccg       120
gtgacggtgc cattggacac ctctctccgg gggcaagcca tcgatttgcc cgacaccgat       180
ccccgcgtcc gccggcgtgt cattggtttt gagccgagca aaatctctct ctccctctcc       240
tccgatcatg attccatctg gtctcttgg atcacaggtg agttccaaat cggaagaag        300 gtgaagccat tagatccgac aagtatcaac agtgttgttc aattcggaac cttgaggcac       360
tcactgagtc atgaagctaa aggacattca cttgtttata gtcaacttta tccttttcgac       420 ggtctcctta actacacttc tggaatcata ccaccatgttc gcattacagg ctgaaaacca       480
agtactatct attactatcg atgtggagat ccttcaagac gggctatgag taagatacac       540
catttcagga caatgcctgt ttctagtccc tcgagttatc ctggtcgaat agcggttgtt       600
ggtgatcttg gtctcactta taacactact gatacaatta gtcacttgat tcataactct       660
ccggatctca tttttattgat cggcgacgtg agttatgcaa acttgtatct aacaaacggg       720
actagctctg attgttattc ttgctctttc cctgagacac ctatacatga gacgtatcag       780
ccacgttggg actactgggg taggtttatg gagaatctga cttccaaagt tcctttgatg       840
gtgattgaag gaaccatga gatcgaattg caagcagaga caagacatt tgaagcttat        900 agttcaagat tcgctttccc ttttaatgaa agcggctcgt cttctacgct atattattcc       960
tttaacgctg gtgggattca ctttgttatg cttggtgcct acattgcgta tgacaaatca      1020
gcggaacaat atgaatggtt aaagaaggat ttggctaaag tcgatagatc ggtaactcca      1080
tggttagtag cttcttggca tccaccttgg tatagttctt atacagcgca ttacagagaa      1140
gcagaatgta tgaaagaagc tatggaggaa ttactttatt cttatggtac cgacattgtc      1200
tttaacggac atgtgcatgc ttatgaacgg tcgaacagag tatacaatta cgaactggac      1260
ccatgtggtc cagtttacat tgtgattggt gatggaggta accgtgaaaa gatggcgatc      1320
gagcatgcag atgaccccgg taatgtcca gagccgttaa ccacgcccga tccagtcatg       1380
ggtgggtttt gcgcgtggaa cttcacgccg tctgataagt tctgttggga tcggcaacct      1440
```

-continued

```
gattatagtg ccctgagaga aagcagcttt ggccatggaa tcctagagat gaagaacgag    1500
acatgggcac tatggacatg gtataggaat caagactcga gcagtgaagt cggagatcag    1560
atttatattg tgagacaacc tgatcgatgt ccgcttcacc accgccttgt taaccattgc    1620
taagatcaaa cagagatggt ctaataaaat ttttgggact tgatcatgt aacagt          1676
```

<210> SEQ ID NO 58
<211> LENGTH: 532
<212> TYPE: PRT
<213> ORGANISM: Arabidopsis thaliana

<400> SEQUENCE: 58

| | | | | | | | | | | | | | | | |
|---|---|---|---|---|---|---|---|---|---|---|---|---|---|---|---|
| Met | Thr | Phe | Leu | Leu | Leu | Leu | Phe | Cys | Phe | Leu | Ser | Pro | Ala | Ile | |
| 1 | | | | 5 | | | | | 10 | | | | | 15 | |
| Ser | Ser | Ala | His | Ser | Ile | Pro | Ser | Thr | Leu | Asp | Gly | Pro | Phe | Val | Pro |
| | | | 20 | | | | | 25 | | | | | 30 | | |
| Val | Thr | Val | Pro | Leu | Asp | Thr | Ser | Leu | Arg | Gly | Gln | Ala | Ile | Asp | Leu |
| | | 35 | | | | | 40 | | | | | 45 | | | |
| Pro | Asp | Thr | Asp | Pro | Arg | Val | Arg | Arg | Val | Ile | Gly | Phe | Glu | Pro | |
| | 50 | | | | | 55 | | | | | 60 | | | | |
| Glu | Gln | Ile | Ser | Leu | Ser | Leu | Ser | Asp | His | Asp | Ser | Ile | Trp | Val | |
| 65 | | | | | 70 | | | | | 75 | | | | | 80 |
| Ser | Trp | Ile | Thr | Gly | Glu | Phe | Gln | Ile | Gly | Lys | Lys | Val | Lys | Pro | Leu |
| | | | | 85 | | | | | 90 | | | | | 95 | |
| Asp | Pro | Thr | Ser | Ile | Asn | Ser | Val | Val | Gln | Phe | Gly | Thr | Leu | Arg | His |
| | | | 100 | | | | | 105 | | | | | 110 | | |
| Ser | Leu | Ser | His | Glu | Ala | Lys | Gly | His | Ser | Leu | Val | Tyr | Ser | Gln | Leu |
| | | 115 | | | | | 120 | | | | | 125 | | | |
| Tyr | Pro | Phe | Asp | Gly | Leu | Leu | Asn | Tyr | Thr | Ser | Gly | Ile | Ile | His | His |
| | 130 | | | | | 135 | | | | | 140 | | | | |
| Val | Arg | Ile | Thr | Gly | Leu | Lys | Pro | Ser | Thr | Ile | Tyr | Tyr | Tyr | Arg | Cys |
| 145 | | | | | 150 | | | | | 155 | | | | | 160 |
| Gly | Asp | Pro | Ser | Arg | Arg | Ala | Met | Ser | Lys | Ile | His | His | Phe | Arg | Thr |
| | | | | 165 | | | | | 170 | | | | | 175 | |
| Met | Pro | Val | Ser | Ser | Pro | Ser | Ser | Tyr | Pro | Gly | Arg | Ile | Ala | Val | Val |
| | | | 180 | | | | | 185 | | | | | 190 | | |
| Gly | Asp | Leu | Gly | Leu | Thr | Tyr | Asn | Thr | Thr | Asp | Thr | Ile | Ser | His | Leu |
| | | 195 | | | | | 200 | | | | | 205 | | | |
| Ile | His | Asn | Ser | Pro | Asp | Leu | Ile | Leu | Leu | Ile | Gly | Asp | Val | Ser | Tyr |
| | 210 | | | | | 215 | | | | | 220 | | | | |
| Ala | Asn | Leu | Tyr | Leu | Thr | Asn | Gly | Thr | Ser | Ser | Asp | Cys | Tyr | Ser | Cys |
| 225 | | | | | 230 | | | | | 235 | | | | | 240 |
| Ser | Phe | Pro | Glu | Thr | Pro | Ile | His | Glu | Thr | Tyr | Gln | Pro | Arg | Trp | Asp |
| | | | | 245 | | | | | 250 | | | | | 255 | |
| Tyr | Trp | Gly | Arg | Phe | Met | Glu | Asn | Leu | Thr | Ser | Lys | Val | Pro | Leu | Met |
| | | | 260 | | | | | 265 | | | | | 270 | | |
| Val | Ile | Glu | Gly | Asn | His | Glu | Ile | Glu | Leu | Gln | Ala | Glu | Asn | Lys | Thr |
| | | 275 | | | | | 280 | | | | | 285 | | | |
| Phe | Glu | Ala | Tyr | Ser | Ser | Arg | Phe | Ala | Phe | Pro | Asn | Glu | Ser | Gly | |
| | 290 | | | | | 295 | | | | | 300 | | | | |
| Ser | Ser | Ser | Thr | Leu | Tyr | Tyr | Ser | Phe | Asn | Ala | Gly | Gly | Ile | His | Phe |
| 305 | | | | | 310 | | | | | 315 | | | | | 320 |
| Val | Met | Leu | Gly | Ala | Tyr | Ile | Ala | Tyr | Asp | Lys | Ser | Ala | Glu | Gln | Tyr |
| | | | | 325 | | | | | 330 | | | | | 335 | |
| Glu | Trp | Leu | Lys | Lys | Asp | Leu | Ala | Lys | Val | Asp | Arg | Ser | Val | Thr | Pro |

```
                    340                 345                 350
Trp Leu Val Ala Ser Trp His Pro Pro Trp Tyr Ser Ser Tyr Thr Ala
            355                 360                 365
His Tyr Arg Glu Ala Glu Cys Met Lys Glu Ala Met Glu Glu Leu Leu
        370                 375                 380
Tyr Ser Tyr Gly Thr Asp Ile Val Phe Asn Gly His Val His Ala Tyr
385                 390                 395                 400
Glu Arg Ser Asn Arg Val Tyr Asn Tyr Glu Leu Asp Pro Cys Gly Pro
                405                 410                 415
Val Tyr Ile Val Ile Gly Asp Gly Gly Asn Arg Glu Lys Met Ala Ile
            420                 425                 430
Glu His Ala Asp Asp Pro Gly Lys Cys Pro Glu Pro Leu Thr Thr Pro
        435                 440                 445
Asp Pro Val Met Gly Gly Phe Cys Ala Trp Asn Phe Thr Pro Ser Asp
    450                 455                 460
Lys Phe Cys Trp Asp Arg Gln Pro Asp Tyr Ser Ala Leu Arg Glu Ser
465                 470                 475                 480
Ser Phe Gly His Gly Ile Leu Glu Met Lys Asn Glu Thr Trp Ala Leu
                485                 490                 495
Trp Thr Trp Tyr Arg Asn Gln Asp Ser Ser Ser Glu Val Gly Asp Gln
            500                 505                 510
Ile Tyr Ile Val Arg Gln Pro Asp Arg Cys Pro Leu His His Arg Leu
        515                 520                 525
Val Asn His Cys
    530

<210> SEQ ID NO 59
<211> LENGTH: 2115
<212> TYPE: DNA
<213> ORGANISM: Arabidopsis thaliana

<400> SEQUENCE: 59
tcagcgttta tactctgtaa tgccagatcc gcggtaacgc aagtcagtga cctactccgg    60
cgtttatcac tgaatccgat tatggctagt cttcttcgat ccttaatcct tttgctaatc   120
gtgcaatcat ttttggttgc gatcgctttc gggtcgaaag aagttgaaga attcagcgag   180
gcattgctct tgaagccttt acctgatcga aaagttttag ctcacttcca cttcgagaac   240
cgagctcctc cgtcaaactc ccatggccgc catcaccatc tcttcccgaa agctatttct   300
cagttggttc agaagtttcg ggtcaaggag atggagttat cttttactca gggtcgatgg   360
aaccatgaac attggggagg atttgaccct ctatcaagta tgaatgcgaa gcctgttggt   420
gtggagctgt gggctgtgtt tgatgttcct cagtctcagg ttgatacttc ttggaagaac   480
ttaactcatg cactgtcagg gcttttctgt gcttccatca attttctaga atcttccact   540
tcatatgctg ctcctacatg gggatttgga cccaattctg acaagctgag gtatggttca   600
ctgccacgtg aagctgtttg tactgagaac ttgaccccat ggctaaagtt acttccttgt   660
agagataagg atggtatttc tgcgttaatg aataggccat ctgtttacag agggttttat   720
cattctcaga gattgcattt atccacggtt gaatctggtc aagagggatt gggttctggt   780
atagtgctgg agcagacgct tactgttgtt cttcagcctg agactacttc tgttgaatca   840
aatatgcagc caagttggtc cctcagctcc ctctttggga acaagttgt tgggagatgt   900
gttcttgcaa agtcaagtaa tgtgtatctt caattggaag tcttcttgg ttacgaatca   960
aaaaacgtgg atacagaaat agaagcacac caactatgga agaatgcaga gtttgaattg  1020
```

```
tctcttaagc cagagagggt tattcgagaa agctgcagct ttcttttat ttttgatatt    1080
gacaaatcaa gtgacagcga gccatttgat cttggcctta cttggaagcg tccctcaaag   1140
tggtcatgtc aacaagctcc attacactcg agtcggtttt tgatgggaag cgggaacgaa   1200
agaggtgcaa tagccatctt gttaaaagcg acagaatctc aggagaagtt atcaggcaga   1260
gatctcacta atggccaatg tacaataaaa gcaaatatct tccagatttt cccatggtat   1320
attaaggttt attatcatac tctacaaatc tttgtggatc aacaacagaa acagacagt    1380
gaggtcttaa agaagatcaa tgtctcacca tctacggata aggtgtcatc tggcatgatg   1440
gagatgatgt tggaactacc atgtgaagtg aaatctgtag ccatatcaat tgaatatgat   1500
aagggttttc tgcatataga tgaatatcct cctgatgcta atcaaggatt cgacattcca   1560
tcggctttga taagcttccc cgatcatcat gctagtttag atttccaaga gagctcagc    1620
aactcgccct tattatcaag tttaaaggaa aaatccttag tacgctctta cacagaagta   1680
ttgctcgtac ctttgacaac ccctgatttt agcatgcctt acaacgtaat cacgatcaca   1740
tgcaccatct tcgcattgta ttttggatca ttgctaaatg ttctacgtag acgaattggt   1800
gaagaagaaa ggtttctcaa aagccaagga aagaaaacag gtgggcttaa gcagttatta   1860
tcgagaatca cagccaagat tagagggaga ccaattgaag caccatcatc atcagaagct   1920
gaatcttcgg tcttgtctag taaacttatc ttaaaaatca tattagttgc aggagctgct   1980
gcagcgtggc aatattttc cacggacgag taggcttaaa acttttgaag aaataccagt    2040
tgtaccatat gtatcaacaa ggtaatttt ttgggaccgt gtaagatttg ctcttatata    2100
gtttcaaaat tttgc                                                   2115
```

<210> SEQ ID NO 60
<211> LENGTH: 643
<212> TYPE: PRT
<213> ORGANISM: Arabidopsis thaliana

<400> SEQUENCE: 60

```
Met Ala Ser Leu Leu Arg Ser Leu Ile Leu Leu Ile Val Gln Ser
1               5                   10                  15

Phe Leu Val Ala Ile Ala Phe Gly Ser Lys Glu Val Glu Glu Phe Ser
            20                  25                  30

Glu Ala Leu Leu Leu Lys Pro Leu Pro Asp Arg Lys Val Leu Ala His
        35                  40                  45

Phe His Phe Glu Asn Arg Ala Pro Pro Ser Asn Ser His Gly Arg His
    50                  55                  60

His His Leu Phe Pro Lys Ala Ile Ser Gln Leu Val Gln Lys Phe Arg
65                  70                  75                  80

Val Lys Glu Met Glu Leu Ser Phe Thr Gln Gly Arg Trp Asn His Glu
                85                  90                  95

His Trp Gly Gly Phe Asp Pro Leu Ser Ser Met Asn Ala Lys Pro Val
            100                 105                 110

Gly Val Glu Leu Trp Ala Val Phe Asp Val Pro Gln Ser Gln Val Asp
        115                 120                 125

Thr Ser Trp Lys Asn Leu Thr His Ala Leu Ser Gly Leu Phe Cys Ala
    130                 135                 140

Ser Ile Asn Phe Leu Glu Ser Thr Ser Tyr Ala Ala Pro Thr Trp
145                 150                 155                 160

Gly Phe Gly Pro Asn Ser Asp Lys Leu Arg Tyr Gly Ser Leu Pro Arg
                165                 170                 175

Glu Ala Val Cys Thr Glu Asn Leu Thr Pro Trp Leu Lys Leu Leu Pro
```

-continued

```
            180                 185                 190
Cys Arg Asp Lys Asp Gly Ile Ser Ala Leu Met Asn Arg Pro Ser Val
            195                 200                 205

Tyr Arg Gly Phe Tyr His Ser Gln Arg Leu His Leu Ser Thr Val Glu
            210                 215                 220

Ser Gly Gln Glu Gly Leu Gly Ser Gly Ile Val Leu Glu Gln Thr Leu
225                 230                 235                 240

Thr Val Val Leu Gln Pro Glu Thr Thr Ser Val Glu Ser Asn Met Gln
                245                 250                 255

Pro Ser Trp Ser Leu Ser Ser Leu Phe Gly Arg Gln Val Val Gly Arg
            260                 265                 270

Cys Val Leu Ala Lys Ser Ser Asn Val Tyr Leu Gln Leu Glu Gly Leu
            275                 280                 285

Leu Gly Tyr Glu Ser Lys Asn Val Asp Thr Glu Ile Glu Ala His Gln
            290                 295                 300

Leu Trp Lys Asn Ala Glu Phe Glu Leu Ser Leu Lys Pro Glu Arg Val
305                 310                 315                 320

Ile Arg Glu Ser Cys Ser Phe Leu Phe Ile Phe Asp Ile Asp Lys Ser
                325                 330                 335

Ser Asp Ser Glu Pro Phe Asp Leu Gly Leu Thr Trp Lys Arg Pro Ser
            340                 345                 350

Lys Trp Ser Cys Gln Gln Ala Pro Leu His Ser Ser Arg Phe Leu Met
            355                 360                 365

Gly Ser Gly Asn Glu Arg Gly Ala Ile Ala Ile Leu Leu Lys Ala Thr
            370                 375                 380

Glu Ser Gln Glu Lys Leu Ser Gly Arg Asp Leu Thr Asn Gly Gln Cys
385                 390                 395                 400

Thr Ile Lys Ala Asn Ile Phe Gln Ile Phe Pro Trp Tyr Ile Lys Val
                405                 410                 415

Tyr Tyr His Thr Leu Gln Ile Phe Val Asp Gln Gln Lys Thr Asp
            420                 425                 430

Ser Glu Val Leu Lys Lys Ile Asn Val Ser Pro Ser Thr Asp Lys Val
            435                 440                 445

Ser Ser Gly Met Met Glu Met Met Leu Glu Leu Pro Cys Glu Val Lys
450                 455                 460

Ser Val Ala Ile Ser Ile Glu Tyr Asp Lys Gly Phe Leu His Ile Asp
465                 470                 475                 480

Glu Tyr Pro Pro Asp Ala Asn Gln Gly Phe Asp Ile Pro Ser Ala Leu
                485                 490                 495

Ile Ser Phe Pro Asp His His Ala Ser Leu Asp Phe Gln Glu Glu Leu
            500                 505                 510

Ser Asn Ser Pro Leu Leu Ser Ser Leu Lys Glu Lys Ser Leu Val Arg
            515                 520                 525

Ser Tyr Thr Glu Val Leu Leu Val Pro Leu Thr Thr Pro Asp Phe Ser
            530                 535                 540

Met Pro Tyr Asn Val Ile Thr Ile Thr Cys Thr Ile Phe Ala Leu Tyr
545                 550                 555                 560

Phe Gly Ser Leu Leu Asn Val Leu Arg Arg Ile Gly Glu Glu
                565                 570                 575

Arg Phe Leu Lys Ser Gln Gly Lys Lys Thr Gly Leu Lys Gln Leu
            580                 585                 590

Leu Ser Arg Ile Thr Ala Lys Ile Arg Gly Arg Pro Ile Glu Ala Pro
            595                 600                 605
```

```
Ser Ser Ser Glu Ala Glu Ser Ser Val Leu Ser Ser Lys Leu Ile Leu
        610                 615                 620

Lys Ile Ile Leu Val Ala Gly Ala Ala Ala Ala Trp Gln Tyr Phe Ser
625                 630                 635                 640

Thr Asp Glu

<210> SEQ ID NO 61
<211> LENGTH: 2121
<212> TYPE: DNA
<213> ORGANISM: Arabidopsis thaliana

<400> SEQUENCE: 61
```

| | | | | | |
|---|---|---|---|---|---|
| tcagcgttta | tactctgtaa | tgccagatcc | gcggtaacgc | aagtcagtga | cctactccgg | 60 |
| cgtttatcac | tgaatccgat | tatggctagt | cttcttcgat | ccttaatcct | tttgctaatc | 120 |
| gtgcaatcat | ttttggttgc | gatcgctttc | gggtcgaaag | aagttgaaga | attcagcgag | 180 |
| gcattgctct | tgaagccttt | acctgatcga | aaagttttag | ctcacttcca | cttcgagaac | 240 |
| cgagctcctc | cgtcaaactc | ccatggccgc | catcaccatc | tcttcccgaa | agctatttct | 300 |
| cagttggttc | agaagtttcg | ggtcaaggag | atggagttat | cttttactca | gggtcgatgg | 360 |
| aaccatgaac | attggggagg | atttgaccct | ctatcaagta | tgaatgcgaa | gcctgttggt | 420 |
| gtggagctgt | gggctgtgtt | tgatgttcct | cagtctcagg | ttgatacttc | ttggaagaac | 480 |
| ttaactcatg | cactgtcagg | gcttttctgt | gcttccatca | ttttctaga | atcttccact | 540 |
| tcatatgctg | ctcctacatg | gggatttgga | cccaattctg | acaagctgag | gtatggttca | 600 |
| ctgccacgtg | aagctgtttg | tactgagaac | ttgaccccat | ggctaaagtt | acttccttgt | 660 |
| agagataagg | atggtatttc | tgcgttaatg | aataggccat | ctgtttacag | agggttttat | 720 |
| cattctcaga | gattgcattt | atccacggtt | gaatctggtc | aagagggatt | gggttctggt | 780 |
| atagtgctgg | agcagacgct | tactgttgtt | cttcagcctg | agactacttc | tgttgaatca | 840 |
| aatatgcagc | caagttggtc | cctcagctcc | ctctttggga | acaagttgt | tgggagatgt | 900 |
| gttcttgcaa | agtcaagtaa | tgtgtatctt | caattggaag | gtcttcttgg | ttacgaatca | 960 |
| aaaaacgtgg | atacagaaat | agaagcacac | caactatgga | gaatgcaga | gtttgaattg | 1020 |
| tctcttaagc | cagagagggt | tattcgagaa | agctgcagct | ttcttttat | ttttgatatt | 1080 |
| gacaaatcaa | gtgacagcga | gccatttgat | cttggcctta | cttggaagcg | tccctcaaag | 1140 |
| tggtcatgtc | aacaagctcc | attacactcg | agtcggtttt | tgatgggaag | cgggaacgaa | 1200 |
| agaggtgcaa | tagccatctt | gttaaaagcg | acagaatctc | aggagaagtt | atcaggcaga | 1260 |
| gatctcacta | atggccaatg | tacaataaaa | gcaaatatct | tccagatttt | cccatggtat | 1320 |
| attaaggttt | attatcatac | tctacaaatc | tttgtggatc | aacaacagaa | gacagacagt | 1380 |
| gaggtcttaa | agaagatcaa | tgtctcacca | tctacggata | aggtgtcatc | tggcatgatg | 1440 |
| gagatgatgt | tggaactacc | atgtgaagtg | aaatctgtag | ccatatcaat | tgaatatgat | 1500 |
| aagggttttc | tgcatataga | tgaatatcct | cctgatgcta | atcaaggatt | cgacattcca | 1560 |
| tcggctttga | taagcttccc | cgatcatcat | gctagtttag | atttccaaga | agagctcagc | 1620 |
| aactcgccct | tattatcaag | tttaaaggaa | aaatccttag | tacgctctta | cacagaagta | 1680 |
| ttgctcgtac | ctttgacaac | ccctgatttt | agcatgcctt | acaacgtaat | cacgatcaca | 1740 |
| tgcaccatct | tcgcattgta | ttttggatca | ttgctaaatg | ttctacgtag | acgaattggt | 1800 |
| gaagaagaaa | ggtttctcaa | aagccaagca | ggaaagaaaa | caggtgggct | taagcagtta | 1860 |
| ttatcgagaa | tcacagccaa | gattagaggg | agaccaattg | aagcaccatc | atcatcagaa | 1920 |

-continued

```
gctgaatctt cggtcttgtc tagtaaactt atcttaaaaa tcatattagt tgcaggagct    1980
gctgcagcgt ggcaatattt ttccacggac gagtaggctt aaaacttttg aagaaatacc    2040
agttgtacca tatgtatcaa caaggtaatt ttttgggac cgtgtaagat ttgctcttat     2100
atagtttcaa aattttgcat t                                              2121
```

<210> SEQ ID NO 62
<211> LENGTH: 644
<212> TYPE: PRT
<213> ORGANISM: Arabidopsis thaliana

<400> SEQUENCE: 62

```
Met Ala Ser Leu Leu Arg Ser Leu Ile Leu Leu Ile Val Gln Ser
1               5                   10                  15

Phe Leu Val Ala Ile Ala Phe Gly Ser Lys Glu Val Glu Glu Phe Ser
            20                  25                  30

Glu Ala Leu Leu Leu Lys Pro Leu Pro Asp Arg Lys Val Leu Ala His
        35                  40                  45

Phe His Phe Glu Asn Arg Ala Pro Pro Ser Asn Ser His Gly Arg His
    50                  55                  60

His His Leu Phe Pro Lys Ala Ile Ser Gln Leu Val Gln Lys Phe Arg
65                  70                  75                  80

Val Lys Glu Met Glu Leu Ser Phe Thr Gln Gly Arg Trp Asn His Glu
                85                  90                  95

His Trp Gly Gly Phe Asp Pro Leu Ser Ser Met Asn Ala Lys Pro Val
            100                 105                 110

Gly Val Glu Leu Trp Ala Val Phe Asp Val Pro Gln Ser Gln Val Asp
        115                 120                 125

Thr Ser Trp Lys Asn Leu Thr His Ala Leu Ser Gly Leu Phe Cys Ala
    130                 135                 140

Ser Ile Asn Phe Leu Glu Ser Ser Thr Ser Tyr Ala Ala Pro Thr Trp
145                 150                 155                 160

Gly Phe Gly Pro Asn Ser Asp Lys Leu Arg Tyr Gly Ser Leu Pro Arg
                165                 170                 175

Glu Ala Val Cys Thr Glu Asn Leu Thr Pro Trp Leu Lys Leu Leu Pro
            180                 185                 190

Cys Arg Asp Lys Asp Gly Ile Ser Ala Leu Met Asn Arg Pro Ser Val
        195                 200                 205

Tyr Arg Gly Phe Tyr His Ser Gln Arg Leu His Leu Ser Thr Val Glu
    210                 215                 220

Ser Gly Gln Glu Gly Leu Gly Ser Gly Ile Val Leu Glu Gln Thr Leu
225                 230                 235                 240

Thr Val Val Leu Gln Pro Glu Thr Thr Ser Val Glu Ser Asn Met Gln
                245                 250                 255

Pro Ser Trp Ser Leu Ser Ser Leu Phe Gly Arg Gln Val Val Gly Arg
            260                 265                 270

Cys Val Leu Ala Lys Ser Ser Asn Val Tyr Leu Gln Leu Glu Gly Leu
        275                 280                 285

Leu Gly Tyr Glu Ser Lys Asn Val Asp Thr Glu Ile Glu Ala His Gln
    290                 295                 300

Leu Trp Lys Asn Ala Glu Phe Glu Leu Ser Leu Lys Pro Glu Arg Val
305                 310                 315                 320

Ile Arg Glu Ser Cys Ser Phe Leu Phe Ile Phe Asp Ile Asp Lys Ser
                325                 330                 335

Ser Asp Ser Glu Pro Phe Asp Leu Gly Leu Thr Trp Lys Arg Pro Ser
```

-continued

```
                340                 345                 350
Lys Trp Ser Cys Gln Gln Ala Pro Leu His Ser Arg Phe Leu Met
            355                 360                 365
Gly Ser Gly Asn Glu Arg Gly Ala Ile Ala Ile Leu Leu Lys Ala Thr
        370                 375                 380
Glu Ser Gln Glu Lys Leu Ser Gly Arg Asp Leu Thr Asn Gly Gln Cys
385                 390                 395                 400
Thr Ile Lys Ala Asn Ile Phe Gln Ile Phe Pro Trp Tyr Ile Lys Val
                405                 410                 415
Tyr Tyr His Thr Leu Gln Ile Phe Val Asp Gln Gln Gln Lys Thr Asp
            420                 425                 430
Ser Glu Val Leu Lys Lys Ile Asn Val Ser Pro Ser Thr Asp Lys Val
        435                 440                 445
Ser Ser Gly Met Met Glu Met Met Leu Glu Leu Pro Cys Glu Val Lys
    450                 455                 460
Ser Val Ala Ile Ser Ile Glu Tyr Asp Lys Gly Phe Leu His Ile Asp
465                 470                 475                 480
Glu Tyr Pro Pro Asp Ala Asn Gln Gly Phe Asp Ile Pro Ser Ala Leu
                485                 490                 495
Ile Ser Phe Pro Asp His His Ala Ser Leu Asp Phe Gln Glu Glu Leu
            500                 505                 510
Ser Asn Ser Pro Leu Leu Ser Ser Leu Lys Glu Lys Ser Leu Val Arg
        515                 520                 525
Ser Tyr Thr Glu Val Leu Leu Val Pro Leu Thr Thr Pro Asp Phe Ser
    530                 535                 540
Met Pro Tyr Asn Val Ile Thr Ile Thr Cys Thr Ile Phe Ala Leu Tyr
545                 550                 555                 560
Phe Gly Ser Leu Leu Asn Val Leu Arg Arg Arg Ile Gly Glu Glu
                565                 570                 575
Arg Phe Leu Lys Ser Gln Ala Gly Lys Lys Thr Gly Leu Lys Gln
            580                 585                 590
Leu Leu Ser Arg Ile Thr Ala Lys Ile Arg Gly Arg Pro Ile Glu Ala
        595                 600                 605
Pro Ser Ser Ser Glu Ala Glu Ser Ser Val Leu Ser Ser Lys Leu Ile
    610                 615                 620
Leu Lys Ile Ile Leu Val Ala Gly Ala Ala Ala Trp Gln Tyr Phe
625                 630                 635                 640
Ser Thr Asp Glu

<210> SEQ ID NO 63
<211> LENGTH: 600
<212> TYPE: DNA
<213> ORGANISM: Arabidopsis thaliana

<400> SEQUENCE: 63
atggcgggag actcaggtcg gaggaagatc aaactttct gtccctcggt atcgaagatt    60
gtggagtggg ttgcttggaa cgacgagaaa ctagacttta gagccatagc cgcagcgttt   120
gggctcgaac catcaacggt gaagctcaat ggtcacttca taagcagagg ttttgatcta   180
gttgccactt gtgtgacgtg gcagtctttg ctcactttct ctctgctag aggcttgtct   240 actgaaaaac acgaagccga tgctctgcta gttcacggca agctctctaa actcggtact   300
aaaagagcac gctcggatcc tctgaggac ttcgcctgca atgatcttgg tctaatcaaa    360
acgaagaagt tgaaagataa gtgctcagtt ggagaatcac tgatctctgg atgcaacaag   420
```

```
agaaagctgt tgtctgaaga ttcacaccca ctcaagaaac taaaactcaa catggatgat    480
agtttcggag ggagcggatc taaaacgcca ttgaaatgca gtttcatgag tgataatggt    540
ctgaagagga caagagaaga tgatatgatt gcttctgcat cttgtaagaa gataagatga    600
```

<210> SEQ ID NO 64
<211> LENGTH: 199
<212> TYPE: PRT
<213> ORGANISM: Arabidopsis thaliana

<400> SEQUENCE: 64

```
Met Ala Gly Asp Ser Gly Arg Arg Lys Ile Lys Leu Phe Cys Pro Ser
1               5                   10                  15

Val Ser Lys Ile Val Glu Trp Val Ala Trp Asn Asp Glu Lys Leu Asp
            20                  25                  30

Phe Arg Ala Ile Ala Ala Ala Phe Gly Leu Glu Pro Ser Thr Val Lys
        35                  40                  45

Leu Asn Gly His Phe Ile Ser Arg Gly Phe Asp Leu Val Ala Thr Cys
    50                  55                  60

Val Thr Trp Gln Ser Leu Leu Thr Phe Phe Ser Ala Arg Gly Leu Ser
65                  70                  75                  80

Thr Gly Lys His Glu Ala Asp Ala Leu Leu Val His Gly Lys Leu Ser
                85                  90                  95

Lys Leu Gly Thr Lys Arg Ala Arg Ser Asp Pro Leu Glu Asp Phe Ala
            100                 105                 110

Cys Asn Asp Leu Gly Leu Ile Lys Thr Lys Lys Leu Lys Asp Lys Cys
        115                 120                 125

Ser Val Gly Glu Ser Leu Ile Ser Gly Cys Asn Lys Arg Lys Leu Leu
    130                 135                 140

Ser Glu Asp Ser His Pro Leu Lys Lys Leu Lys Leu Asn Met Asp Asp
145                 150                 155                 160

Ser Phe Gly Gly Ser Gly Ser Lys Thr Pro Leu Lys Cys Ser Phe Met
                165                 170                 175

Ser Asp Asn Gly Leu Lys Arg Thr Arg Glu Asp Asp Met Ile Ala Ser
            180                 185                 190

Ala Ser Cys Lys Lys Ile Arg
        195
```

<210> SEQ ID NO 65
<211> LENGTH: 890
<212> TYPE: DNA
<213> ORGANISM: Arabidopsis thaliana

<400> SEQUENCE: 65

```
gtctctttga cttcatcgtc gattaaggga gaaagagaga gagagtgaga gctgagaaaa     60
tcaccagaaa gctacttgag agagagagat agagataagt gagctctgag aaaatccagc    120
aatggcttcg aagcttgtag tgataattgt gtttatcctc gatctcatcg ccgttgggtt    180
agccattgcc gccgagcaga aagaagtgt cggcaaggtt gaaacagaca gagacaagca    240
atatgattac tgtgtgtatg gtactgacat tgctacaagt tatggagctg gtgcatttgt    300
tcttctcttt gtaagccaag tccttattat ggctgctagt cgttgcttct gttgtggaaa    360
gtctcttaac cctggcggtt caagagcttg tgccattatt ctcttcctca tttgctgggt    420
gtttttcttg atcgctgaga tgtgtttgct tgcggcatca atcagaaatg cgtaccacac    480
acagtataga aagatgtgga agttgaaga tccaccaagc tgtgaagtta taggaaaagg    540 agttttttgca gctggtgctg cattcacact cttcaccgcc attgtctctc agttctacta    600
```

```
cgtttgctac tctcgtgcta gagatgcgta ccagaatccc tcctactaaa aatgtcaact    660
tccacagcaa gcaaacgttt aagcatcaag agttggaatt tgtcttttg tgtttgttta     720 gtattgtcca gtgtttagtt atcctatcag gatgtttagg ttttatgttg tctcttaagc    780
aaacactgat atgttatatt ctaagattcg tatattgtta tgttctctgt tgtaatgtgt    840
gaatgaatac taaagaatag aaaaccatga tttgttgtga tcactgtttt               890
```

<210> SEQ ID NO 66
<211> LENGTH: 175
<212> TYPE: PRT
<213> ORGANISM: Arabidopsis thaliana

<400> SEQUENCE: 66

```
Met Ala Ser Lys Leu Val Val Ile Ile Val Phe Ile Leu Asp Leu Ile
1               5                   10                  15

Ala Val Gly Leu Ala Ile Ala Ala Glu Gln Arg Arg Ser Val Gly Lys
                20                  25                  30

Val Glu Thr Asp Arg Asp Lys Gln Tyr Asp Tyr Cys Val Tyr Gly Thr
            35                  40                  45

Asp Ile Ala Thr Ser Tyr Gly Ala Gly Ala Phe Val Leu Leu Phe Val
        50                  55                  60

Ser Gln Val Leu Ile Met Ala Ala Ser Arg Cys Phe Cys Cys Gly Lys
65                  70                  75                  80

Ser Leu Asn Pro Gly Gly Ser Arg Ala Cys Ala Ile Ile Leu Phe Leu
                85                  90                  95

Ile Cys Trp Val Phe Phe Leu Ile Ala Glu Met Cys Leu Leu Ala Ala
                100                 105                 110

Ser Ile Arg Asn Ala Tyr His Thr Gln Tyr Arg Lys Met Trp Lys Val
            115                 120                 125

Glu Asp Pro Pro Ser Cys Glu Val Ile Arg Lys Gly Val Phe Ala Ala
        130                 135                 140

Gly Ala Ala Phe Thr Leu Phe Thr Ala Ile Val Ser Gln Phe Tyr Tyr
145                 150                 155                 160

Val Cys Tyr Ser Arg Ala Arg Asp Ala Tyr Gln Asn Pro Ser Tyr
                165                 170                 175
```

<210> SEQ ID NO 67
<211> LENGTH: 1297
<212> TYPE: DNA
<213> ORGANISM: Arabidopsis thaliana

<400> SEQUENCE: 67

```
gtatattgca attttgatac tataacacaa cgatgatttc attgattgtc cttactaaaa    60
ctgaaatctt gattaaaaaa tatcaggcga cgattaaatt gccgcctcta ataaatggaa    120
tattgcaaac tcatgattca tgaaatgctt tttgtattcc ctttagttaa gttactgatg    180
aatctgttaa tacaaggaac gttaatgcat ttagattttc acatttcata ttggaaagga    240
aaatgcgggg ttttccagat ttaatacaca aagtaaatcc tcctagtaat tatctttaat    300
gtaccacttt ttaaggataa tatatgtaga tttcttgcta tatatattca catctcatta    360
ttaggcctta cttataagaa tctgttcaca ttccttcacag aggaaagtaa atcatgtttg    420
ccaagaaacc agaatcaaag tttgggtgct tttttaacat atttggtgtt cttcggtctc    480
gttcttcaag atggcgaaaa gcttcgaagt ggtaagaatc ttggtttact tgctttacac    540
ggttaagatt tcgttttgt ttcgagtttt ttttaattaa ttaatctgtc ttgtttgcag     600
```

-continued

```
caaactctat atccaaaatc tgttatgttc gttaacttaa catcggaata aagagagtg    660 tatggtcaga caatcacggt ccgatatcgc tcagctcctt tcttatggtc gctattcaga    720
agctcttcct aaggcgaagc aattctatga agatgagaga aggttatcgg catatgatca    780
ggttgagctc ttctgcacaa ccatcttgca gaatatatct tctttgaaat atgaaaacaa    840
tgttgatctg ttaccggaag aaactaaaaa agcaatggcc ggaattatat tgctgcatc    900 aagaattggc gagcttgagg atcttcaaca cataaggagc ttcttcgttc aaagatttgg    960
gcttaagttt gataaagagt gtgtagattt gcgccaagga acgtcgtgg gttttgagat    1020 agtcaagatt ctaaacacga atatgcgggg agatgaaatt acacatattg taagggaact    1080
ttctcataag tacaaaacca acatcactac ttctacggat tcaataagtg aagatttggc    1140
ttcaagtgac gatctcggca ttgccgattc tgatgcgatg aaggttgaga aaatgaaaag    1200
ggctcttcgg agaaagaaag ttatgaagga gaattctaag ttttttgcatc caaatcttag    1260 agagtctcag ggaagagatc gatcattcag aagataa                           1297
```

<210> SEQ ID NO 68
<211> LENGTH: 211
<212> TYPE: PRT
<213> ORGANISM: Arabidopsis thaliana

<400> SEQUENCE: 68

```
Met Val Arg Gln Ser Arg Ser Asp Ile Ala Gln Leu Leu Ser Tyr Gly
1               5                   10                  15

Arg Tyr Ser Glu Ala Leu Pro Lys Ala Lys Gln Phe Tyr Glu Asp Glu
                20                  25                  30

Arg Arg Leu Ser Ala Tyr Asp Gln Val Glu Leu Phe Cys Thr Thr Ile
            35                  40                  45

Leu Gln Asn Ile Ser Ser Leu Lys Tyr Glu Asn Asn Val Asp Leu Leu
        50                  55                  60

Pro Glu Glu Thr Lys Lys Ala Met Ala Gly Ile Ile Phe Ala Ala Ser
65                  70                  75                  80

Arg Ile Gly Glu Leu Glu Asp Leu Gln His Ile Arg Ser Phe Phe Val
                85                  90                  95

Gln Arg Phe Gly Leu Lys Phe Asp Lys Glu Cys Val Asp Leu Arg Gln
            100                 105                 110

Gly Asn Val Val Gly Phe Glu Ile Val Lys Ile Leu Asn Thr Asn Met
        115                 120                 125

Arg Gly Asp Glu Ile Thr His Ile Val Arg Glu Leu Ser His Lys Tyr
    130                 135                 140

Lys Thr Asn Ile Thr Thr Ser Thr Asp Ser Ile Ser Glu Asp Leu Ala
145                 150                 155                 160

Ser Ser Asp Asp Leu Gly Ile Ala Asp Ser Asp Ala Met Lys Val Glu
                165                 170                 175

Lys Met Lys Arg Ala Leu Arg Lys Lys Val Met Lys Glu Asn Ser
            180                 185                 190

Lys Phe Leu His Pro Asn Leu Arg Glu Ser Gln Gly Arg Asp Arg Ser
        195                 200                 205

Phe Arg Arg
    210
```

<210> SEQ ID NO 69
<211> LENGTH: 1271
<212> TYPE: DNA
<213> ORGANISM: Arabidopsis thaliana

<400> SEQUENCE: 69

```
atctttaatc tcagaataca aaaagaaaa tcaaagaaga tagttttgtg attgttttct      60
ataaaaagtg cagatatttt ctttgtccta gagaagagg tgataggaaa atgggtctc      120
caagagcttg acccgttagc ccaattgagc ttaccgccgg gttttcggtt ttatccgact    180
gacgaagagc tgatggttga atatctctgt agaaaagccg ccggtcacga cttctctctc    240
cagctcatag ctgaaatcga tctctacaag tttgatccat gggttttacc aagtaaggcg    300
ttattcggtg aaaagaatg gtattttttc agcccgaggg ataggaagta ccaaacggg     360
tcaagaccta atcgggttgc cgggtcgggt tattggaaag ccaccggtac ggataaagtt    420
atctcgacgg agggaagaag agttggtatc aagaaagctt tggtgtttta cattggaaaa   480
gctccaaaag gaaccaaaac caattggatt atgcatgagt accgtctcat cgaaccctct    540
cgtcgaaatg gaagcaccaa gcttgatgat tgggttttat gtcgaatata caaaaagcaa    600
acaagcgcac aaaaacaagc ttacaataat ctaatgacga gtggtcgtga atacagcaac    660
aatggttcgt cgacatcttc ttcgtctcat caatacgacg acgttctcga gtcgttgcat   720
gagattgaca acagaagttt gggttttgcc gccggttcat caaacgcgct gcctcatagt    780
catagaccgg ttttaaccaa tcataaaacc gggtttcagg gtttagccag ggagccaagt    840
tttgattggg cgaatttgat tggacagaac tcggtcccgg aactcggact gagtcataac    900
gttccgagta ttcgttacgg tgacggtgga acgcagcaac aaactgaggg gattcctcgg    960
tttaataata actcggacgt ctcggctaat cagggtttta gtgttgaccc ggttaacgga   1020
tttgggtact cgggtcaaca atctagtggg ttcgggttta tttgattgtg taatggtaac   1080
gtaataagaa aaacatattt ttattttttg tccgtgtcag attagttaat taatatagcg   1140
tagaattcga actctagggt tagatttagg ttctacgact tgtattgtat attcgtcgtc   1200
atttgtcctg acatttacat ttttgtaaac ttttatagct ggaacttttg tattgatcaa   1260
ttatttatta g                                                         1271
```

<210> SEQ ID NO 70
<211> LENGTH: 317
<212> TYPE: PRT
<213> ORGANISM: Arabidopsis thaliana

<400> SEQUENCE: 70

```
Met Gly Leu Gln Glu Leu Asp Pro Leu Ala Gln Leu Ser Leu Pro Pro
1               5                   10                  15

Gly Phe Arg Phe Tyr Pro Thr Asp Glu Glu Leu Met Val Glu Tyr Leu
            20                  25                  30

Cys Arg Lys Ala Ala Gly His Asp Phe Ser Leu Gln Leu Ile Ala Glu
        35                  40                  45

Ile Asp Leu Tyr Lys Phe Asp Pro Trp Val Leu Pro Ser Lys Ala Leu
    50                  55                  60

Phe Gly Glu Lys Glu Trp Tyr Phe Phe Ser Pro Arg Asp Arg Lys Tyr
65                  70                  75                  80

Pro Asn Gly Ser Arg Pro Asn Arg Val Ala Gly Ser Gly Tyr Trp Lys
                85                  90                  95

Ala Thr Gly Thr Asp Lys Val Ile Ser Thr Glu Gly Arg Arg Val Gly
            100                 105                 110

Ile Lys Lys Ala Leu Val Phe Tyr Ile Gly Lys Ala Pro Lys Gly Thr
        115                 120                 125

Lys Thr Asn Trp Ile Met His Glu Tyr Arg Leu Ile Glu Pro Ser Arg
    130                 135                 140
```

| Arg | Asn | Gly | Ser | Thr | Lys | Leu | Asp | Asp | Trp | Val | Leu | Cys | Arg | Ile | Tyr |
| 145 | | | | | 150 | | | | | 155 | | | | | 160 |

| Lys | Lys | Gln | Thr | Ser | Ala | Gln | Lys | Gln | Ala | Tyr | Asn | Asn | Leu | Met | Thr |
| | | | | 165 | | | | | 170 | | | | | 175 | |

| Ser | Gly | Arg | Glu | Tyr | Ser | Asn | Asn | Gly | Ser | Ser | Thr | Ser | Ser | Ser | Ser |
| | | | 180 | | | | | 185 | | | | | 190 | | |

| His | Gln | Tyr | Asp | Asp | Val | Leu | Glu | Ser | Leu | His | Glu | Ile | Asp | Asn | Arg |
| | | | 195 | | | | | 200 | | | | | 205 | | |

| Ser | Leu | Gly | Phe | Ala | Ala | Gly | Ser | Ser | Asn | Ala | Leu | Pro | His | Ser | His |
| | 210 | | | | | 215 | | | | | 220 | | | | |

| Arg | Pro | Val | Leu | Thr | Asn | His | Lys | Thr | Gly | Phe | Gln | Gly | Leu | Ala | Arg |
| 225 | | | | | 230 | | | | | 235 | | | | | 240 |

| Glu | Pro | Ser | Phe | Asp | Trp | Ala | Asn | Leu | Ile | Gly | Gln | Asn | Ser | Val | Pro |
| | | | | 245 | | | | | 250 | | | | | 255 | |

| Glu | Leu | Gly | Leu | Ser | His | Asn | Val | Pro | Ser | Ile | Arg | Tyr | Gly | Asp | Gly |
| | | | 260 | | | | | 265 | | | | | 270 | | |

| Gly | Thr | Gln | Gln | Gln | Thr | Glu | Gly | Ile | Pro | Arg | Phe | Asn | Asn | Asn | Ser |
| | | | 275 | | | | | 280 | | | | | 285 | | |

| Asp | Val | Ser | Ala | Asn | Gln | Gly | Phe | Ser | Val | Asp | Pro | Val | Asn | Gly | Phe |
| | 290 | | | | | 295 | | | | | 300 | | | | |

| Gly | Tyr | Ser | Gly | Gln | Gln | Ser | Ser | Gly | Phe | Gly | Phe | Ile | | | |
| 305 | | | | | 310 | | | | | 315 | | | | | |

<210> SEQ ID NO 71
<211> LENGTH: 1371
<212> TYPE: DNA
<213> ORGANISM: Arabidopsis thaliana

<400> SEQUENCE: 71

| | |
|---|---|
| gactgaaaac aaacgaccct aatggctcat gaggagaagc gcccatggga gttttctta | 60 |
| tctcttccat gggagttgat tgaagagata ctctctcgtg tcccaccaga atctcttctt | 120 |
| cgcttcaaaa ccgtatcgaa acaatggaac gctctcttcc gcgataagac gttcatcaat | 180 |
| aaccacaaga tgacgtttcg attcatctta gcaaccaaat ccaagattta ttcggtaagc | 240 |
| atcgatccca agatagttgt gcgtgagtta accttagata ttcccggttt agaatctcat | 300 |
| gagataccta aaaaattggt tgattgcgat aagttattac tatgtgacat ggagaaagga | 360 |
| gttgtgcttt ggaacccgtg gctgagacat agtacatgga tcgaccaggg ttcaaaccac | 420 |
| actcgaatgg agtcttatgg cataggatac aacaataagg ggagttacaa gatctttgct | 480 |
| ttttgtgatc ggaaggaaaa ccacacccag agattgttga caatccatga ctctgcctct | 540 |
| gatgcgtgga agaccgcga gcctattgat aatagtcagg gaaaacaaat tgttcataac | 600 |
| atatacacta aaattagtgg tgtatcattg aatggaaatt tgtatttggt tacttatttt | 660 |
| gaaacgactg atctcgtgta ccacctaatt gaaatcaatt cttcgagcga aagcgtcgtg | 720 |
| aagttttgtg atctaccatg tgggacgtcg aactttctta aggatgcttt cgtccttagg | 780 |
| gttttcgagg gagatcgatt ttcattgtta aagcaatgcc atgcaacaaa gaagattgag | 840 |
| atttgggtga gcaagtacaa gattaataat aatcttgata gagatgtgga atggataaag | 900 |
| ttcatggaag tttcaagtcc taacttgccg gatttagtag atggattcga ctctcagcca | 960 |
| agttacttta ttgaagataa aaggctcgtc gtgtgctcgt gcaacgaaac tggtcgggct | 1020 |
| tggatctatg ttttcggaga aaataagttg atcagtaaaa ctcaaattga ttctgtggtg | 1080 |
| gatctttggc cttcacactg gacctttatt cccagtttgg taccggttcc tcgagctcaa | 1140 |

```
agagaagaac cagcagaatt acaagtttga ttttagttac attttagctt cttgtttggt    1200
tgttgaggaa gctaaatttt atttggattt cagtattttt attcacaaac catcttcttt    1260
gttgctgata attgattaat ctcccttttct ttgttttgta gcttcttttg gcaaaataaa    1320
ttcttaataa tgtatccttt agataaatct agagagaatg tttaaggact c             1371
```

<210> SEQ ID NO 72
<211> LENGTH: 382
<212> TYPE: PRT
<213> ORGANISM: Arabidopsis thaliana

<400> SEQUENCE: 72

```
Met Ala His Glu Glu Lys Arg Pro Trp Glu Phe Ser Leu Ser Leu Pro
1               5                   10                  15

Trp Glu Leu Ile Glu Glu Ile Leu Ser Arg Val Pro Pro Glu Ser Leu
            20                  25                  30

Leu Arg Phe Lys Thr Val Ser Lys Gln Trp Asn Ala Leu Phe Arg Asp
        35                  40                  45

Lys Thr Phe Ile Asn Asn His Lys Met Thr Phe Arg Phe Ile Leu Ala
    50                  55                  60

Thr Lys Ser Lys Ile Tyr Ser Val Ser Ile Asp Pro Lys Ile Val Val
65                  70                  75                  80

Arg Glu Leu Thr Leu Asp Ile Pro Gly Leu Glu Ser His Glu Ile Pro
                85                  90                  95

Lys Lys Leu Val Asp Cys Asp Lys Leu Leu Leu Cys Asp Met Glu Lys
            100                 105                 110

Gly Val Val Leu Trp Asn Pro Trp Leu Arg His Ser Thr Trp Ile Asp
        115                 120                 125

Gln Gly Ser Asn His Thr Arg Met Glu Ser Tyr Gly Ile Gly Tyr Asn
    130                 135                 140

Asn Lys Gly Ser Tyr Lys Ile Phe Ala Phe Cys Asp Arg Lys Glu Asn
145                 150                 155                 160

His Thr Gln Arg Leu Leu Thr Ile His Asp Ser Ala Ser Asp Ala Trp
                165                 170                 175

Lys Asp Arg Glu Pro Ile Asp Asn Ser Gln Gly Lys Gln Ile Val His
            180                 185                 190

Asn Ile Tyr Thr Lys Ile Ser Gly Val Ser Leu Asn Gly Asn Leu Tyr
        195                 200                 205

Leu Val Thr Tyr Phe Glu Thr Thr Asp Leu Val Tyr His Leu Ile Glu
    210                 215                 220

Ile Asn Ser Ser Ser Glu Ser Val Val Lys Phe Cys Asp Leu Pro Cys
225                 230                 235                 240

Gly Thr Ser Asn Phe Leu Lys Asp Ala Phe Val Leu Arg Val Phe Glu
                245                 250                 255

Gly Asp Arg Phe Ser Leu Leu Lys Gln Cys His Ala Thr Lys Lys Ile
            260                 265                 270

Glu Ile Trp Val Ser Lys Tyr Lys Ile Asn Asn Leu Asp Arg Asp
        275                 280                 285

Val Glu Trp Ile Lys Phe Met Glu Val Ser Ser Pro Asn Leu Pro Asp
    290                 295                 300

Leu Val Asp Gly Phe Asp Ser Gln Pro Ser Tyr Phe Ile Glu Asp Lys
305                 310                 315                 320

Arg Leu Val Val Cys Ser Cys Asn Glu Thr Gly Arg Ala Trp Ile Tyr
                325                 330                 335

Val Phe Gly Glu Asn Lys Leu Ile Ser Lys Thr Gln Ile Asp Ser Val
```

```
                340             345             350
Val Asp Leu Trp Pro Ser His Trp Thr Phe Ile Pro Ser Leu Val Pro
        355                 360                 365

Val Pro Arg Ala Gln Arg Glu Glu Pro Ala Glu Leu Gln Val
    370                 375                 380
```

<210> SEQ ID NO 73
<211> LENGTH: 1125
<212> TYPE: DNA
<213> ORGANISM: Arabidopsis thaliana

<400> SEQUENCE: 73

```
atgccgacga agcttccact ggagttggag gatgagatac ttttgcgtgt tccacctcta      60
tctctcacac gctttagaac agtttgcaaa cgatggaaca cacttttcaa cgatcagaga    120
ttcatcaaca atcacttggc ttgcgtccgt cctcagttca tattacggac cgagaaagat    180
tccaagatct attcaatagg catcaatatc gatgactcct tagaggtgcg tgagctaaac    240
ctagaaactc aaggtcctaa taagaagctt aaggtatatc gaaacctctt ttattgcgat    300
ggttttttgt tatgtcctgc tttgcttgac gaggttgctg tctggaatcc atggttgaga    360
aaacaaacta aatggatcga gcctaagagg agtagattca atttatatgg actagggtat    420
gataatcgta gccggagaa gtgttacaag atcttagggt ttggttatgg ttacagtagt      480
gaaataaacg gtagttacaa cagaattaac ccgagagttt cggtatttga gtttgaaact    540
aatgcgtgga aggatcttaa gtttggttta tttgattggc acctaagatc tccccggact    600
gttttatctt tgaatggaac tttgtattgg attgctgtga ggtgtgaaag tggtggtgat    660
ggttttatcc aaagctttga cttttcgagg gagatgttcg agcccttttg tctcttgcca    720
tgtaagaacg attttggcga tactcaaatc cttgaggttt tagggaga tcggctatct    780
gtgttggaac aatgcccgac aacaaataag atcaagattt gggtgactaa gaacaagatt    840
agtggagata ggaaggagct tgtgtcgtgg agactgttaa tgacagtgtc gataccaaac    900
ttcccgagat acaagatcct ttactctaat tctcagccga gttacttcat ggataacaat    960
gatgacaaga ggctcatcgt gtgtacttgt gatgaaagtg gtaagccttg catatacatt   1020
gtgaagggg ataggttcaa gaagattcaa atgggtttg aggttgagcc ttggccttt      1080
cacccttgttt atgttcctag tttggttcct attccttag cctaa                   1125
```

<210> SEQ ID NO 74
<211> LENGTH: 374
<212> TYPE: PRT
<213> ORGANISM: Arabidopsis thaliana

<400> SEQUENCE: 74

```
Met Pro Thr Lys Leu Pro Leu Glu Leu Glu Asp Glu Ile Leu Leu Arg
1               5                   10                  15

Val Pro Pro Leu Ser Leu Thr Arg Phe Arg Thr Val Cys Lys Arg Trp
            20                  25                  30

Asn Thr Leu Phe Asn Asp Gln Arg Phe Ile Asn Asn His Leu Ala Cys
        35                  40                  45

Val Arg Pro Gln Phe Ile Leu Arg Thr Glu Lys Asp Ser Lys Ile Tyr
    50                  55                  60

Ser Ile Gly Ile Asn Ile Asp Asp Ser Leu Glu Val Arg Glu Leu Asn
65                  70                  75                  80

Leu Glu Thr Gln Gly Pro Asn Lys Lys Leu Lys Val Tyr Arg Asn Leu
                85                  90                  95
```

```
Phe Tyr Cys Asp Gly Phe Leu Leu Cys Pro Ala Leu Leu Asp Glu Val
                100                 105                 110

Ala Val Trp Asn Pro Trp Leu Arg Lys Gln Thr Lys Trp Ile Glu Pro
            115                 120                 125

Lys Arg Ser Arg Phe Asn Leu Tyr Gly Leu Gly Tyr Asp Asn Arg Arg
        130                 135                 140

Pro Glu Lys Cys Tyr Lys Ile Leu Gly Phe Gly Tyr Gly Tyr Ser Ser
145                 150                 155                 160

Glu Ile Asn Gly Ser Tyr Asn Arg Ile Asn Pro Arg Val Ser Val Phe
                165                 170                 175

Glu Phe Glu Thr Asn Ala Trp Lys Asp Leu Lys Phe Gly Leu Phe Asp
            180                 185                 190

Trp His Leu Arg Ser Pro Arg Thr Val Leu Ser Leu Asn Gly Thr Leu
        195                 200                 205

Tyr Trp Ile Ala Val Arg Cys Glu Ser Gly Gly Asp Gly Phe Ile Gln
210                 215                 220

Ser Phe Asp Phe Ser Arg Glu Met Phe Glu Pro Phe Cys Leu Leu Pro
225                 230                 235                 240

Cys Lys Asn Asp Phe Gly Asp Thr Gln Ile Leu Glu Val Phe Arg Gly
                245                 250                 255

Asp Arg Leu Ser Val Leu Glu Gln Cys Pro Thr Thr Asn Lys Ile Lys
            260                 265                 270

Ile Trp Val Thr Lys Asn Lys Ile Ser Gly Asp Arg Lys Glu Leu Val
        275                 280                 285

Ser Trp Arg Leu Leu Met Thr Val Ser Ile Pro Asn Phe Pro Arg Leu
290                 295                 300

Gln Asp Leu Tyr Ser Asn Ser Gln Pro Ser Tyr Phe Met Asp Asn Asn
305                 310                 315                 320

Asp Asp Lys Arg Leu Ile Val Cys Thr Cys Asp Glu Ser Gly Lys Pro
                325                 330                 335

Cys Ile Tyr Ile Val Lys Gly Asp Arg Phe Lys Lys Ile Gln Met Gly
            340                 345                 350

Phe Glu Val Glu Pro Trp Pro Phe His Leu Val Tyr Val Pro Ser Leu
        355                 360                 365

Val Pro Ile Pro Leu Ala
    370

<210> SEQ ID NO 75
<211> LENGTH: 1917
<212> TYPE: DNA
<213> ORGANISM: Arabidopsis thaliana

<400> SEQUENCE: 75
atggatgata caatggacat gagttcaggt agtgatgaag aagtacaaga agagaagacc      60
actgttaacg agagggtcat ctatcaggct gcattacaag atctgaagca acccaagacc     120
gaaaaggatc tacctcctgg tgttcttaca gttcctctta tgaggcatca gaaaattgca     180
ttgaactgga tgcgtaagaa agaaaaaaga agcaggcact gtttgggagg atattagca     240 gatgatcagg gacttggtaa aacgatctcg acgatctctc ttatcctgtt acaaaagttg     300
aagtcacaat caaagcagag aaagcgaaaa ggtcaaaact ctggtggtac attgattgtt     360
tgtccagcaa gtgttgtaaa acaatgggca agagaagtta agagaaggt ttctgatgaa      420 cacaaactct ctgttttagt ccaccatgga tctcacagaa ccaagatcc aacagaaata     480 gcaatatatg atgtggtcat gacaacttac gccattgtta caaatgaagt tccacaaaac     540
```

```
cctatgctga atcgttatga tagtatgaga ggcagagaaa gccttgacgg atcgagtttg    600
attcagcctc acgttggtgc actaggaaga gttaggtggt tgagagtagt attagatgaa    660
gctcatacaa ttaaaaacca tagaacccta attgcaaaag cttgttttag ccttagagcc    720
aaaaggagat ggtgtttgac tggaacgccg ataaagaaca aagtagacga tctttatagc    780
tatttcagat ttcttagata tcatccatat gccatgtgca attcatttca ccaaagaatc    840
aaagctccaa ttgataaaaa gcctcttcat ggttacaaga agcttcaagc tattctaagg    900
ggtataatgt tgcgccgcac caaagaatgg tcttttctaca ggaagcttga attgaattca    960
cgttggaagt tgaggaata tgctgctgat gggactttgc atgaacacat ggcttatctt    1020
ttggtgatgc ttttgcgact acgccaagct tgtaaccatc cacaacttgt taacggatat    1080
agtcactcag atactacaag aaaaatgtca gatggagttc gagtagcccc tagagagaat    1140
ctaatcatgt tcctcgatct cttgaaatta tcctcaacca cctgctctgt ttgtagtgat    1200
ccaccaaaag accctgttgt tactttgtgt ggccatgtgt tttgttatga gtgtgtgtct    1260
gtaaacatta acggggataa caatacgtgc cctgcactta attgccacag ccagcttaaa    1320
catgatgttg ttttcactga atctgcagtt agaagttgca tcaacgatta tgatgatcct    1380
gaagataaaa atgctttagt tgcatcaagg cgagtttatt tcatcgaaaa tccgagctgt    1440
gatagagatt cttcagtcgc ttgcagagca aggcagtcca gacactccac caataaagac    1500
aatagtatca gtggactggt atgtgcgatg ttgatgtctc ttaaagctgg aaaccttgga    1560
ttgaatatgg tagctgcaag tcatgtcatt ctactggacc tatggtggaa tccaacaaca    1620
gaggatcaag ctattgatcg agctcatcgt atcggacaaa ctcgagctgt tacggtcact    1680
cgtattgcca tcaaaaatac cgttgaggaa cgaattttga ctcttcatga acgtaaaagg    1740
aacattgttg catctgcatt gggtgaaaaa aactggcaaa gttctgcga ttcaactaac    1800
actagaagat ctcgaatatc tgttttttgg tgtgtagaat atcccagagt ttttattgat    1860
aagaggaata aaaccttag ctatttaata agtcacaagt gtgaatgtaa tgaataa       1917
```

<210> SEQ ID NO 76
<211> LENGTH: 638
<212> TYPE: PRT
<213> ORGANISM: Arabidopsis thaliana

<400> SEQUENCE: 76

```
Met Asp Asp Thr Met Asp Met Ser Ser Gly Ser Asp Glu Glu Val Gln
 1               5                  10                  15

Glu Glu Lys Thr Thr Val Asn Glu Arg Val Ile Tyr Gln Ala Ala Leu
            20                  25                  30

Gln Asp Leu Lys Gln Pro Lys Thr Glu Lys Asp Leu Pro Pro Gly Val
        35                  40                  45

Leu Thr Val Pro Leu Met Arg His Gln Lys Ile Ala Leu Asn Trp Met
    50                  55                  60

Arg Lys Lys Glu Lys Arg Ser Arg His Cys Leu Gly Gly Ile Leu Ala
65                  70                  75                  80

Asp Asp Gln Gly Leu Gly Lys Thr Ile Ser Thr Ile Ser Leu Ile Leu
                85                  90                  95

Leu Gln Lys Leu Lys Ser Gln Ser Lys Gln Arg Lys Arg Lys Gly Gln
            100                 105                 110

Asn Ser Gly Gly Thr Leu Ile Val Cys Pro Ala Ser Val Val Lys Gln
        115                 120                 125

Trp Ala Arg Glu Val Lys Glu Lys Val Ser Asp Glu His Lys Leu Ser
    130                 135                 140
```

-continued

```
Val Leu Val His His Gly Ser His Arg Thr Lys Asp Pro Thr Glu Ile
145                 150                 155                 160

Ala Ile Tyr Asp Val Val Met Thr Thr Tyr Ala Ile Val Thr Asn Glu
                165                 170                 175

Val Pro Gln Asn Pro Met Leu Asn Arg Tyr Asp Ser Met Arg Gly Arg
            180                 185                 190

Glu Ser Leu Asp Gly Ser Ser Leu Ile Gln Pro His Val Gly Ala Leu
        195                 200                 205

Gly Arg Val Arg Trp Leu Arg Val Val Leu Asp Glu Ala His Thr Ile
    210                 215                 220

Lys Asn His Arg Thr Leu Ile Ala Lys Ala Cys Phe Ser Leu Arg Ala
225                 230                 235                 240

Lys Arg Arg Trp Cys Leu Thr Gly Thr Pro Ile Lys Asn Lys Val Asp
                245                 250                 255

Asp Leu Tyr Ser Tyr Phe Arg Phe Leu Arg Tyr His Pro Tyr Ala Met
            260                 265                 270

Cys Asn Ser Phe His Gln Arg Ile Lys Ala Pro Ile Asp Lys Lys Pro
        275                 280                 285

Leu His Gly Tyr Lys Lys Leu Gln Ala Ile Leu Arg Gly Ile Met Leu
    290                 295                 300

Arg Arg Thr Lys Glu Trp Ser Phe Tyr Arg Lys Leu Glu Leu Asn Ser
305                 310                 315                 320

Arg Trp Lys Phe Glu Glu Tyr Ala Ala Asp Gly Thr Leu His Glu His
                325                 330                 335

Met Ala Tyr Leu Leu Val Met Leu Leu Arg Leu Arg Gln Ala Cys Asn
            340                 345                 350

His Pro Gln Leu Val Asn Gly Tyr Ser His Ser Asp Thr Thr Arg Lys
        355                 360                 365

Met Ser Asp Gly Val Arg Val Ala Pro Arg Glu Asn Leu Ile Met Phe
    370                 375                 380

Leu Asp Leu Leu Lys Leu Ser Ser Thr Thr Cys Ser Val Cys Ser Asp
385                 390                 395                 400

Pro Pro Lys Asp Pro Val Val Thr Leu Cys Gly His Val Phe Cys Tyr
                405                 410                 415

Glu Cys Val Ser Val Asn Ile Asn Gly Asp Asn Asn Thr Cys Pro Ala
            420                 425                 430

Leu Asn Cys His Ser Gln Leu Lys His Asp Val Val Phe Thr Glu Ser
        435                 440                 445

Ala Val Arg Ser Cys Ile Asn Asp Tyr Asp Asp Pro Glu Asp Lys Asn
    450                 455                 460

Ala Leu Val Ala Ser Arg Arg Val Tyr Phe Ile Glu Asn Pro Ser Cys
465                 470                 475                 480

Asp Arg Asp Ser Ser Val Ala Cys Arg Ala Arg Gln Ser Arg His Ser
                485                 490                 495

Thr Asn Lys Asp Asn Ser Ile Ser Gly Leu Val Cys Ala Met Leu Met
            500                 505                 510

Ser Leu Lys Ala Gly Asn Leu Gly Leu Asn Met Val Ala Ala Ser His
        515                 520                 525

Val Ile Leu Leu Asp Leu Trp Trp Asn Pro Thr Thr Glu Asp Gln Ala
    530                 535                 540

Ile Asp Arg Ala His Arg Ile Gly Gln Thr Arg Ala Val Thr Val Thr
545                 550                 555                 560

Arg Ile Ala Ile Lys Asn Thr Val Glu Glu Arg Ile Leu Thr Leu His
```

```
                        565                 570                 575
Glu Arg Lys Arg Asn Ile Val Ala Ser Ala Leu Gly Glu Lys Asn Trp
                580                 585                 590

Gln Lys Phe Cys Asp Ser Thr Asn Thr Arg Arg Ser Arg Ile Ser Val
            595                 600                 605

Phe Trp Cys Val Glu Tyr Pro Arg Val Phe Ile Asp Lys Arg Asn Lys
    610                 615                 620

Thr Phe Ser Tyr Leu Ile Ser His Lys Cys Glu Cys Asn Glu
625                 630                 635

<210> SEQ ID NO 77
<211> LENGTH: 1965
<212> TYPE: DNA
<213> ORGANISM: Arabidopsis thaliana

<400> SEQUENCE: 77
atgtttctaa gtcttcttga aacctgtatt cgctcaagga atctggtctt aggtcaggtc      60
attcatcagc atcttcttaa acgctctctt acgttaagtt cctctacagt gctcgtcaat     120
ttaacacgtc tttacgcatc atgcaatgaa gtggaacttg cacgccatgt gttcgatgaa     180
attcctcatc caaggatcaa tcctattgct tgggatttga tgatcagagc ctatgcttcg     240
aatgatttcg cggaaaaagc tttggatttg tactacaaga tgctgaattc tggtgttaga     300
cccacgaaat atacgtaccc gtttgttttg aaagcatgtg ctggtcttcg agcaattgac     360
gatggtaagc tgatacatag tcatgtgaat tgtagcgact tgcaactgat atgtatgta     420 tgtactgctc tggttgattt ctatgctaag tgtggggaac ttgagatggc tataaaggtg     480
ttcgacgaaa tgcctaagag agatatggtt gcttggaatg ctatgatttc tgggttttct     540
ttacattgct gtttaactga tgtcattgga ttgttttggg atatgcgtag aatcgatggt     600
ctgagtccta atctatccac catcgttggg atgtttcctg cactaggaag ggctggtgca     660
ttgagggaag ggaaagctgt tcatgggtat tgcacaagaa tgggttttag caatgattta     720
gttgttaaga ctgggatctt ggatgtatat gccaagagca agtgcattat ctatgcgaga     780
agagttttcg atttagactt taagaagaat gaggtaacct ggagtgctat gattggaggc     840
tacgtagaaa acgaaatgat aaaggaagct ggagaagtgt ttttcagat gttggttaat     900 gataatgtgg caatggtgac gccagttgcc attgggctta ttctgatggg ttgtgcaagg     960
tttggagatc taagtggagg gcgatgtgta cattgttacg cggttaaagc aggcttcatc    1020
ttagacttaa ctgttcaaaa caccataatt tcattttatg ctaagtatgg aagcttatgt    1080
gatgctttta ggcagtttag tgagattggc ttgaaagatg ttatttcata taattctctc    1140
atcactgggt gtgtagtgaa ctgtcgccca gaagagagtt tcgtctatt tcatgagatg    1200 agaacatctg gaattcgtcc tgatattaca acattgcttg gtgtcttaac cgcttgctct    1260
cacttggctg ctttgggaca cggttctagt tgccacgggt attgtgttgt tcatggctat    1320
gcagttaaca caagcatttg taatgcactg atggatatgt acacaaagtg tggaaaactt    1380
gatgtagcca agagttttt cgacacaatg cataagcggg atatagtttc gtggaacaca    1440
atgctgttcg gattcggaat tcatggtctt ggcaaagaag ctctttctct gttcaacagt    1500
atgcaggaaa caggtgtgaa cccagacgag gtgactcttc ttgctatttt gtctgcttgt    1560
agccattcag gactagtgga tgaagggaaa caactgttca actccatgtc tcgaggagat    1620
ttcaacgtca tcccaagaat agaccattac aattgcatga ctgatcttct agcccgtgcc    1680
ggatacttgg atgaagctta tgattttgta aacaagatgc catttgagcc cgatattcgc    1740
```

```
gtgttgggta cacttctctc tgcttgttgg acgtacaaga atgcggaact tgggaatgaa    1800
gtgtcgaaaa agatgcagag tcttggtgaa acaacagaaa gcttagttct tctatccaac    1860
acctactcag ctgctgagag atgggaagat gcagctagaa ttagaatgat acagaagaaa    1920
agagggcttc tcaagactcc gggttatagc tgggtcgatg tttga                    1965
```

<210> SEQ ID NO 78
<211> LENGTH: 654
<212> TYPE: PRT
<213> ORGANISM: Arabidopsis thaliana

<400> SEQUENCE: 78

```
Met Phe Leu Ser Leu Leu Glu Thr Cys Ile Arg Ser Arg Asn Leu Val
1               5                   10                  15

Leu Gly Gln Val Ile His Gln His Leu Leu Lys Arg Ser Leu Thr Leu
            20                  25                  30

Ser Ser Ser Thr Val Leu Val Asn Leu Thr Arg Leu Tyr Ala Ser Cys
        35                  40                  45

Asn Glu Val Glu Leu Ala Arg His Val Phe Asp Glu Ile Pro His Pro
    50                  55                  60

Arg Ile Asn Pro Ile Ala Trp Asp Leu Met Ile Arg Ala Tyr Ala Ser
65                  70                  75                  80

Asn Asp Phe Ala Glu Lys Ala Leu Asp Leu Tyr Tyr Lys Met Leu Asn
                85                  90                  95

Ser Gly Val Arg Pro Thr Lys Tyr Thr Tyr Pro Phe Val Leu Lys Ala
            100                 105                 110

Cys Ala Gly Leu Arg Ala Ile Asp Asp Gly Lys Leu Ile His Ser His
        115                 120                 125

Val Asn Cys Ser Asp Phe Ala Thr Asp Met Tyr Val Cys Thr Ala Leu
    130                 135                 140

Val Asp Phe Tyr Ala Lys Cys Gly Glu Leu Glu Met Ala Ile Lys Val
145                 150                 155                 160

Phe Asp Glu Met Pro Lys Arg Asp Met Val Ala Trp Asn Ala Met Ile
                165                 170                 175

Ser Gly Phe Ser Leu His Cys Cys Leu Thr Asp Val Ile Gly Leu Phe
            180                 185                 190

Leu Asp Met Arg Arg Ile Asp Gly Leu Ser Pro Asn Leu Ser Thr Ile
        195                 200                 205

Val Gly Met Phe Pro Ala Leu Gly Arg Ala Gly Ala Leu Arg Glu Gly
    210                 215                 220

Lys Ala Val His Gly Tyr Cys Thr Arg Met Gly Phe Ser Asn Asp Leu
225                 230                 235                 240

Val Val Lys Thr Gly Ile Leu Asp Val Tyr Ala Lys Ser Lys Cys Ile
                245                 250                 255

Ile Tyr Ala Arg Arg Val Phe Asp Leu Asp Phe Lys Lys Asn Glu Val
            260                 265                 270

Thr Trp Ser Ala Met Ile Gly Gly Tyr Val Glu Asn Glu Met Ile Lys
        275                 280                 285

Glu Ala Gly Glu Val Phe Phe Gln Met Leu Val Asn Asp Asn Val Ala
    290                 295                 300

Met Val Thr Pro Val Ala Ile Gly Leu Ile Leu Met Gly Cys Ala Arg
305                 310                 315                 320

Phe Gly Asp Leu Ser Gly Gly Arg Cys Val His Cys Tyr Ala Val Lys
                325                 330                 335

Ala Gly Phe Ile Leu Asp Leu Thr Val Gln Asn Thr Ile Ile Ser Phe
```

```
              340            345            350
Tyr Ala Lys Tyr Gly Ser Leu Cys Asp Ala Phe Arg Gln Phe Ser Glu
            355            360            365
Ile Gly Leu Lys Asp Val Ile Ser Tyr Asn Ser Leu Ile Thr Gly Cys
        370            375            380
Val Val Asn Cys Arg Pro Glu Glu Ser Phe Arg Leu Phe His Glu Met
385            390            395            400
Arg Thr Ser Gly Ile Arg Pro Asp Ile Thr Thr Leu Leu Gly Val Leu
                405            410            415
Thr Ala Cys Ser His Leu Ala Ala Leu Gly His Gly Ser Ser Cys His
            420            425            430
Gly Tyr Cys Val Val His Gly Tyr Ala Val Asn Thr Ser Ile Cys Asn
            435            440            445
Ala Leu Met Asp Met Tyr Thr Lys Cys Gly Lys Leu Asp Val Ala Lys
        450            455            460
Arg Val Phe Asp Thr Met His Lys Arg Asp Ile Val Ser Trp Asn Thr
465            470            475            480
Met Leu Phe Gly Phe Gly Ile His Gly Leu Gly Lys Glu Ala Leu Ser
                485            490            495
Leu Phe Asn Ser Met Gln Glu Thr Gly Val Asn Pro Asp Glu Val Thr
            500            505            510
Leu Leu Ala Ile Leu Ser Ala Cys Ser His Ser Gly Leu Val Asp Glu
            515            520            525
Gly Lys Gln Leu Phe Asn Ser Met Ser Arg Gly Asp Phe Asn Val Ile
        530            535            540
Pro Arg Ile Asp His Tyr Asn Cys Met Thr Leu Leu Ala Arg Ala
545            550            555            560
Gly Tyr Leu Asp Glu Ala Tyr Asp Phe Val Asn Lys Met Pro Phe Glu
                565            570            575
Pro Asp Ile Arg Val Leu Gly Thr Leu Leu Ser Ala Cys Trp Thr Tyr
            580            585            590
Lys Asn Ala Glu Leu Gly Asn Glu Val Ser Lys Lys Met Gln Ser Leu
            595            600            605
Gly Glu Thr Thr Glu Ser Leu Val Leu Leu Ser Asn Thr Tyr Ser Ala
        610            615            620
Ala Glu Arg Trp Glu Asp Ala Ala Arg Ile Arg Met Ile Gln Lys Lys
625            630            635            640
Arg Gly Leu Leu Lys Thr Pro Gly Tyr Ser Trp Val Asp Val
                645            650

<210> SEQ ID NO 79
<211> LENGTH: 3321
<212> TYPE: DNA
<213> ORGANISM: Arabidopsis thaliana

<400> SEQUENCE: 79
agacttttgc cttctctaac cagtgtttcg tgattttggg tgatcctaga aatgggagat    60
ggggctgaga ttgtaaccag gttatatggg gatgagaaga agcttgcaga ggatggtaga   120
attagtgagt tggtgggatc tgatgaagtg aaggataatg aagaagaggt ctttgaggaa   180
gcaattggtt cgcaggaggg tctaaaacct gaatctctca aaaccgatgt gttgcaagag   240
gattttcctt tagcttccaa tgatgaagtg tgtgatttgg aagaaacaag tagaaatgag   300
agaggagtag aaaatttaaa ggttaattat tcgagagattg gagagagcca tggtgaggtt   360
aacgagcaat gtataactac gaaagaggct gattctgatt tggtgactct caaaatgaat   420
```

```
gattatgatc acggggaagt agcagatgca gatatttctt atggtaaaat ggcatcaagc      480
ttggatgtgg ttgagaacag tgagaaagct acttccaatt tagctactga ggatgtgaat      540
ttggaaaacg gaaatacaca ttcttcttca gaaaatggag tagtctctcc tgatgagaat      600
aaagaactgg tggcggaagt tatctcagta agtgcctgtt ccgtggaaac agggagtaat      660
ggtattgacg acgaaaaatg ggaggaagaa attgatgtat cagctggcat ggtaacagaa      720
caaagaaatg gtaagactgg tgctgagttc aatagtgtta aaattgtttc aggtgacaaa      780
tccttgaatg atagtattga agtagcagct gggaccttat ctccattgga aaaatctagt      840
tcggaggaga agggagagac tgaaagtcaa aacagtaatg gaggacatga tattcaatct      900
aataaggaaa ttgtaaagca gcaagatagc agtgtaaata taggtccaga gattaaggaa      960
agccaacata tggaaagaga atctgaggta ttaagttctg tttcaccaac agagtctaga     1020
agtgatactg cagcattacc acctgctcgc ccagcaggtc ttggtcgtgc tgctccactt     1080
ttggaacctg caccacgcgt tacacaacag cctcgtgtca atggaaatgt gtctcacaat     1140
cagcctcagc aagctgaaga ctctaccact gcagagacag atgagcatga tgagacccgt     1200
gagaagctcc agtttatcag ggtcaaattt ttgaggcttt cacatagatt agggcaaact     1260
ccacataatg ttgttgttgc tcaggttttg tacaggcttg gattggctga acagttgagg     1320
ggcagaaacg gaagccgtgt tggtgccttt agttttgatc gtgccagtgc catggcagaa     1380
cagcttgagg cagctgcaca gatcccctt gattttcctt gtacgattat ggtgcttggt     1440
aaaagtgggg ttggtaaaag tgcaaccatc aattctattt ttgatgaact gaaaattagt     1500
actgatgcat tccaggtggg gacaaagaag gttcaggata ttgagggttt tgttcaggga     1560
attaaggtac gggtaattga cactcccggt ctcttaccat cctggtcaga tcaacacaag     1620
aatgagaaga tcctgaagtc tgttagggca ttcatcaaga aaagtccgcc tgacattgtg     1680
ttatatcttg ataggttgga tatgcaaagc agagattctg gtgacatgcc tctcttacgc     1740
accatcactg atgttttgg accatcaata tggtttaatg ccattgtggg tttgactcat     1800
gccgcttcgg ctccaccaga tggcccaaat ggtactgctt ctagctatga catgtttgtg     1860
acacaacgtt ctcatgtcat ccagcaggcc attcgccaag cagcgggaga tatgaggctc     1920
atgaaccctg tttctttagt tgagaaccac tctgcttgca ggacaaatcg ggcaggccag     1980
agagtattac ctaatggcca agtgtggaag cctcatttgt tattactctc atttgcatcc     2040
aagattcttg ccgaagcaaa tgctcttctg aaattacaag ataatattcc aggggggacaa     2100 tttgcaactc ggtccaaggc tccgccacta ccattgctcc tctcatcgct tctgcaatca     2160
agaccacaag ctaagcttcc tgagcaacag tacgatgatg aagacgatga agatgattta     2220
gacgaatcat cagattctga ggaagaatca gagtatgatg agcttcctcc ctttaagcgg     2280
ttgactaaag cagagatgac taagcttagc aaatctcaga gaaggaata tctcgatgag     2340 atggagtatc gggagaaact atttatgaag agacagatga agaggaaag aaagagacgt     2400 aagttgttga agaaatttgc tgctgagatt aaagatatgc taacgggta tagtgaaaat     2460 gtggaagagg agagaagtga acctgcatct gttccagttc caatgccaga tttatctcta     2520
cctgcatctt ttgactctga caatcctact catcggtacc ggtaccttga tacctccaat     2580
caatggcttg ttaggccagt gctggaaact catgggtggg atcatgatat tggttatgaa     2640
ggtgtgaatg cggaacgact atttgttgtt aaagacaaaa taccagtatc tttctctggc     2700
caagtgacaa aggacaagaa ggatgcacat gtgcagctag aattggccag ctcggttaaa     2760
catggagaag gtagatcaac ttccctaggt tttgacatgc aaaatgctgg gaaggaatta     2820
```

-continued

```
gcgtacacta ttcgaagtga aacaagattt aacaagttta ggaaaaacaa agcagcagct    2880
ggtctctctg ttacgctctt aggtgattca gtttccgcgg gactaaaagt cgaagataag    2940
ttgattgcta ataaacggtt caggatggtt atgtcaggtg gagcaatgac tagtcgtgga    3000
gatgttgctt atggtggtac tttagaagct cagtttcgag ataaagatta ccgcttggt     3060 cggttttat caactcttgg actctctgtg atggattggc atggcgatct tgctatcgga     3120
gggaatatac agtctcaagt acccattgga cgttcctcta atctcattgc tcgtgctaat    3180
ctgaataaca gaggagcagg gcaagtaagc atccgcgtaa acagtctga gcagcttcaa     3240 cttgctgtgg ttgcacttgt tcctctgttc aagaagcttc ttacttatta ttcccctgag    3300
caaatgcaat atggacactg a                                              3321
```

<210> SEQ ID NO 80
<211> LENGTH: 1089
<212> TYPE: PRT
<213> ORGANISM: Arabidopsis thaliana

<400> SEQUENCE: 80

```
Met Gly Asp Gly Ala Glu Ile Val Thr Arg Leu Tyr Gly Asp Glu Lys
1               5                   10                  15

Lys Leu Ala Glu Asp Gly Arg Ile Ser Glu Leu Val Gly Ser Asp Glu
            20                  25                  30

Val Lys Asp Asn Glu Glu Val Phe Glu Glu Ala Ile Gly Ser Gln
        35                  40                  45

Glu Gly Leu Lys Pro Glu Ser Leu Lys Thr Asp Val Leu Gln Glu Asp
    50                  55                  60

Phe Pro Leu Ala Ser Asn Asp Glu Val Cys Asp Leu Glu Glu Thr Ser
65                  70                  75                  80

Arg Asn Glu Arg Gly Val Glu Asn Leu Lys Val Asn Tyr Ser Glu Ile
                85                  90                  95

Gly Glu Ser His Gly Glu Val Asn Glu Gln Cys Ile Thr Thr Lys Glu
            100                 105                 110

Ala Asp Ser Asp Leu Val Thr Leu Lys Met Asn Asp Tyr Asp His Gly
        115                 120                 125

Glu Val Ala Asp Ala Asp Ile Ser Tyr Gly Lys Met Ala Ser Ser Leu
    130                 135                 140

Asp Val Val Glu Asn Ser Glu Lys Ala Thr Ser Asn Leu Ala Thr Glu
145                 150                 155                 160

Asp Val Asn Leu Glu Asn Gly Asn Thr His Ser Ser Glu Asn Gly
                165                 170                 175

Val Val Ser Pro Asp Glu Asn Lys Glu Leu Val Ala Glu Val Ile Ser
            180                 185                 190

Val Ser Ala Cys Ser Val Glu Thr Gly Ser Asn Gly Ile Asp Asp Glu
        195                 200                 205

Lys Trp Glu Glu Glu Ile Asp Val Ser Ala Gly Met Val Thr Glu Gln
    210                 215                 220

Arg Asn Gly Lys Thr Gly Ala Glu Phe Asn Ser Val Lys Ile Val Ser
225                 230                 235                 240

Gly Asp Lys Ser Leu Asn Asp Ser Ile Glu Val Ala Ala Gly Thr Leu
                245                 250                 255

Ser Pro Leu Glu Lys Ser Ser Ser Glu Glu Lys Gly Glu Thr Glu Ser
            260                 265                 270

Gln Asn Ser Asn Gly Gly His Asp Ile Gln Ser Asn Lys Glu Ile Val
        275                 280                 285
```

```
Lys Gln Gln Asp Ser Ser Val Asn Ile Gly Pro Glu Ile Lys Glu Ser
    290                 295                 300

Gln His Met Glu Arg Glu Ser Glu Val Leu Ser Ser Val Ser Pro Thr
305                 310                 315                 320

Glu Ser Arg Ser Asp Thr Ala Ala Leu Pro Pro Ala Arg Pro Ala Gly
                325                 330                 335

Leu Gly Arg Ala Ala Pro Leu Leu Glu Pro Ala Pro Val Thr Gln
            340                 345                 350

Gln Pro Arg Val Asn Gly Asn Val Ser His Asn Gln Pro Gln Gln Ala
                355                 360                 365

Glu Asp Ser Thr Thr Ala Glu Thr Asp Glu His Asp Glu Thr Arg Glu
370                 375                 380

Lys Leu Gln Phe Ile Arg Val Lys Phe Leu Arg Leu Ser His Arg Leu
385                 390                 395                 400

Gly Gln Thr Pro His Asn Val Val Val Ala Gln Val Leu Tyr Arg Leu
                405                 410                 415

Gly Leu Ala Glu Gln Leu Arg Gly Arg Asn Gly Ser Arg Val Gly Ala
            420                 425                 430

Phe Ser Phe Asp Arg Ala Ser Ala Met Ala Glu Gln Leu Glu Ala Ala
        435                 440                 445

Ala Gln Asp Pro Leu Asp Phe Ser Cys Thr Ile Met Val Leu Gly Lys
    450                 455                 460

Ser Gly Val Gly Lys Ser Ala Thr Ile Asn Ser Ile Phe Asp Glu Leu
465                 470                 475                 480

Lys Ile Ser Thr Asp Ala Phe Gln Val Gly Thr Lys Lys Val Gln Asp
                485                 490                 495

Ile Glu Gly Phe Val Gln Gly Ile Lys Val Arg Val Ile Asp Thr Pro
            500                 505                 510

Gly Leu Leu Pro Ser Trp Ser Asp Gln His Lys Asn Glu Lys Ile Leu
        515                 520                 525

Lys Ser Val Arg Ala Phe Ile Lys Lys Ser Pro Pro Asp Ile Val Leu
    530                 535                 540

Tyr Leu Asp Arg Leu Asp Met Gln Ser Arg Asp Ser Gly Asp Met Pro
545                 550                 555                 560

Leu Leu Arg Thr Ile Thr Asp Val Phe Gly Pro Ser Ile Trp Phe Asn
                565                 570                 575

Ala Ile Val Gly Leu Thr His Ala Ala Ser Ala Pro Pro Asp Gly Pro
            580                 585                 590

Asn Gly Thr Ala Ser Ser Tyr Asp Met Phe Val Thr Gln Arg Ser His
        595                 600                 605

Val Ile Gln Gln Ala Ile Arg Gln Ala Ala Gly Asp Met Arg Leu Met
    610                 615                 620

Asn Pro Val Ser Leu Val Glu Asn His Ser Ala Cys Arg Thr Asn Arg
625                 630                 635                 640

Ala Gly Gln Arg Val Leu Pro Asn Gly Gln Val Trp Lys Pro His Leu
                645                 650                 655

Leu Leu Leu Ser Phe Ala Ser Lys Ile Leu Ala Glu Ala Asn Ala Leu
            660                 665                 670

Leu Lys Leu Gln Asp Asn Ile Pro Gly Gly Gln Phe Ala Thr Arg Ser
        675                 680                 685

Lys Ala Pro Pro Leu Pro Leu Leu Ser Ser Leu Leu Gln Ser Arg
    690                 695                 700

Pro Gln Ala Lys Leu Pro Glu Gln Gln Tyr Asp Asp Glu Asp Asp Glu
```

```
                705                 710                 715                 720
Asp Asp Leu Asp Glu Ser Ser Asp Ser Glu Glu Glu Ser Glu Tyr Asp
                    725                 730                 735

Glu Leu Pro Pro Phe Lys Arg Leu Thr Lys Ala Glu Met Thr Lys Leu
                    740                 745                 750

Ser Lys Ser Gln Lys Lys Glu Tyr Leu Asp Glu Met Glu Tyr Arg Glu
                    755                 760                 765

Lys Leu Phe Met Lys Arg Gln Met Lys Glu Glu Arg Lys Arg Arg Lys
                    770                 775                 780

Leu Leu Lys Lys Phe Ala Ala Glu Ile Lys Asp Met Pro Asn Gly Tyr
785                 790                 795                 800

Ser Glu Asn Val Glu Glu Arg Ser Glu Pro Ala Ser Val Pro Val
                    805                 810                 815

Pro Met Pro Asp Leu Ser Leu Pro Ala Ser Phe Asp Ser Asp Asn Pro
                    820                 825                 830

Thr His Arg Tyr Arg Tyr Leu Asp Thr Ser Asn Gln Trp Leu Val Arg
                    835                 840                 845

Pro Val Leu Glu Thr His Gly Trp Asp His Asp Ile Gly Tyr Glu Gly
850                 855                 860

Val Asn Ala Glu Arg Leu Phe Val Val Lys Asp Lys Ile Pro Val Ser
865                 870                 875                 880

Phe Ser Gly Gln Val Thr Lys Asp Lys Lys Asp Ala His Val Gln Leu
                    885                 890                 895

Glu Leu Ala Ser Ser Val Lys His Gly Glu Gly Arg Ser Thr Ser Leu
                    900                 905                 910

Gly Phe Asp Met Gln Asn Ala Gly Lys Glu Leu Ala Tyr Thr Ile Arg
                    915                 920                 925

Ser Glu Thr Arg Phe Asn Lys Phe Arg Lys Asn Lys Ala Ala Ala Gly
                    930                 935                 940

Leu Ser Val Thr Leu Leu Gly Asp Ser Val Ser Ala Gly Leu Lys Val
945                 950                 955                 960

Glu Asp Lys Leu Ile Ala Asn Lys Arg Phe Arg Met Val Met Ser Gly
                    965                 970                 975

Gly Ala Met Thr Ser Arg Gly Asp Val Ala Tyr Gly Gly Thr Leu Glu
                    980                 985                 990

Ala Gln Phe Arg Asp Lys Asp Tyr Pro Leu Gly Arg Phe Leu Ser Thr
                    995                 1000                1005

Leu Gly Leu Ser Val Met Asp Trp His Gly Asp Leu Ala Ile Gly
    1010                1015                1020

Gly Asn Ile Gln Ser Gln Val Pro Ile Gly Arg Ser Ser Asn Leu
    1025                1030                1035

Ile Ala Arg Ala Asn Leu Asn Asn Arg Gly Ala Gly Gln Val Ser
    1040                1045                1050

Ile Arg Val Asn Ser Ser Glu Gln Leu Gln Leu Ala Val Val Ala
    1055                1060                1065

Leu Val Pro Leu Phe Lys Lys Leu Leu Thr Tyr Tyr Ser Pro Glu
    1070                1075                1080

Gln Met Gln Tyr Gly His
    1085
```

<210> SEQ ID NO 81
<211> LENGTH: 1191
<212> TYPE: DNA
<213> ORGANISM: Arabidopsis thaliana

<400> SEQUENCE: 81

```
atgagctaca ctttctttct cctttgctc tctcttgtcc actccacttt ctcttcatta      60
gctcctacgg atcgagccgc gctccaatcc atcagagact ctttaaccga catgcccggt     120
tcagccttct tctcctcttg ggacttcaca gttcctgacc cttgttcctc cttctctggc     180
cttacctgct cttctcgcgg ccgtgtcacc ggcttaactc ttggccctaa tctctcaggc     240
tctctctccc cttccatctc cattctaacc cacttaaccc aactcattct ctaccccggt     300
tcagtcaccg gtcctctccc tctcggttc gattccctcc ctctccttcg agtcatttcc      360
ttaacaagaa accgtttaac cggtcctata cccgtatctt tctcatctct ctcaaatctc     420
cacactcttg accttagcta taaccaactc tctggctctc tccctccttt tctcaccact     480
cttcctcgac tcaaagtcct tgttttagcc tcaaaccatt tctccaacaa ccttaagcct     540
gtctctagcc cattgttcca tttagaccta aagatgaacc aaatctccgg ccaactccca     600
cccgctttcc cgactactct ccggtactta tctctatccg aaactcaat gcagggcaca      660
atcaatgcca tggagccatt aacagagcta atatacatcg atctaagcat gaaccaattt     720
accggcgcaa tccctagctc actctttagt cccacaatct caacaatgtt cctacaacga     780
aacaacttca catccattgc cacctcaaac gccacgtcat tgttacctga gggctccatt     840
gttgatctga gccataactc aatctccgga gagctaactc ccgcgcttgt cggagcagag     900
gctttgttct tgaacaacaa ccgtctcact ggagacattc agaggaata cgtcaagagc      960
ttaatcaacg gtacaacaaa acagctcttc ttgcaacata actacttcac gagattccct    1020
tggaactctg gtctccaact accagactct gtttcgctct gtttgtcata taactgtatg    1080
gagacagatc cagtcgttgg tttgtccacg tgtccgatcg aagttgcacc tctgctctca    1140
agacctgctt cacaatgttc aagattctat aatcacagct ccactggtta a             1191
```

<210> SEQ ID NO 82
<211> LENGTH: 396
<212> TYPE: PRT
<213> ORGANISM: Arabidopsis thaliana

<400> SEQUENCE: 82

```
Met Ser Tyr Thr Phe Phe Leu Leu Leu Ser Leu Val His Ser Thr
1               5                   10                  15

Phe Ser Ser Leu Ala Pro Thr Asp Arg Ala Ala Leu Gln Ser Ile Arg
                20                  25                  30

Asp Ser Leu Thr Asp Met Pro Gly Ser Ala Phe Phe Ser Ser Trp Asp
            35                  40                  45

Phe Thr Val Pro Asp Pro Cys Ser Ser Phe Ser Gly Leu Thr Cys Ser
        50                  55                  60

Ser Arg Gly Arg Val Thr Gly Leu Thr Leu Gly Pro Asn Leu Ser Gly
65                  70                  75                  80

Ser Leu Ser Pro Ser Ile Ser Ile Leu Thr His Leu Thr Gln Leu Ile
                85                  90                  95

Leu Tyr Pro Gly Ser Val Thr Gly Pro Leu Pro Pro Arg Phe Asp Ser
            100                 105                 110

Leu Pro Leu Leu Arg Val Ile Ser Leu Thr Arg Asn Arg Leu Thr Gly
        115                 120                 125

Pro Ile Pro Val Ser Phe Ser Ser Leu Ser Asn Leu His Thr Leu Asp
    130                 135                 140

Leu Ser Tyr Asn Gln Leu Ser Gly Ser Leu Pro Pro Phe Leu Thr Thr
145                 150                 155                 160
```

-continued

```
Leu Pro Arg Leu Lys Val Leu Val Leu Ala Ser Asn His Phe Ser Asn
                165                 170                 175
Asn Leu Lys Pro Val Ser Ser Pro Leu Phe His Leu Asp Leu Lys Met
            180                 185                 190
Asn Gln Ile Ser Gly Gln Leu Pro Pro Ala Phe Pro Thr Thr Leu Arg
        195                 200                 205
Tyr Leu Ser Leu Ser Gly Asn Ser Met Gln Gly Thr Ile Asn Ala Met
    210                 215                 220
Glu Pro Leu Thr Glu Leu Ile Tyr Ile Asp Leu Ser Met Asn Gln Phe
225                 230                 235                 240
Thr Gly Ala Ile Pro Ser Ser Leu Phe Ser Pro Thr Ile Ser Thr Met
                245                 250                 255
Phe Leu Gln Arg Asn Asn Phe Thr Ser Ile Ala Thr Ser Asn Ala Thr
            260                 265                 270
Ser Leu Leu Pro Glu Gly Ser Ile Val Asp Leu Ser His Asn Ser Ile
        275                 280                 285
Ser Gly Glu Leu Thr Pro Ala Leu Val Gly Ala Glu Ala Leu Phe Leu
    290                 295                 300
Asn Asn Asn Arg Leu Thr Gly Asp Ile Pro Glu Glu Tyr Val Lys Ser
305                 310                 315                 320
Leu Ile Asn Gly Thr Thr Lys Gln Leu Phe Leu Gln His Asn Tyr Phe
                325                 330                 335
Thr Arg Phe Pro Trp Asn Ser Gly Leu Gln Leu Pro Asp Ser Val Ser
            340                 345                 350
Leu Cys Leu Ser Tyr Asn Cys Met Glu Thr Asp Pro Val Val Gly Leu
        355                 360                 365
Ser Thr Cys Pro Ile Glu Val Ala Pro Leu Leu Ser Arg Pro Ala Ser
    370                 375                 380
Gln Cys Ser Arg Phe Tyr Asn His Ser Ser Thr Gly
385                 390                 395

<210> SEQ ID NO 83
<211> LENGTH: 2396
<212> TYPE: DNA
<213> ORGANISM: Arabidopsis thaliana

<400> SEQUENCE: 83
gagtccaagt tgactccttc gagctttgat tctcgttcca ataatacttc ctccaccatc      60
tctcctcctc tcgttagatc taagaaacag agaaacaag agagatagaa tgagaaaggg     120
agttctaaat cctgacagag atcgtcagat agtggaacat gagttgcagg aaactgggtt     180
tagtccagaa acagagaaag tcaagaacaa gaattttgaa gaagatgaag aggaagaaga     240
tgaatctgtg gagaagatat ttgagagtag agaagtacct tcttggaaga agcagttgac     300
ggtgagggct tttgtggtga gctttatgct aagcatcttg tttagtttca ttgttatgaa     360
gcttaacctc acaacgggaa tcatcccttc gctcaatgtc tctgctggtc ttttgggttt     420
cttctttgtc aagacatgga ctaagatgct ccataggtct ggtctcttga aacagccatt     480
tactcgccag gagaatactg ttattcagac ctgtgttgtt gcctcttctg gcattgcctt     540
cagcggaggt tttgggacat acctctttgg catgagtgaa cgaattgcga cccaatcagg     600
agatgtatcc cgtggcgtca aggacccttc tttgggttgg attatcggtt tcctctttgt     660
cgtcagcttt cttggcctct ctcagttgt cccctgcga agataatgg taatagactt     720 caaactaaca tacccaagtg gtactgcaac agctcatctt atcaacagct ttcacacccc     780
tcaaggcgcc aagctagcca agaaacaagt gagggtgttg gggaaatttt tctctttaag     840
```

```
cttcttctgg agtttcttcc aatggttctt taccggagga gaaaattgtg ggttctccaa    900
cttcccaaca tttggactca aagcttacca gtacaagttc tactttgatt tttcagcaac    960
atatgttggt gttggaatga tatgtccgta tataatcaac atctctgtcc tattgggagg   1020
aatcctctct tgggggataa tgtggcccct cattgaaacc aaaaagggag attggttccc   1080
tgataatgtc ccatccagca gcatgcatgg tctccaagct tacaaggtgt ttatagctgt   1140
tgctataatc ctaggagatg gcttatacaa cttttgcaag gtgctgagcc ggactctttc   1200
aggattattt gtacagctcc gaggccctac tacatctatt tcaagaacct ccttcacact   1260
tgaagaagac cctcatgctt ccccactaag cccaaagcaa tcttatgatg accaacgtcg   1320
tacaagattc ttcctcaaag accaaatccc tacttggttt gctgttggag gttatatcac   1380
aatagctgca acatctacag cgatactccc tcacatgttc caccagctga gatggtatta   1440
cattctggtc atctatatct gcgcgcctgt cttagctttc tgtaacgctt atggagctgg   1500
actcacagac tggtccttgg cttcaactta tggaaagtta gccatattca caattggagc   1560
ttgggctggc tctgagcacg gtggtatgct ggctggtcta gcagcatgtg gtgtcatgat   1620
gaacatagtc tcgacagctt cggatctaac acaagacttc aagacaggct acctcacttt   1680
atcatctcca aagtcaatgt ttgtgagcca agtgattgga acagcaatgg gttgtgtggt   1740
atctccttgc gtgttctggc tattctacaa agcgtttgat gatttaggcc tcccaaacac   1800
tgaatacccct gctccatttg ctactgtata tcgaagcatg gctaaactag gagtggaagg   1860
tgtcgcatct ctaccgagag aatgtcttgt tctatgctac gcgttcttcg gtgtggcgat   1920
tctcgtaaac atagtaaaag atagtctcca tagcaattgg ggaaggttca ttccacttcc   1980
catggcaatg gctataccgt tttttcttggg accttacttc gcaattgaca tgtgtgtggg   2040
aagtttgata cttttttatct gggaaagagt agatgcagcc aaggctgaag cttttgggac   2100
agcggtggct tctggtttga tatgcggaga tggcatttgg tctttgccga gctccgtgct   2160
cgctatagcc ggagttaatc ctcctgtttg catgaagttt ctctcttctg caaccaattc   2220
aaaggtcgac aacttcctga aaggatccat ttaaaactca ataagtaac aacatctcaa    2280
ccatgtgaaa gtgtaatgat gcttcaattg ttcttttacc attatgacga ttttgaatgt   2340
aactcgtata taaagatctt agatatgaaa gggctctgat tgatgattgt caaaac       2396
```

<210> SEQ ID NO 84
<211> LENGTH: 714
<212> TYPE: PRT
<213> ORGANISM: Arabidopsis thaliana

<400> SEQUENCE: 84

```
Met Arg Lys Gly Val Leu Asn Pro Asp Arg Asp Arg Gln Ile Val Glu
1               5                   10                  15

His Glu Leu Gln Glu Thr Gly Phe Ser Pro Glu Thr Glu Lys Val Lys
            20                  25                  30

Asn Lys Asn Phe Glu Glu Asp Glu Glu Glu Asp Glu Ser Val Glu
        35                  40                  45

Lys Ile Phe Glu Ser Arg Glu Val Pro Ser Trp Lys Lys Gln Leu Thr
    50                  55                  60

Val Arg Ala Phe Val Val Ser Phe Met Leu Ser Ile Leu Phe Ser Phe
65                  70                  75                  80

Ile Val Met Lys Leu Asn Leu Thr Thr Gly Ile Ile Pro Ser Leu Asn
                85                  90                  95

Val Ser Ala Gly Leu Leu Gly Phe Phe Phe Val Lys Thr Trp Thr Lys
```

```
                100             105             110
Met Leu His Arg Ser Gly Leu Leu Lys Gln Pro Phe Thr Arg Gln Glu
            115                 120                 125

Asn Thr Val Ile Gln Thr Cys Val Val Ala Ser Ser Gly Ile Ala Phe
            130                 135             140

Ser Gly Gly Phe Gly Thr Tyr Leu Phe Gly Met Ser Glu Arg Ile Ala
145                     150                 155                 160

Thr Gln Ser Gly Asp Val Ser Arg Gly Val Lys Asp Pro Ser Leu Gly
                165                 170                 175

Trp Ile Ile Gly Phe Leu Phe Val Ser Phe Leu Gly Leu Phe Ser
            180                 185                 190

Val Val Pro Leu Arg Lys Ile Met Val Ile Asp Phe Lys Leu Thr Tyr
            195                 200                 205

Pro Ser Gly Thr Ala Thr Ala His Leu Ile Asn Ser Phe His Thr Pro
            210                 215                 220

Gln Gly Ala Lys Leu Ala Lys Lys Gln Val Arg Val Leu Gly Lys Phe
225                 230                 235                 240

Phe Ser Leu Ser Phe Phe Trp Ser Phe Phe Gln Trp Phe Phe Thr Gly
                245                 250                 255

Gly Glu Asn Cys Gly Phe Ser Asn Phe Pro Thr Phe Gly Leu Lys Ala
                260                 265                 270

Tyr Gln Tyr Lys Phe Tyr Phe Asp Phe Ser Ala Thr Tyr Val Gly Val
            275                 280                 285

Gly Met Ile Cys Pro Tyr Ile Ile Asn Ile Ser Val Leu Leu Gly Gly
            290                 295                 300

Ile Leu Ser Trp Gly Ile Met Trp Pro Leu Ile Glu Thr Lys Lys Gly
305                 310                 315                 320

Asp Trp Phe Pro Asp Asn Val Pro Ser Ser Met His Gly Leu Gln
                325                 330                 335

Ala Tyr Lys Val Phe Ile Ala Val Ala Ile Ile Leu Gly Asp Gly Leu
                340                 345                 350

Tyr Asn Phe Cys Lys Val Leu Ser Arg Thr Leu Ser Gly Leu Phe Val
            355                 360                 365

Gln Leu Arg Gly Pro Thr Thr Ser Ile Ser Arg Thr Ser Phe Thr Leu
            370                 375                 380

Glu Glu Asp Pro His Ala Ser Pro Leu Ser Pro Lys Gln Ser Tyr Asp
385                 390                 395                 400

Asp Gln Arg Arg Thr Arg Phe Pro Leu Lys Asp Gln Ile Pro Thr Trp
                405                 410                 415

Phe Ala Val Gly Gly Tyr Ile Thr Ile Ala Ala Thr Ser Thr Ala Ile
                420                 425                 430

Leu Pro His Met Phe His Gln Leu Arg Trp Tyr Tyr Ile Leu Val Ile
            435                 440                 445

Tyr Ile Cys Ala Pro Val Leu Ala Phe Cys Asn Ala Tyr Gly Ala Gly
            450                 455                 460

Leu Thr Asp Trp Ser Leu Ala Ser Thr Tyr Gly Lys Leu Ala Ile Phe
465                 470                 475                 480

Thr Ile Gly Ala Trp Ala Gly Ser Glu His Gly Gly Met Leu Ala Gly
                485                 490                 495

Leu Ala Ala Cys Gly Val Met Met Asn Ile Val Ser Thr Ala Ser Asp
                500                 505                 510

Leu Thr Gln Asp Phe Lys Thr Gly Tyr Leu Thr Leu Ser Ser Pro Lys
            515                 520                 525
```

```
Ser Met Phe Val Ser Gln Val Ile Gly Thr Ala Met Gly Cys Val Val
    530                 535                 540

Ser Pro Cys Val Phe Trp Leu Phe Tyr Lys Ala Phe Asp Asp Leu Gly
545                 550                 555                 560

Leu Pro Asn Thr Glu Tyr Pro Ala Pro Phe Ala Thr Val Tyr Arg Ser
                565                 570                 575

Met Ala Lys Leu Gly Val Glu Gly Val Ala Ser Leu Pro Arg Glu Cys
            580                 585                 590

Leu Val Leu Cys Tyr Ala Phe Phe Gly Val Ala Ile Leu Val Asn Ile
        595                 600                 605

Val Lys Asp Ser Leu His Ser Asn Trp Gly Arg Phe Ile Pro Leu Pro
    610                 615                 620

Met Ala Met Ala Ile Pro Phe Phe Leu Gly Pro Tyr Phe Ala Ile Asp
625                 630                 635                 640

Met Cys Val Gly Ser Leu Ile Leu Phe Ile Trp Glu Arg Val Asp Ala
                645                 650                 655

Ala Lys Ala Glu Ala Phe Gly Thr Ala Val Ala Ser Gly Leu Ile Cys
            660                 665                 670

Gly Asp Gly Ile Trp Ser Leu Pro Ser Ser Val Leu Ala Ile Ala Gly
        675                 680                 685

Val Asn Pro Pro Val Cys Met Lys Phe Leu Ser Ser Ala Thr Asn Ser
    690                 695                 700

Lys Val Asp Asn Phe Leu Lys Gly Ser Ile
705                 710

<210> SEQ ID NO 85
<211> LENGTH: 354
<212> TYPE: DNA
<213> ORGANISM: Arabidopsis thaliana

<400> SEQUENCE: 85
atgaacagga aggcctctgt ttccaaggag ctcaacgcca agcattcaaa gatattggaa      60 gcactttttga agcatccaga caatcgagaa tgtgcagatt gtagatcaaa ggcaccaaga     120
tgggcaagtg tgaaccttgg gatattcatt tgtatgcaat gttctggaat ccatcgtagc     180
cttggcgtcc acatctctca ggtaaggtct ataactctgg atacatggct tccagatcag     240 gttgcttttca tgaaatctac cggtaatgct aagggaaatg agtattggga atcagaattg     300
cctcaacatt tcgagagaag ttcaagcgac acgtttataa gagccaagta ttga            354

<210> SEQ ID NO 86
<211> LENGTH: 117
<212> TYPE: PRT
<213> ORGANISM: Arabidopsis thaliana

<400> SEQUENCE: 86

Met Asn Arg Lys Ala Ser Val Ser Lys Glu Leu Asn Ala Lys His Ser
1               5                   10                  15

Lys Ile Leu Glu Ala Leu Leu Lys His Pro Asp Asn Arg Glu Cys Ala
            20                  25                  30

Asp Cys Arg Ser Lys Ala Pro Arg Trp Ala Ser Val Asn Leu Gly Ile
        35                  40                  45

Phe Ile Cys Met Gln Cys Ser Gly Ile His Arg Ser Leu Gly Val His
    50                  55                  60

Ile Ser Gln Val Arg Ser Ile Thr Leu Asp Thr Trp Leu Pro Asp Gln
65                  70                  75                  80

Val Ala Phe Met Lys Ser Thr Gly Asn Ala Lys Gly Asn Glu Tyr Trp
```

```
                    85                  90                  95
Glu Ser Glu Leu Pro Gln His Phe Glu Arg Ser Ser Ser Asp Thr Phe
            100                 105                 110

Ile Arg Ala Lys Tyr
        115

<210> SEQ ID NO 87
<211> LENGTH: 1101
<212> TYPE: DNA
<213> ORGANISM: Arabidopsis thaliana

<400> SEQUENCE: 87
atggcggtga acgcgtgtct atctccgccg gagatgatgg ctgtccggcc aggggaaggc     60
gttccgaatt caaatctac gcagggaaaa actaggctct atctcaccaa accttcatgg    120
atagtcagaa ctcagtctgg agctaagacg tgtatgaagt cgaaggcgaa aggacgatgc    180
gtaatctgcc atggaagtgg aagagtcgat tgtttcaatt gttgtgggaa agggaggact    240
aattgtgtgg atgtggaaat gcttccaaga ggagaatggc ctaaatggtg caagagttgt    300
ggagggagtg gattaagtga ctgttctcgc tgtcttggca ccggagagcg cgcatctttc    360
ttcttcttgt ggttcgatat tcttatcgtt atgtcttccg tcgctttgcc ggcgatgagc    420
tgccggagct caggtgaaca agtgaaggag attcgcgttt gtacgaatcg cacctgccga    480
agacaaggct ccttccagat tctcgagact ttaacagctc tcgcacctcc cgaactccga    540
gtcactcact gcgcttgcct cggccgatgc ggctccggtc aaacctcgt ggctctccct    600 caaggtctca tcctacgtca ctgcgccacg ccttctcgag ctgctgaaat tttgttcagc    660
ctatgtggtg acgtcgtga agcttcttca tcctccgccg tcacagacgc tctcacggct    720
ttagcgttaa ccaacaatgc tctctctcaa atcgatgcgg gaaatttctc tgaagccgaa    780
gcacttctca ctcaggcttt agagctgaaa ccctacggtg cttgcatag aatattcaaa    840 cacagatcag tagcaaaatt gggaatgctt gattactctg ggctcttga agatataagc    900 caagctctag ctttagctcc taactattct gagccctaca tatgccaagg ggatgtctac    960
gtagcaaaag tcaatatga tcttgcagag aagtcatact tgacatgtct agagatagat   1020
ccttctcttc gcagatcgaa accattcaag gcccggattg cgaaacttca acagaaagtt   1080
gttgaactag atgtaacata g                                              1101

<210> SEQ ID NO 88
<211> LENGTH: 366
<212> TYPE: PRT
<213> ORGANISM: Arabidopsis thaliana

<400> SEQUENCE: 88

Met Ala Val Asn Ala Cys Leu Ser Pro Pro Glu Met Met Ala Val Arg
1               5                   10                  15

Pro Gly Glu Gly Val Pro Asn Ser Lys Ser Thr Gln Gly Lys Thr Arg
            20                  25                  30

Leu Tyr Leu Thr Lys Pro Ser Trp Ile Val Arg Thr Gln Ser Gly Ala
        35                  40                  45

Lys Thr Cys Met Lys Ser Lys Ala Lys Gly Arg Cys Val Ile Cys His
    50                  55                  60

Gly Ser Gly Arg Val Asp Cys Phe Asn Cys Cys Gly Lys Gly Arg Thr
65                  70                  75                  80

Asn Cys Val Asp Val Glu Met Leu Pro Arg Gly Glu Trp Pro Lys Trp
                85                  90                  95
```

```
Cys Lys Ser Cys Gly Gly Ser Gly Leu Ser Asp Cys Ser Arg Cys Leu
                100                 105                 110
Gly Thr Gly Glu Arg Ala Ser Phe Phe Leu Trp Phe Asp Ile Leu
                115                 120                 125
Ile Val Met Ser Ser Val Ala Leu Pro Ala Met Ser Cys Arg Ser Ser
130                 135                 140
Gly Glu Gln Val Lys Glu Ile Arg Val Cys Thr Asn Arg Thr Cys Arg
145                 150                 155                 160
Arg Gln Gly Ser Phe Gln Ile Leu Glu Thr Leu Thr Ala Leu Ala Pro
                165                 170                 175
Pro Glu Leu Arg Val Thr His Cys Ala Cys Leu Gly Arg Cys Gly Ser
                180                 185                 190
Gly Pro Asn Leu Val Ala Leu Pro Gln Gly Leu Ile Leu Arg His Cys
                195                 200                 205
Ala Thr Pro Ser Arg Ala Ala Glu Ile Leu Phe Ser Leu Cys Gly Asp
    210                 215                 220
Gly Arg Glu Ala Ser Ser Ser Ala Val Thr Asp Ala Leu Thr Ala
225                 230                 235                 240
Leu Ala Leu Thr Asn Asn Ala Leu Ser Gln Ile Asp Ala Gly Asn Phe
                245                 250                 255
Ser Glu Ala Glu Ala Leu Leu Thr Gln Ala Leu Glu Leu Lys Pro Tyr
                260                 265                 270
Gly Gly Leu His Arg Ile Phe Lys His Arg Ser Val Ala Lys Leu Gly
            275                 280                 285
Met Leu Asp Tyr Ser Gly Ala Leu Glu Asp Ile Ser Gln Ala Leu Ala
    290                 295                 300
Leu Ala Pro Asn Tyr Ser Glu Pro Tyr Ile Cys Gln Gly Asp Val Tyr
305                 310                 315                 320
Val Ala Lys Gly Gln Tyr Asp Leu Ala Glu Lys Ser Tyr Leu Thr Cys
                325                 330                 335
Leu Glu Ile Asp Pro Ser Leu Arg Arg Ser Lys Pro Phe Lys Ala Arg
                340                 345                 350
Ile Ala Lys Leu Gln Gln Lys Val Val Glu Leu Asp Val Thr
                355                 360                 365

<210> SEQ ID NO 89
<211> LENGTH: 1123
<212> TYPE: DNA
<213> ORGANISM: Arabidopsis thaliana

<400> SEQUENCE: 89
tctctcatca cttcttgtct gaaaaaatgt tggaaacaga ccttgaagct cggatgcaaa      60
tcctgcgtga gtctggtttt caagaaagcc aaggagatga tgatacccttt gctcaacgag    120 ctgaatggtt ttaccaggga cgacctttgc ttctctcact ttgtctggac ctgtacaacg    180
gctacgtcac tctcttgggt cgttcttctc atcagaccag acttaaaccc actacttctc    240
ttccgaacca gcttctccaa gatgatgatg actgcatttc ggacattgat tccgttagtg    300
aggtcagttc tgaagttgag agcaccttat cctttcaaca gatgaaagat cctactgcgg    360
tttctgagaa agtcgatgag cttgtatccc aacttgtgac agcaagcttg gacaaagaga    420
ttctgaaaca cgagttactt cacaaggacc aacagtttca tgaagcctcc aagactatag    480
agctgttgaa gaagtttgtc atgttgctgg agatggagaa agaagtggct gtggaggaaa    540
acgctaatct tggctacaaa ctcacttctc tcttggagga gaacagagag ctagccactg    600
aggcattgtt catgaagaac gaagctgttg ggcttgctag gtgtgtgctt aagatgagag    660
```

-continued

```
atgaccactt tcacaaggtc tgcattctcc agaaccgcat ctactcgctt caggcatcta      720
ggaactcaga gcccgtctct gataaggtct catacggatg ctttggcctg gataagcata      780
agaccaaaaa gaagaaggag aacaaaaccg aagagaagaa gcctggattc aagtggttga      840
agaaactgaa caccattaac ctgtttacaa agtgcagcct taacccatcg gctgctgctc      900
catcatgctg cactttcgac ttgccttatt agcttaatcc tttgctgtat tagtaaacta      960
tgaacaatgc atacataact gtgtatgttc tatcgcctta ttaggtttaa tgcttttcag     1020
tgcatcgccc tgatgcacag tttgttgtac cccgcataca atctgtggct ccttgatcca     1080
catatgtatg gttttcatga ctcacttatc tggttaacac aac                       1123
```

<210> SEQ ID NO 90
<211> LENGTH: 301
<212> TYPE: PRT
<213> ORGANISM: Arabidopsis thaliana

<400> SEQUENCE: 90

```
Met Leu Glu Thr Asp Leu Glu Ala Arg Met Gln Ile Leu Arg Glu Ser
1               5                   10                  15

Gly Phe Gln Glu Ser Gln Gly Asp Asp Thr Phe Ala Gln Arg Ala
            20                  25                  30

Glu Trp Phe Tyr Gln Gly Arg Pro Leu Leu Ser Leu Cys Leu Asp
        35                  40                  45

Leu Tyr Asn Gly Tyr Val Thr Leu Leu Gly Arg Ser Ser His Gln Thr
    50                  55                  60

Arg Leu Lys Pro Thr Thr Ser Leu Pro Asn Gln Leu Leu Gln Asp Asp
65                  70                  75                  80

Asp Asp Cys Ile Ser Asp Ile Asp Ser Val Ser Glu Val Ser Ser Glu
                85                  90                  95

Val Glu Ser Thr Leu Ser Phe Gln Gln Met Lys Asp Pro Thr Ala Val
            100                 105                 110

Ser Glu Lys Val Asp Glu Leu Val Ser Gln Leu Val Thr Ala Ser Leu
        115                 120                 125

Asp Lys Glu Ile Leu Lys His Glu Leu Leu His Lys Asp Gln Gln Phe
    130                 135                 140

His Glu Ala Ser Lys Thr Ile Glu Leu Leu Lys Lys Phe Val Met Leu
145                 150                 155                 160

Leu Glu Met Glu Lys Glu Val Ala Val Glu Glu Asn Ala Asn Leu Gly
                165                 170                 175

Tyr Lys Leu Thr Ser Leu Leu Glu Glu Asn Arg Glu Leu Ala Thr Glu
            180                 185                 190

Ala Leu Phe Met Lys Asn Glu Ala Val Gly Leu Ala Arg Cys Val Leu
        195                 200                 205

Lys Met Arg Asp Asp His Phe His Lys Val Cys Ile Leu Gln Asn Arg
    210                 215                 220

Ile Tyr Ser Leu Gln Ala Ser Arg Asn Ser Glu Pro Val Ser Asp Lys
225                 230                 235                 240

Val Ser Tyr Gly Cys Phe Gly Leu Asp Lys His Lys Thr Lys Lys Lys
                245                 250                 255

Lys Glu Asn Lys Thr Glu Glu Lys Lys Pro Gly Phe Lys Trp Leu Lys
            260                 265                 270

Lys Leu Asn Thr Ile Asn Leu Phe Thr Lys Cys Ser Leu Asn Pro Ser
        275                 280                 285

Ala Ala Ala Pro Ser Cys Cys Thr Phe Asp Leu Pro Tyr
    290                 295                 300
```

<210> SEQ ID NO 91
<211> LENGTH: 1186
<212> TYPE: DNA
<213> ORGANISM: Arabidopsis thaliana

<400> SEQUENCE: 91

```
tgaacaaacg tgtcagctat cttctctctc tcactatttc tgggttgaag aagatgaaga      60
acaaagcatc catggaagct ccacagttgc catctctctc tgaccttgaa gctcggatgc     120
aaatcctgcg tgagtctggt tttcaagaaa gccaaggaga tgatgatacc tttgctcaac     180
gagctgaatg gttttaccag ggacgacctt tgcttctctc actttgtctg gacctgtaca     240
acggctacgt cactctcttg ggtcgttctt ctcatcagac cagacttaaa cccactactt     300
ctcttccgaa ccagcttctc aagatgatg atgactgcat ttcggacatt gattccgtta      360
gtgaggtcag ttctgaagtt gagagcacct tatcctttca acagatgaaa gatcctactg     420
cggtttctga gaaagtcgat gagcttgtat cccaacttgt gacagcaagc ttggacaaag     480
agattctgaa acacgagtta cttcacaagg accaacagtt tcatgaagcc tccaagacta     540
tagagctgtt gaagaagttt gtcatgttgc tggagatgga gaaagaagtg gctgtggagg     600
aaaacgctaa tcttggctac aaactcactt ctctctctgga ggagaacaga gagctagcca     660
ctgaggcatt gttcatgaag aacgaagctg ttgggcttgc taggtgtgtg cttaagatga     720
gagatgacca ctttcacaag gtctgcattc tccagaaccg catctactcg cttcaggcat     780
ctaggaactc agagcccgtc tctgataagg tctcatacgg atgctttggc ctggataagc     840
ataagaccaa aaagaagaag gagaacaaaa ccgaagagaa gaagcctgga ttcaagtggt     900
tgaagaaact gaacaccatt aacctgttta caaagtgcag ccttaaccca tcggctgctg     960
ctccatcatg ctgcactttc gacttgcctt attagcttaa tcctttgctg tattagtaaa    1020
ctatgaacaa tgcatacata actgtgtatg ttctatcgcc ttattaggtt taatgctttt    1080
cagtgcatcg ccctgatgca cagtttgttg taccccgcat acaatctgtg gctccttgat    1140
ccacatatgt atggttttca tgactcactt atctggttaa cacaac                  1186
```

<210> SEQ ID NO 92
<211> LENGTH: 313
<212> TYPE: PRT
<213> ORGANISM: Arabidopsis thaliana

<400> SEQUENCE: 92

```
Met Lys Asn Lys Ala Ser Met Glu Ala Pro Gln Leu Pro Ser Leu Ser
1               5                   10                  15

Asp Leu Glu Ala Arg Met Gln Ile Leu Arg Glu Ser Gly Phe Gln Glu
            20                  25                  30

Ser Gln Gly Asp Asp Asp Thr Phe Ala Gln Arg Ala Glu Trp Phe Tyr
        35                  40                  45

Gln Gly Arg Pro Leu Leu Leu Ser Leu Cys Leu Asp Leu Tyr Asn Gly
    50                  55                  60

Tyr Val Thr Leu Leu Gly Arg Ser Ser His Gln Thr Arg Leu Lys Pro
65                  70                  75                  80

Thr Thr Ser Leu Pro Asn Gln Leu Leu Gln Asp Asp Asp Cys Ile
                85                  90                  95

Ser Asp Ile Asp Ser Val Ser Glu Val Ser Ser Glu Val Glu Ser Thr
            100                 105                 110

Leu Ser Phe Gln Gln Met Lys Asp Pro Thr Ala Val Ser Glu Lys Val
```

```
                 115                 120                 125
Asp Glu Leu Val Ser Gln Leu Val Thr Ala Ser Leu Asp Lys Glu Ile
            130                 135                 140
Leu Lys His Glu Leu Leu His Lys Asp Gln Gln Phe His Glu Ala Ser
145                 150                 155                 160
Lys Thr Ile Glu Leu Leu Lys Lys Phe Val Met Leu Leu Glu Met Glu
                165                 170                 175
Lys Glu Val Ala Val Glu Glu Asn Ala Asn Leu Gly Tyr Lys Leu Thr
            180                 185                 190
Ser Leu Leu Glu Glu Asn Arg Glu Leu Ala Thr Glu Ala Leu Phe Met
            195                 200                 205
Lys Asn Glu Ala Val Gly Leu Ala Arg Cys Val Leu Lys Met Arg Asp
            210                 215                 220
Asp His Phe His Lys Val Cys Ile Leu Gln Asn Arg Ile Tyr Ser Leu
225                 230                 235                 240
Gln Ala Ser Arg Asn Ser Glu Pro Val Ser Asp Lys Val Ser Tyr Gly
                245                 250                 255
Cys Phe Gly Leu Asp Lys His Lys Thr Lys Lys Lys Glu Asn Lys
            260                 265                 270
Thr Glu Glu Lys Lys Pro Gly Phe Lys Trp Leu Lys Lys Leu Asn Thr
            275                 280                 285
Ile Asn Leu Phe Thr Lys Cys Ser Leu Asn Pro Ser Ala Ala Ala Pro
            290                 295                 300
Ser Cys Cys Thr Phe Asp Leu Pro Tyr
305                 310

<210> SEQ ID NO 93
<211> LENGTH: 2761
<212> TYPE: DNA
<213> ORGANISM: Arabidopsis thaliana

<400> SEQUENCE: 93
aaaatacaca atggacaaag ctcttggata aagttttcaa agtaacacaa gaggcagctt      60
cttgaggttt tctctcttcc aacttttttg ctttacttac tactgaggtt ttctattcct     120
ttggaagctt cgttgatggg ttcaacacaa gatctaaaat gtaacatttc ttttcttaaa     180
tttcctgcaa agttcgatgt agttcatgtt ttttttttc cattcttttc cttataaagt      240
gtcgtccaca tttgcttgac gggatacaaa acgaaaccca agtctctgtc ttcgtctcct     300
tctttcttct tctctctgtc atcatttgc ttttttttt tctcctacat gccctagatt       360
ttgggtttct gaaataaaaa atggctcaca ctaggacttt cacttccaga aaccgtagcg     420
tttctctctc aaacccatct ttctccattg acggatttga caactcaact gtgactttag     480
gctacacggg tcctcttcga acccagagaa taagacctcc tttagtgcaa atgagtggtc     540
ctattcactc tactcgcaga acagaacctc tcttctctcc ttctcctcaa gaatctcctg     600
attcctcttc taccgttgat gttccacctg aagatgattt cgtcttcaaa aacgcaaatc     660
tcttgagatc tggacaatta gggatgtgca atgatcctta ctgcactact tgcccttctt     720
actacaaccg ccaagctgct caattgcaca cttccagagt ttctgcctct aggtttcgca     780
ctgttctgta tggtgatgct agaggttggg ctaagcgatt tgcctcctct gttcgtagat     840
gcttacccgg aataatgaat cctcattcca aatttgttca agtctggact agagtcttag     900
cctttcaag cttagtggcc atttttatag accctctctt ctttttcctc ttattgatcc      960
aacaagacaa caaatgcata gcgattgatt ggcgtgcgac taaagtattg gtgtctctta    1020
```

| | | |
|---|---|---|
| gaagtataac ggatcttata ttcttcatta acattctgct tcagtttagg ttggcctatg | 1080 | |
| tagctcctga gtctagaata gttggtgccg gccagttagt tgatcatcca agaaaaattg | 1140 | |
| ctcgccatta cttccgagga aagtttctcc ttgacatgtt catagtcttt cccattccac | 1200 | |
| agataatgat attaaggata ataccattac acttaggcac acgcagggaa gaatctgaga | 1260 | |
| aacagatttt acgcgctacg gttctttttc aatacattcc aaagttatat agactcttac | 1320 | |
| ctcttcttgc tggacaaaca tctactggct tcatatttga gtcagcttgg gctaattttg | 1380 | |
| ttattaatct tctcaccttc atgcttgctg gtcacgctgt tggctcttgc tggtatctct | 1440 | |
| ctgctctgca gagagttaag aaatgcatgc tgaatgcttg gaatatttct gcggatgaac | 1500 | |
| gtagaaatct tatcgattgt gctcgtggaa gttatgcatc gaagtcacaa cgagatctgt | 1560 | |
| ggagagataa tgctagtgtc aatgcttgtt ttcaagaaaa tggttatacc tatgggatct | 1620 | |
| atttgaaggc agtgaatctt accaatgaat ctagtttctt cacaagattc agttattctc | 1680 | |
| tgtattgggg attccaacaa ataagcacac ttgctggaaa cttatcccca agttactcag | 1740 | |
| tgggtgaggt tttcttttaca atgggtatca ttggactagg gcttttgctt tttgcgcggc | 1800 | |
| ttatcggtaa catgcacaac ttccttcaat cacttgatcg aaggaggatg gaaatgatgc | 1860 | |
| tgagaaagcg tgatgtggag cagtggatga gccatagacg tttgccagaa gatataagaa | 1920 | |
| agagggtgag agaggttgag cggtacactt gggctgcgac aagaggagtt aacgaagaat | 1980 | |
| tgctatttga gaacatgcct gatgaccttc aaagagatat aagaagacac ctcttcaaat | 2040 | |
| ttctcaagaa ggtgagaata ttttcgttga tggatgaatc agttttagat tcaatcagag | 2100 | |
| agaggctgaa acagaggact tacataagga gtagcacggt gttgcatcac agaggtctag | 2160 | |
| tagagaaaat ggtattcata gtgagaggtg agatggagag cattggagaa gacggttctg | 2220 | |
| ttcttccttt atcagaagga gacgtttgtg gtgaagaact tctcacttgg tgcctctctt | 2280 | |
| ctataaaccc cgaaacttgg aactttggag ctgaatacgt tttgaaactt gcagatggga | 2340 | |
| cgaggataaa gatgccacca aagggattgg ttagcaacag aaatgttagg tgtgtgacaa | 2400 | |
| acgtggaggc gttttcgctg agtgtagcag atcttgaaga tgtaacaagc ttgttttcaa | 2460 | |
| gattcttaag aagccatcga gtgcaaggag ctataaggta cgagtctcct tattggaggt | 2520 | |
| tacgagcagc tatgcagatc caagtggctt ggagataccg aaagagacaa ctccagagat | 2580 | |
| taaacactgc tcactccaat tccaaccgtt aaatttgatg atgatgtttg gtttggtaga | 2640 | |
| ttagtaattt tattttgaag tataaagctt agtgattcac tataaagat gaatcgatga | 2700 | |
| ttcattcgtt gtaatcaatt cactcattag tgtttcttaa gtatcttttt gctgtttttc | 2760 | |
| c | 2761 | |

<210> SEQ ID NO 94
<211> LENGTH: 743
<212> TYPE: PRT
<213> ORGANISM: Arabidopsis thaliana

<400> SEQUENCE: 94

Met Ala His Thr Arg Thr Phe Thr Ser Arg Asn Arg Ser Val Ser Leu
1               5                   10                  15

Ser Asn Pro Ser Phe Ser Ile Asp Gly Phe Asp Asn Ser Thr Val Thr
            20                  25                  30

Leu Gly Tyr Thr Gly Pro Leu Arg Thr Gln Arg Ile Arg Pro Pro Leu
        35                  40                  45

Val Gln Met Ser Gly Pro Ile His Ser Thr Arg Arg Thr Glu Pro Leu
    50                  55                  60

```
            Phe Ser Pro Ser Pro Gln Glu Ser Pro Asp Ser Ser Thr Val Asp
            65                  70                  75                  80

Val Pro Pro Glu Asp Asp Phe Val Phe Lys Asn Ala Asn Leu Leu Arg
                            85                  90                  95

Ser Gly Gln Leu Gly Met Cys Asn Asp Pro Tyr Cys Thr Thr Cys Pro
                            100                 105                 110

Ser Tyr Tyr Asn Arg Gln Ala Ala Gln Leu His Thr Ser Arg Val Ser
                        115                 120                 125

Ala Ser Arg Phe Arg Thr Val Leu Tyr Gly Asp Ala Arg Gly Trp Ala
                    130                 135                 140

Lys Arg Phe Ala Ser Ser Val Arg Arg Cys Leu Pro Gly Ile Met Asn
            145                 150                 155                 160

Pro His Ser Lys Phe Val Gln Val Trp Thr Arg Val Leu Ala Phe Ser
                            165                 170                 175

Ser Leu Val Ala Ile Phe Ile Asp Pro Leu Phe Phe Leu Leu Leu
                        180                 185                 190

Ile Gln Gln Asp Asn Lys Cys Ile Ala Ile Asp Trp Arg Ala Thr Lys
                        195                 200                 205

Val Leu Val Ser Leu Arg Ser Ile Thr Asp Leu Ile Phe Phe Ile Asn
            210                 215                 220

Ile Leu Leu Gln Phe Arg Leu Ala Tyr Val Ala Pro Glu Ser Arg Ile
            225                 230                 235                 240

Val Gly Ala Gly Gln Leu Val Asp His Pro Arg Lys Ile Ala Arg His
                            245                 250                 255

Tyr Phe Arg Gly Lys Phe Leu Leu Asp Met Phe Ile Val Phe Pro Ile
                            260                 265                 270

Pro Gln Ile Met Ile Leu Arg Ile Ile Pro Leu His Leu Gly Thr Arg
                    275                 280                 285

Arg Glu Glu Ser Glu Lys Gln Ile Leu Arg Ala Thr Val Leu Phe Gln
                    290                 295                 300

Tyr Ile Pro Lys Leu Tyr Arg Leu Leu Pro Leu Leu Ala Gly Gln Thr
            305                 310                 315                 320

Ser Thr Gly Phe Ile Phe Glu Ser Ala Trp Ala Asn Phe Val Ile Asn
                            325                 330                 335

Leu Leu Thr Phe Met Leu Ala Gly His Ala Val Gly Ser Cys Trp Tyr
                        340                 345                 350

Leu Ser Ala Leu Gln Arg Val Lys Lys Cys Met Leu Asn Ala Trp Asn
                    355                 360                 365

Ile Ser Ala Asp Glu Arg Arg Asn Leu Ile Asp Cys Ala Arg Gly Ser
            370                 375                 380

Tyr Ala Ser Lys Ser Gln Arg Asp Leu Trp Arg Asp Asn Ala Ser Val
            385                 390                 395                 400

Asn Ala Cys Phe Gln Glu Asn Gly Tyr Thr Tyr Gly Ile Tyr Leu Lys
                            405                 410                 415

Ala Val Asn Leu Thr Asn Glu Ser Ser Phe Thr Arg Phe Ser Tyr
                        420                 425                 430

Ser Leu Tyr Trp Gly Phe Gln Gln Ile Ser Thr Leu Ala Gly Asn Leu
                    435                 440                 445

Ser Pro Ser Tyr Ser Val Gly Glu Val Phe Phe Thr Met Gly Ile Ile
                    450                 455                 460

Gly Leu Gly Leu Leu Leu Phe Ala Arg Leu Ile Gly Asn Met His Asn
            465                 470                 475                 480

Phe Leu Gln Ser Leu Asp Arg Arg Met Glu Met Leu Arg Lys
                            485                 490                 495
```

Arg Asp Val Glu Gln Trp Met Ser His Arg Arg Leu Pro Glu Asp Ile
            500                 505                 510
Arg Lys Arg Val Arg Glu Val Glu Arg Tyr Thr Trp Ala Ala Thr Arg
        515                 520                 525
Gly Val Asn Glu Glu Leu Leu Phe Glu Asn Met Pro Asp Leu Gln
    530                 535                 540
Arg Asp Ile Arg Arg His Leu Phe Lys Phe Leu Lys Lys Val Arg Ile
545                 550                 555                 560
Phe Ser Leu Met Asp Glu Ser Val Leu Asp Ser Ile Arg Glu Arg Leu
                565                 570                 575
Lys Gln Arg Thr Tyr Ile Arg Ser Ser Thr Val Leu His His Arg Gly
                580                 585                 590
Leu Val Glu Lys Met Val Phe Ile Val Arg Gly Glu Met Glu Ser Ile
            595                 600                 605
Gly Glu Asp Gly Ser Val Leu Pro Leu Ser Gly Asp Val Cys Gly
        610                 615                 620
Glu Glu Leu Leu Thr Trp Cys Leu Ser Ser Ile Asn Pro Glu Thr Trp
625                 630                 635                 640
Asn Phe Gly Ala Glu Tyr Val Leu Lys Leu Ala Asp Gly Thr Arg Ile
                645                 650                 655
Lys Met Pro Pro Lys Gly Leu Val Ser Asn Arg Asn Val Arg Cys Val
            660                 665                 670
Thr Asn Val Glu Ala Phe Ser Leu Ser Val Ala Asp Leu Glu Asp Val
        675                 680                 685
Thr Ser Leu Phe Ser Arg Phe Leu Arg Ser His Arg Val Gln Gly Ala
    690                 695                 700
Ile Arg Tyr Glu Ser Pro Tyr Trp Arg Leu Arg Ala Ala Met Gln Ile
705                 710                 715                 720
Gln Val Ala Trp Arg Tyr Arg Lys Arg Gln Leu Gln Arg Leu Asn Thr
                725                 730                 735
Ala His Ser Asn Ser Asn Arg
            740

<210> SEQ ID NO 95
<211> LENGTH: 1952
<212> TYPE: DNA
<213> ORGANISM: Arabidopsis thaliana

<400> SEQUENCE: 95
tctctctcca atccaaaagg aagaacaaga acaagaaagc tcacaagaag tttcatcttc      60
accaaatgca aaagaagttg atacaatgtc tctttgctgt gatcttcaaa tcaatctcaa     120
taaccaattt actttcttcg tcaatcagga tttgatctca gagtactcag gcttcttgag     180
gaagatgata aaacagagca ataagaagaa aagaatcac aagaacagta gaatcatcat     240
cgaggttgaa gattttccag gtgggtcaga tgggttcgac ttggttttaa gattctgtta     300
tggtggagga atctcgatag atgtctcaaa tgtgtccatt ttgcattgct cttctgtctt     360
ccttgagatg acagagaaac tctgttcctc gaatctcttg cttcgaacag agaagtttct     420
agaaggaatg ttctactggt cctggaacga catcgtattg tgtctcaaga gctgcgagca     480
agtgttctta cacgctgatt cttacggtct tgttgataag cttgttttcg ggttttagc      540 caaaatccct cagaattcag acgtgagtca tgtctttca tcatcctctc cgtcttcctc      600
tgcctctgcc tcagcctcct ctcagtcgcc ggagacggca atgattaggt cgtattcaga     660
caaaaggtct acttcgaggt cttttttcttg caggacaagt aacgagtggt ggttcgacga     720

```
tatgtcaatt ctcgggccaa aaatcattga aaagctgata aatacacttg gtgcgcatga    780
taagaacaat gacagcttgg tcctcacaaa atttcttctc cattacctca agacaaaggt    840
cccaaacaag tcaaccaaca agctcgagta ttcaggttta gctgatacag cggttcaagg    900
agtggttttc gcagcgaaaa ccgcgttttc atgcagaaaa atgttctggg ttctgcgagt    960
tttatcggga tttagcataa gtaaagaatc aagaattggt ttagagaggg ttataggaga   1020
aatgctggat caagcaacac ttgatgatct tctgatacca gctggaggaa aaggagaaaa   1080
aggggtttac gatgtggatt tggtgataag attactcaaa gtgtttgtaa gaattggaaa   1140
cacagaagaa ggagatcaga atttgagaat gagaagaatt gggaagttga ttgataagta   1200
tctcagagag atatctccag accagaatct taaagtgtca agtttcttg aagttgcaga    1260 gagtttgcca gattcagcta gagattggtt tgatggatta tacagagcca ttaacatcta   1320
tcttgagtct catccgaaac tatcatccga ggatagaaca aaactatgtc gatgtctaaa   1380
ctacaagaaa ttgacattgg acacatgcaa acaacttgca aaaaatccca agatccctcc   1440
aaatattgca gttcaagcac tcaagtcaca acaattatca aacgagactc gaccacactc   1500
aagagaggac aagaacaaag taaacaagat ctggaattca cgtaagtact agaagagaa    1560 accaatactg gtgtgtttga aaggttttga tatgtcggag aagtttgaag atgatctaat   1620
gatgaatttg gagaggaagc aatggaataa ttctgaaaaa gttagtaagg agaagaagag   1680
tgaagtaatg tcaagatctg tgagacatgg acatacacat tcaagttcta gttttccaag   1740
gctttgttaa ataattaatt cactcgtcat ttttttctta tttctctaga tatagatttt   1800
tatgtcatca tatcatcatc acacacatgc acgtctcgtg tatattataa gcttttttcat  1860 gcaaaatgta ttttacgtag ttttgagaat gcatataatt atgtccttgt ggatgcaaat   1920
aaaatggata ttttgtaatt tgagtaatca tg                                  1952
```

<210> SEQ ID NO 96
<211> LENGTH: 554
<212> TYPE: PRT
<213> ORGANISM: Arabidopsis thaliana

<400> SEQUENCE: 96

```
Met Ser Leu Cys Cys Asp Leu Gln Ile Asn Leu Asn Asn Gln Phe Thr
1               5                   10                  15

Phe Phe Val Asn Gln Asp Leu Ile Ser Glu Tyr Ser Gly Phe Leu Arg
            20                  25                  30

Lys Met Ile Lys Gln Ser Asn Lys Lys Lys Asn His Lys Asn Ser
        35                  40                  45

Arg Ile Ile Ile Glu Val Glu Asp Phe Pro Gly Gly Ser Asp Gly Phe
    50                  55                  60

Asp Leu Val Leu Arg Phe Cys Tyr Gly Gly Gly Ile Ser Ile Asp Val
65                  70                  75                  80

Ser Asn Val Ser Ile Leu His Cys Ser Ser Val Phe Leu Glu Met Thr
                85                  90                  95

Glu Lys Leu Cys Ser Ser Asn Leu Leu Leu Arg Thr Glu Lys Phe Leu
            100                 105                 110

Glu Gly Met Phe Tyr Trp Ser Trp Asn Asp Ile Val Leu Cys Leu Lys
        115                 120                 125

Ser Cys Glu Gln Val Phe Leu His Ala Asp Ser Tyr Gly Leu Val Asp
    130                 135                 140

Lys Leu Val Phe Gly Val Leu Ala Lys Ile Pro Gln Asn Ser Asp Val
145                 150                 155                 160
```

Ser His Val Phe Ser Ser Ser Pro Ser Ser Ala Ser Ala Ser
            165                 170                 175

Ala Ser Ser Gln Ser Pro Glu Thr Ala Met Ile Arg Ser Tyr Ser Asp
                180                 185                 190

Lys Arg Ser Thr Ser Arg Ser Phe Ser Cys Arg Thr Ser Asn Glu Trp
            195                 200                 205

Trp Phe Asp Asp Met Ser Ile Leu Gly Pro Lys Ile Ile Glu Lys Leu
        210                 215                 220

Ile Asn Thr Leu Gly Ala His Asp Lys Asn Asn Asp Ser Leu Val Leu
225                 230                 235                 240

Thr Lys Phe Leu Leu His Tyr Leu Lys Thr Lys Val Pro Asn Lys Ser
                245                 250                 255

Thr Asn Lys Leu Glu Tyr Ser Gly Leu Ala Asp Thr Ala Val Gln Gly
            260                 265                 270

Val Val Phe Ala Ala Lys Thr Ala Phe Ser Cys Arg Lys Met Phe Trp
        275                 280                 285

Val Leu Arg Val Leu Ser Gly Phe Ser Ile Ser Lys Glu Ser Arg Ile
290                 295                 300

Gly Leu Glu Arg Val Ile Gly Glu Met Leu Asp Gln Ala Thr Leu Asp
305                 310                 315                 320

Asp Leu Leu Ile Pro Ala Gly Gly Lys Gly Glu Lys Gly Val Tyr Asp
                325                 330                 335

Val Asp Leu Val Ile Arg Leu Leu Lys Val Phe Val Arg Ile Gly Asn
            340                 345                 350

Thr Glu Glu Gly Asp Gln Asn Leu Arg Met Arg Arg Ile Gly Lys Leu
        355                 360                 365

Ile Asp Lys Tyr Leu Arg Glu Ile Ser Pro Asp Gln Asn Leu Lys Val
370                 375                 380

Ser Lys Phe Leu Glu Val Ala Glu Ser Leu Pro Asp Ser Ala Arg Asp
385                 390                 395                 400

Trp Phe Asp Gly Leu Tyr Arg Ala Ile Asn Ile Tyr Leu Glu Ser His
                405                 410                 415

Pro Lys Leu Ser Ser Glu Asp Arg Thr Lys Leu Cys Arg Cys Leu Asn
            420                 425                 430

Tyr Lys Lys Leu Thr Leu Asp Thr Cys Lys Gln Leu Ala Lys Asn Pro
        435                 440                 445

Lys Ile Pro Pro Asn Ile Ala Val Gln Ala Leu Lys Ser Gln Gln Leu
450                 455                 460

Ser Asn Glu Thr Arg Pro His Ser Arg Glu Asp Lys Asn Lys Val Asn
465                 470                 475                 480

Lys Ile Trp Asn Ser Arg Lys Tyr Leu Glu Glu Lys Pro Ile Leu Val
                485                 490                 495

Cys Leu Lys Gly Phe Asp Met Ser Glu Lys Phe Glu Asp Asp Leu Met
            500                 505                 510

Met Asn Leu Glu Arg Lys Gln Trp Asn Asn Ser Glu Lys Val Ser Lys
        515                 520                 525

Glu Lys Lys Ser Glu Val Met Ser Arg Ser Val Arg His Gly His Thr
530                 535                 540

His Ser Ser Ser Ser Phe Pro Arg Leu Cys
545                 550

<210> SEQ ID NO 97
<211> LENGTH: 1281
<212> TYPE: DNA

<213> ORGANISM: Arabidopsis thaliana

<400> SEQUENCE: 97

| | | |
|---|---|---|
| attgaaaaaa tgggggataag agaaaatgga ataatgcttg tgagcagaga gagagagcga | 60 |
| gcgaggaggc tagagaatcg agaatcgatc ttcgccgaac caccttgtct tctcttagct | 120 |
| catcgaatct ctccgtcgcc gtcgattctt cccgccgaag aggaggtcat ggacgtttct | 180 |
| gctagaaagt cacaaaaagc tgggcgcgaa aagttgagga gggaaaaact gaatgagcat | 240 |
| tttgttgaac tgggaaatgt actcgatcca gagagaccca agaatgacaa agccacgatt | 300 |
| ctgactgata ctgttcagtt gttgaaagag ctcacatctg aagtcaacaa actgaaatct | 360 |
| gagtacaccg cattgacaga tgagtcccgc gagttgacac aggagaaaaa cgacctgaga | 420 |
| gaagaaaaga catcgctgaa atcagatata gagaatctca atcttcaata ccagcagaga | 480 |
| ttaaggtcaa tgtctccatg gggagctgcg atggatcaca cagtcatgat ggctccacca | 540 |
| ccctcctttc catacctat gcctattgct atgcctcccg ggtcaatccc aatgcatcca | 600 |
| tcaatgccat cttacacata ctttgggaac cagaacccta gcatgatccc agctccatgt | 660 |
| cctacataca tgccctacat gcctcctaat acagtcgttg agcaacaatc cgtgcacatt | 720 |
| ccacagaacc ccggtaaccg ttctcgggaa cctagagcaa aggtttcaag agagagcaga | 780 |
| tctgagaaag cagaggactc caacgaagtt gcaacacaac tcgaattaaa accccctgga | 840 |
| tctacttctg ataaggatac attgcaaagg ccagagaaga caaagagatg taagagaaac | 900 |
| aacaacaaca actcaataga agaaagctct cattctagca agtgttcatc ttctccgagc | 960 |
| gtacgagacc acagttcttc cagtagcgta gctggtggcc aaaaacctga tgatgcaaaa | 1020 |
| tgattcgaaa gaatctgatg ttgatcatct caagtatcca agtatcgttt cgatgagtac | 1080 |
| tgtatatagt gcgagtacaa aatgcactta gctgtttaaa gcagtgtttt gatgcaccgt | 1140 |
| ggcattcgtt ttcctcggat agtcattct cagatgattt tcatccttaa taggtctgct | 1200 |
| ttagttctaa aactcggatg atttgtaatt tccagtgtcc aaatctacta atttattaa | 1260 |
| tcctataaat taaacaaact t | 1281 |

<210> SEQ ID NO 98
<211> LENGTH: 337
<212> TYPE: PRT
<213> ORGANISM: Arabidopsis thaliana

<400> SEQUENCE: 98

Met Gly Ile Arg Glu Asn Gly Ile Met Leu Val Ser Arg Glu Arg Glu
1               5                   10                  15

Arg Ala Arg Arg Leu Glu Asn Arg Glu Ser Ile Phe Ala Glu Pro Pro
            20                  25                  30

Cys Leu Leu Leu Ala His Arg Ile Ser Pro Pro Ser Ile Leu Pro
        35                  40                  45

Ala Glu Glu Val Met Asp Val Ser Ala Arg Lys Ser Gln Lys Ala
    50                  55                  60

Gly Arg Glu Lys Leu Arg Arg Glu Lys Leu Asn Glu His Phe Val Glu
65                  70                  75                  80

Leu Gly Asn Val Leu Asp Pro Glu Arg Pro Lys Asn Asp Lys Ala Thr
                85                  90                  95

Ile Leu Thr Asp Thr Val Gln Leu Leu Lys Glu Leu Thr Ser Glu Val
            100                 105                 110

Asn Lys Leu Lys Ser Glu Tyr Thr Ala Leu Thr Asp Glu Ser Arg Glu
        115                 120                 125

```
Leu Thr Gln Glu Lys Asn Asp Leu Arg Glu Lys Thr Ser Leu Lys
        130                 135                 140

Ser Asp Ile Glu Asn Leu Asn Leu Gln Tyr Gln Gln Arg Leu Arg Ser
145                 150                 155                 160

Met Ser Pro Trp Gly Ala Ala Met Asp His Thr Val Met Met Ala Pro
                165                 170                 175

Pro Pro Ser Phe Pro Tyr Pro Met Pro Ile Ala Met Pro Pro Gly Ser
            180                 185                 190

Ile Pro Met His Pro Ser Met Pro Ser Tyr Thr Tyr Phe Gly Asn Gln
        195                 200                 205

Asn Pro Ser Met Ile Pro Ala Pro Cys Pro Thr Tyr Met Pro Tyr Met
210                 215                 220

Pro Pro Asn Thr Val Val Glu Gln Gln Ser Val His Ile Pro Gln Asn
225                 230                 235                 240

Pro Gly Asn Arg Ser Arg Glu Pro Arg Ala Lys Val Ser Arg Glu Ser
                245                 250                 255

Arg Ser Glu Lys Ala Glu Asp Ser Asn Glu Val Ala Thr Gln Leu Glu
            260                 265                 270

Leu Lys Thr Pro Gly Ser Thr Ser Asp Lys Asp Thr Leu Gln Arg Pro
        275                 280                 285

Glu Lys Thr Lys Arg Cys Lys Arg Asn Asn Asn Asn Ser Ile Glu
290                 295                 300

Glu Ser Ser His Ser Ser Lys Cys Ser Ser Ser Pro Ser Val Arg Asp
305                 310                 315                 320

His Ser Ser Ser Ser Val Ala Gly Gly Gln Lys Pro Asp Asp Ala
                325                 330                 335

Lys

<210> SEQ ID NO 99
<211> LENGTH: 1330
<212> TYPE: DNA
<213> ORGANISM: Arabidopsis thaliana

<400> SEQUENCE: 99
ataatgcttg tgagcagaga gagagagcga gcgaggaggc tagagaatcg agaatcgatc      60
ttcgccgaac caccttgtct tctcttagct catcgaatct ctccgtcgcc gtcgattctt     120
cccgccggtg aatctctgcc ttattgtttt cttcaatttg atcgtcctga attcatcgtc     180
ctatttaggg tttcgatcac aatctgaaga ggaggtcatg gacgtttctg ctagaaagtc     240
acaaaaagct gggcgcgaaa agttgaggag ggaaaaactg aatgagcatt tgttgaact      300 gggaaatgta ctcgatccag agagacccaa gaatgacaaa gccacgattc tgactgatac     360
tgttcagttg ttgaaagagc tcacatctga agtcaacaaa ctgaaatctg agtacaccgc     420
attgacagat gagtcccgcg agttgacaca ggagaaaaac gacctgagag aagaaaagac     480
atcgctgaaa tcagatatag agaatctcaa tcttcaatac cagcagagat taaggtcaat     540
gtctccatgg ggagctgcga tggatcacac agtcatgatg ctccaccac cctccttttcc     600 atccctatg cctattgcta tgcctcccgg gtcaatccca atgcatccat caatgccatc     660
ttacacatac tttgggaacc agaaccctag catgatccca gctccatgtc ctacatacat     720
gccctacatg cctcctaata cagtcgttga gcaacaatcc gtgcacattc cacagaaccc     780
cggtaaccgt tctcgggaac ctagagcaaa ggtttcaaga gagagcagat ctgagaaagc     840
agaggactcc aacgaagttg caacacaact cgaattaaaa accctggat ctacttctga     900
```

```
taaggataca ttgcaaaggc cagagaagac aaagagatgt aagagaaaca acaacaacaa    960
ctcaatagaa gaaagctctc attctagcaa gtgttcatct tctccgagcg tacgagacca   1020
cagttcttcc agtagcgtag ctggtggcca aaaacctgat gatgcaaaat gattcgaaag   1080
aatctgatgt tgatcatctc aagtatccaa gtatcgtttc gatgagtact gtatatagtg   1140
cgagtacaaa atgcacttag ctgtttaaag cagtgttttg atgcaccgtg gcattcgttt   1200
tcctcggata gtcatttctc agatgatttt catccttaat aggtctgctt tagttctaaa   1260
actcggatga tttgtaattt ccagtgtcca aatctactaa ttttattaat cctataaatt   1320
aaacaaactt                                                          1330
```

<210> SEQ ID NO 100
<211> LENGTH: 284
<212> TYPE: PRT
<213> ORGANISM: Arabidopsis thaliana

<400> SEQUENCE: 100

```
Met Asp Val Ser Ala Arg Lys Ser Gln Lys Ala Gly Arg Glu Lys Leu
1               5                   10                  15

Arg Arg Glu Lys Leu Asn Glu His Phe Val Glu Leu Gly Asn Val Leu
            20                  25                  30

Asp Pro Glu Arg Pro Lys Asn Asp Lys Ala Thr Ile Leu Thr Asp Thr
        35                  40                  45

Val Gln Leu Leu Lys Glu Leu Thr Ser Glu Val Asn Lys Leu Lys Ser
    50                  55                  60

Glu Tyr Thr Ala Leu Thr Asp Glu Ser Arg Glu Leu Thr Gln Glu Lys
65                  70                  75                  80

Asn Asp Leu Arg Glu Glu Lys Thr Ser Leu Lys Ser Asp Ile Glu Asn
                85                  90                  95

Leu Asn Leu Gln Tyr Gln Gln Arg Leu Arg Ser Met Ser Pro Trp Gly
            100                 105                 110

Ala Ala Met Asp His Thr Val Met Met Ala Pro Pro Pro Ser Phe Pro
        115                 120                 125

Tyr Pro Met Pro Ile Ala Met Pro Pro Gly Ser Ile Pro Met His Pro
    130                 135                 140

Ser Met Pro Ser Tyr Thr Tyr Phe Gly Asn Gln Asn Pro Ser Met Ile
145                 150                 155                 160

Pro Ala Pro Cys Pro Thr Tyr Met Pro Tyr Met Pro Pro Asn Thr Val
                165                 170                 175

Val Glu Gln Gln Ser Val His Ile Pro Gln Asn Pro Gly Asn Arg Ser
            180                 185                 190

Arg Glu Pro Arg Ala Lys Val Ser Arg Glu Ser Arg Ser Glu Lys Ala
        195                 200                 205

Glu Asp Ser Asn Glu Val Ala Thr Gln Leu Glu Leu Lys Thr Pro Gly
    210                 215                 220

Ser Thr Ser Asp Lys Asp Thr Leu Gln Arg Pro Glu Lys Thr Lys Arg
225                 230                 235                 240

Cys Lys Arg Asn Asn Asn Asn Ser Ile Glu Glu Ser Ser His Ser
                245                 250                 255

Ser Lys Cys Ser Ser Ser Pro Ser Val Arg Asp His Ser Ser Ser Ser
            260                 265                 270

Ser Val Ala Gly Gly Gln Lys Pro Asp Asp Ala Lys
        275                 280
```